United States Patent
Wrobleski et al.

(10) Patent No.: US 6,878,732 B2
(45) Date of Patent: Apr. 12, 2005

(54) NK₁ ANTAGONISTS

(75) Inventors: Michelle Laci Wrobleski, Whitehouse Station, NJ (US); Gregory A. Reichard, Ann Arbor, MI (US); Neng-Yang Shih, North Caldwell, NJ (US); Dong Xiao, Warren, NJ (US)

(73) Assignee: Schering Corporation, Kenilworth, NJ (US)

( * ) Notice: Subject to any disclaimer, the term of this patent is extended or adjusted under 35 U.S.C. 154(b) by 14 days.

(21) Appl. No.: 10/386,577

(22) Filed: Mar. 12, 2003

(65) Prior Publication Data

US 2004/0072854 A1 Apr. 15, 2004

Related U.S. Application Data

(60) Provisional application No. 60/363,761, filed on Mar. 13, 2002.

(51) Int. Cl.⁷ .................... A61K 31/415; C07D 233/02; C07D 233/04; A61P 25/00
(52) U.S. Cl. ....................................... 514/385; 514/386
(58) Field of Search ........................... 548/316.4, 316.7; 514/385, 386

(56) References Cited

U.S. PATENT DOCUMENTS

| | | | |
|---|---|---|---|
| 4,629,727 A | * | 12/1986 | Kozlik et al. ............ 514/237.8 |
| 5,620,989 A | | 4/1997 | Harrison et al. |
| 6,455,571 B1 | * | 9/2002 | Maring et al. ............. 514/423 |

OTHER PUBLICATIONS

Kozlik et al, 1984, CAS:101:210713.*
Holan, et al. "Synthesis and insecticidal properties of ether analogs of DDT–pyrethroids" Chemical Abstracts Service, Columbus, Ohio, US, retrieved from STN Database accession no. 106:214159 (1986).
Heal, "Sibutramine: A novel anti–obesity drug. A review of the pharmacological evidence to differentiate it from d–amphetamine and d–fenfluramine" *International Journal of Obesity* 22, Suppl. No. 1:S18–S28 (1998).
PCT International Search Report dated Jul. 2, 2003 for corresponding PCT Application No. PCT/US03/07633.

* cited by examiner

*Primary Examiner*—Rita Desai
*Assistant Examiner*—Robert Shiao
(74) *Attorney, Agent, or Firm*—Thomas A. Blinka

(57) ABSTRACT

A NK₁ antagonist having the formula (I), with the variables defined herein, which is useful for treating a number of disorders, including emesis, depression, anxiety and cough:

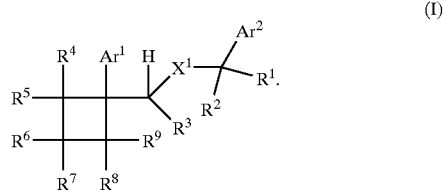

(I)

26 Claims, No Drawings

NK₁ ANTAGONISTS

REFERENCE TO RELATED APPLICATION

This application claims the benefit of U.S. Provisional Application Ser. No. 60/363,761 filed Mar. 13, 2002, the disclosure of which is incorporated herein by reference thereto.

BACKGROUND OF THE INVENTION

The invention relates to antagonists of the neuropeptide neurokinin-1 ($NK_1$ or NK-1) receptor.

Tachykinins are peptide ligands for neurokinin receptors. Neurokinin receptors, such as $NK_1$, $NK_2$ and $NK_3$, are involved in a variety of biological processes. They can be found in a mammal's nervous and circulatory systems, as well as in peripheral tissues. Consequently, the modulation of these types of receptors have been studied to potentially treat or prevent various mammalian disease states. For instance, $NK_1$ receptors have been reported to be involved in microvascular leakage and mucus secretion. Representative types of neurokinin receptor antagonists and the disorders that can be treated with them include, for example, sleep, pain, migraine, emesis, nociception and inflammation, see, for example, U.S. Pat. Nos. 6,329,401, 5,760,018, 5,620,989, WO 95/19344, WO 94/13639, and WO 94/10165. Cyclobutyl heterocyclic compounds can be found in: WO 99/52848, WO 99/21824 and WO 98/57940.

It would be beneficial to provide a NK, antagonist that is potent, selective, and possesses beneficial therapeutic and pharmacological properties, and good metabolic stability. It would further be beneficial to provide a $NK_1$ antagonist that is effective for treating a variety of physiological disorders, symptoms and diseases, while minimizing side effects. This invention provides such $NK_1$ antagonists.

SUMMARY OF THE INVENTION

This invention is directed to compounds of formula (I):

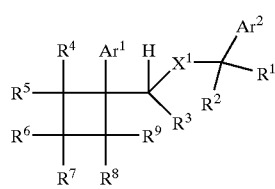

or the pharmaceutically-acceptable salts or solvates thereof, wherein:

$Ar^1$ and $Ar^2$ are each independently selected from the group consisting of:

(a) heteroaryl, (b) heteroaryl substituted with $(R^{21})_r$, and (c)

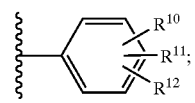

$X^1$ is selected from the group consisting of —O—, —S—, —SO—, —SO$_2$—, —NR$^{20}$—, —N(COR$^{20}$)— and —N(SO$_2$R$^{17}$)—; and when $X^1$ is selected from the group consisting of —SO—, —SO$_2$—, —N(COR$^{20}$)— and —N(SO$_2$R$^{17}$)—, then $R^1$ and $R^2$ are each independently selected from the group consisting of H, $C_1$-$C_6$ alkyl, hydroxy($C_1$-$C_3$ alkyl)-, $C_3$-$C_8$ cycloalkyl, —CH$_2$F, —CHF$_2$ and —CF$_3$; or $R^1$ and $R^2$, together with the carbon atom to which they are both attached, form a $C_3$-$C_6$ cycloalkyl ring; and when $X^1$ is selected from the group consisting of —O—, —S— and —NR$^{20}$—, then $R^1$ and $R^2$ are each independently selected from the group consisting of H, $C_1$-$C_6$ alkyl, hydroxy($C_1$-$C_3$ alkyl)-, $C_3$-$C_8$ cycloalkyl, —CH$_2$F, —CHF$_2$ and —CF$_3$; or $R^1$ and $R^2$, together with the carbon atom to which they are both attached, form a $C_3$-$C_6$ cycloalkyl group; or $R^1$ and $R^2$, together with the carbon atom to which they are both attached, form a —C(=O) group;

$R^3$ is selected from the group consisting of H, $C_1$-$C_6$ alkyl, hydroxy($C_1$-$C_3$ alkyl)-, $C_3$-$C_8$ cycloalkyl, —CH$_2$F, —CHF$_2$ and —CF$_3$;

$R^4$ and $R^5$ are each independently selected from the group consisting of H, $C_1$-$C_6$ alkyl-, -halogen, —OR$^{20}$, —O—C(O)NR$^{15}$R$^{16}$, —NR$^{15}$R$^{16}$, —NR$^{15}$SO$_2$R$^{17}$, —NR$^{15}$C(O)R$^{14}$, —NR$^{20}$C(O)NR$^{15}$R$^{16}$ and —SR$^{20}$; or $R^4$ and $R^5$, together with the carbon atom to which they are both attached, form a —C(=O)— or —C(=NR$^{13}$)— group;

$R^6$ is —(CH$_2$)$_{n1}$-G wherein $n_1$ is 0 to 5, wherein G is selected from the group consisting of: H, —OH, —O—($C_1$-$C_6$ alkyl), —O—($C_3$-$C_8$ cycloalkyl), —O—C(O)NR$^{15}$R$^{16}$, —NR$^{15}$R$^{16}$, —NR$^{15}$SO$_2$R$^{17}$, —NR$^{15}$C(O)R$^{14}$, —NR$^{20}$C(O)NR$^{15}$R$^{16}$, —C(O)NR$^{15}$R$^{16}$, —C(O)OR$^{20}$, —$C_3$-$C_8$ cycloalkyl,

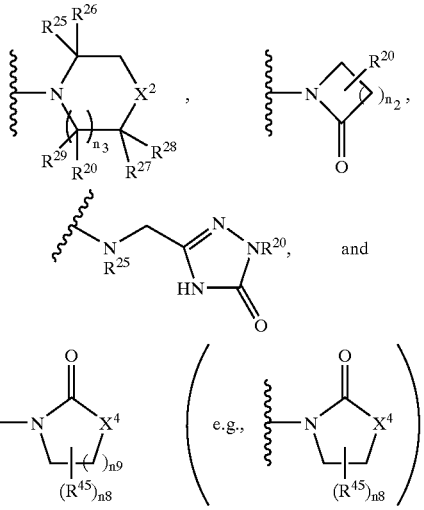

and $X^4$ is selected from the group consisting of —O—, —S—, and

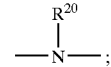

$R^7$ is —(CR$^{40}$R$^{41}$)$_{n6}$-J wherein $R^{40}$ and $R^{41}$ are each independently selected from the group consisting of H and —$C_1$-$C_2$ alkyl, and $n_6$ is 0 to 5, and J is selected from the group consisting of —H, —CF$_3$, —CHF$_2$, —CH$_2$F, —OH, —O—($C_1$-$C_6$ alkyl), —SO$_2$R$^{15}$, —O—($C_3$-$C_8$ cycloalkyl), —O—C(O)NR$^{15}$R$^{16}$, —NR$^{15}$R$^{16}$, —SO$_2$NR$^{15}$R$^{16}$, —NR$^{15}$SO$_2$R$^{17}$, —NR$^{15}$C(O)R$^{14}$, —NR$^{20}$C(O)NR$^{15}$R$^{16}$, —C(O)NR$^{15}$R$^{16}$, —C(O)OR$^{20}$, $C_3$-$C_8$ cycloalkyl,

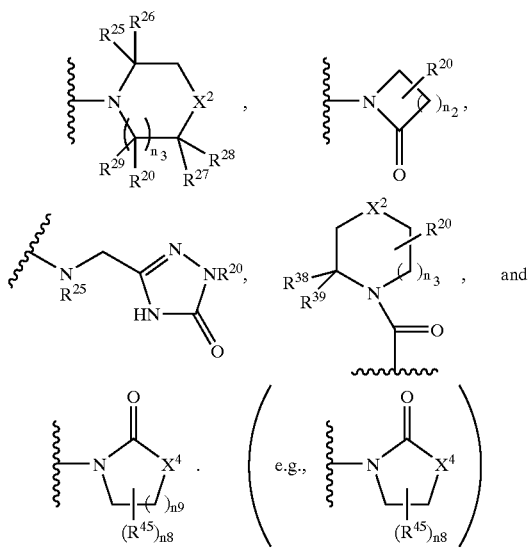

(examples of $R^7$ include, but are not limited to, $-(CH_2)_{n6}$-J and $-C(CH_3)_2$-J);

provided that:

(a) when $R^6$ is $-(CH_2)_{n1}$-G, where $n_1$ is 0, then G is selected from the group consisting of: $-OH$, $-O-(C_1-C_6$ alkyl), $-O-(C_3-C_8$ cycloalkyl), $-O-C(O)NR^{15}R^{16}$, $-NR^{15}R^{16}$, $-NR^{15}SO_2R^{17}$, $-NR^{15}C(O)R^{14}$, $-NR^{20}C(O)NR^{15}R^{16}$,

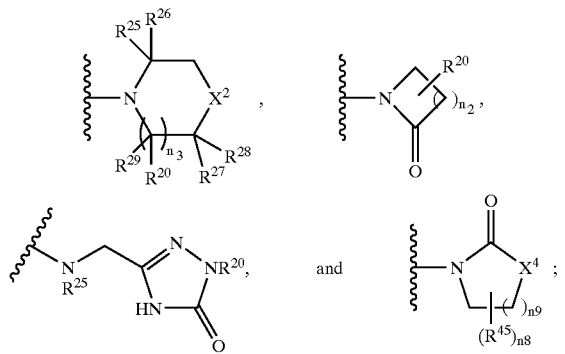

and (b) $R^7$ is $-(CR^{40}R^{41})_{n6}$-J, wherein $n_6$ is 0, then J is selected from the group consisting of $-H$, $-CF_3$, $-CHF_2$, $-CH_2F$, $-C(O)NR^{15}R^{16}$, $-C(O)OR^{20}$, and

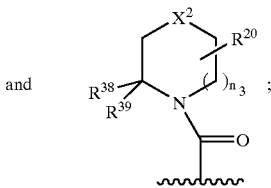

and (c) when $n_1$ for $R^6$ is 0, and $n_6$ for $R^7$ is 0, and one of $R^6$ and $R^7$ bound through a heteroatom (e.g., O or N) to the ring carbon of the cyclobutane ring then the other of $R^6$ and $R^7$ is bound through a carbon atom to the ring carbon of the cyclobutane ring (i.e., only one of $R^6$ or $R^7$ can be bound through a heteroatom to the carbon atom of the cyclobutane ring, i.e., the ring carbon atom to which $R^6$ and $R^7$ are bound does not have two heteroatoms bound to said ring carbon); or $R^6$ and $R^7$, together with the carbon atom to which they are both attached, form a $-C(=O)-$, $-C(=CH_2)-$, or $-C(=NR^{13})-$ group; or $R^6$ and $R^7$, taken together with the carbon atom to which they are bound, form:

(a) a 4- to 7-membered carbon ring (e.g., a $C_4$ to $C_7$ cycloalkyl ring);

(b) a 4- to 7-membered heterocycloalkyl ring; or (c) a 4 to 7-membered heterocycloalkenyl ring;

wherein said heterocycloalkyl or said heterocycloalkenyl comprises from 1 to 4 heteroatoms independently selected from the group consisting of: $-O-$, $-S-$, $-S(O)-$, $-SO_2-$, $-N=$, and $-NR^{20}-$ (wherein $R^{20}$ is defined below), provided that a ring $-S-$ in said heterocycloalkyl and said heterocycloalkenyl rings is not bound to another ring $-S-$ or ring $-S(O)-$ or ring $-O-$, and provided that a ring $-O-$ in said heterocycloalkyl and said heterocycloalkenyl rings is not bound to another ring $-O-$; said 4- to 7-membered rings being optionally substituted with from 1 to 4 $R^{45}$ substituents wherein each $R^{45}$ substituent is independently selected;

$R^8$ and $R^9$ are each independently selected from the group consisting of H, $C_1-C_6$ alkyl-, halogen, $-OR^{20}$, $-O-C(O)NR^{15}R^{16}$, $-NR^{15}R^{16}$, $-NR^{15}SO_2R^{17}$, $-NR^{15}C(O)R^{14}$, $-NR^{20}C(O)NR^{15}R^{16}$ and $-SR^{20}$; or $R^8$ and $R^9$, taken together with the carbon atom to which they are both attached, form a $-C(=O)-$ group;

$R^{10}$, $R^{11}$ and $R^{12}$ are each independently selected from the group consisting of H, $C_1-C_6$ alkyl, $C_3-C_8$ cycloalkyl, $-OR^{20}$, halogen, $-CN$, $-NO_2$, $-CF_3$, $-CHF_2$, $-CH_2F$, $-CH_2CF_3$, $-OCF_3$, $-OCHF_2$, $-OCH_2F$, $-OCH_2CF_3$, $-C(O)OR^{20}$, $-C(O)NR^{23}R^{24}$, $-NR^{23}C(O)R^{20}$, $-NR^{23}CO_2R^{17}$, $-NR^{23}C(O)NR^{23}R^{24}$, $-NR^{23}SO_2R^{17}$, $-NR^{23}R^{24}$, $-SO_2NR^{23}R^{24}$, $-S(O)_{n5}R^{17}$, aryl, aryl substituted with $(R^{21})_r$ wherein each $R^{21}$ substituent is independently selected, heteroaryl, and heteroaryl substituted with $(R^{21})_r$ wherein each $R^{21}$ substituent is independently selected;

each $R^{13}$ is independently selected from the group consisting of $-OH$ and $-O-(C_1-C_6$ alkyl);

each $R^{14}$ is independently selected from the group consisting of H, $C_1-C_6$ alkyl, $C_3-C_8$ cycloalkyl, $-C_1-C_6$ alkylNH$_2$ and $-C_1-C_6$ alkylNHC(O)OC$_1-C_6$alkyl;

$R^{15}$ and $R^{16}$ are each independently selected from the group consisting of H, benzyl, $C_1-C_6$ alkyl, and $C_3-C_8$ cycloalkyl; or $R^{15}$ and $R^{16}$, together with the nitrogen atom to which they are both attached, form a 4- to 7-membered ring that is optionally substituted with $-OR^{20}$, and wherein one of the carbon atoms in said 4- to 7-membered ring is optionally replaced by a heteroatom selected from the group consisting of $-O-$, $-S-$ and $-NR^{20}-$;

each $R^{17}$ is independently selected from the group consisting of $C_1-C_6$ alkyl, $C_3-C_8$ cycloalkyl and $-CF_3$;

each $R^{20}$ is independently selected from the group consisting of H, $C_1-C_6$ alkyl, $C_3-C_8$ cycloalkyl, $-(C_1-C_6)$alkylNH$_2$ (e.g., $-CH_2CH_2NH_2$), $(C_1-C_6)$alkoxy$(C_2-C_6)$alkyl, and hydroxy$(C_2-C_6)$alkyl;

each $R^{21}$ is a substituent on the aryl or heteroaryl ring to which it is attached and is independently selected from the group consisting of $C_1-C_6$ alkyl, $C_3-C_8$ cycloalkyl, $-OH$, -halogen, $-CN$, $-NO_2$, $-CF_3$, $-CHF_2$, $-CH_2F$, $-OCF_3$, $-OCHF_2$, $-OCH_2F$, $-O-(C_1-C_6$ alkyl), $-O-(C_3-C_8$ cycloalkyl), $-C(O)OR^{20}$, $-C(O)NR^{23}R^{24}$, —NR$^{23}$R$^{24}$, —NR$^{23}$C(O)R$^{20}$, —NR$^{23}$CO$_2$R$^{20}$, —NR$^{23}$C(O)NR$^{23}$R$^{24}$, —NR$^{23}$SO$_2$R$^{17}$ and —S(O)$_{n5}$R$^{17}$;

R$^{22}$ is selected from the group consisting of H, C$_1$–C$_6$ alkyl, C$_3$–C$_8$ cycloalkyl and —(CH$_2$)$_{n4}$-heterocycloalkyl;

R$^{23}$ and R$^{24}$ are each independently selected from the group consisting of H, C$_1$–C$_6$ alkyl, C$_3$–C$_8$ cycloalkyl and benzyl; or R$^{23}$ and R$^{24}$, together with the nitrogen atom to which they are both attached, form a 4- to 7-membered ring that is optionally substituted with —OR$^{20}$, where one of the carbon atoms in the ring is optionally replaced by a heteroatom selected from the group consisting of —O—, —S— and —NR$^{20}$—;

R$^{25}$ and R$^{26}$ are each independently selected from the group consisting of H and C$_1$–C$_6$ alkyl; or R$^{25}$ and R$^{26}$, together with the carbon atom to which they are both attached, form a —C(=O)— or cyclopropyl group;

R$^{27}$ and R$^{28}$ are each independently selected from the group consisting of H and C$_1$–C$_6$ alkyl; or R$^{27}$ and R$^{28}$, together with the carbon atom to which they are both attached, form a —C(=O)— or cyclopropyl group;

each R$^{29}$ is independently selected from the group consisting of H, C$_1$–C$_6$ alkyl and C$_3$–C$_8$ cycloalkyl;

R$^{30}$ and R$^{31}$ are each independently selected from the group consisting of H, C$_1$–C$_6$ alkyl (e.g., C$_1$–C$_2$ alkyl), —CH$_2$F, —CHF$_2$, —CF$_3$, —OH, and —O(C$_1$ to C$_3$)alkyl; or R$^{30}$ and R$^{31}$, together with the carbon atom to which they are both attached, form a —C(=O)— group;

R$^{38}$ and R$^{39}$ are each independently selected from the group consisting of H and C$_1$–C$_6$ alkyl; or R$^{38}$ and R$^{39}$, together with the carbon atom to which they are both attached, form a cyclopropyl group;

each R$^{45}$ is independently selected from the group consisting of: C$_1$–C$_6$ alkyl (e.g., C$_1$–C$_2$ alkyl), —CH$_2$F, —CHF$_2$, —CF$_3$, —OH, and —O(C$_1$ to C$_3$)alkyl; or two R$^{45}$ substituents, together with the carbon atom to which they are both attached, form a —C(=O)— group;

X$^2$ is selected from the group consisting of —CH$_2$—, —NR$^{22}$—, —N(C(O)NR$^{15}$R$^{16}$)—, —N(CO$_2$R$^{15}$)—, —N(SO$_2$R$^{17}$)—, —N(C(O)R$^{20}$)—, —N(SO$_2$NHR$^{20}$)—, —O—, —S—, —S(O)—, —SO$_2$—, —CF$_2$— and —CR$^{20}$F—;

r is from 1 to 3;
n$_2$ is from 1 to 4;
n$_3$ is from 0 to 2;
n$_4$ is from 0 to 3;
n$_5$ is from 0 to 2;
n$_8$ is from 0 to 4; and
n$_9$ is from 1 to 3;

provided that, when n$_3$ is 0, and R$^{27}$ and R$^{28}$ are each H, then X$^2$ is selected from the group consisting of —CH$_2$—, —S(O)—, —SO$_2$—, —CF$_2$— and —CR$^{20}$F—.

This invention is also directed to a pharmaceutical composition comprising an effective amount of at least one (e.g., one) compound of formula (I) and a pharmaceutically acceptable carrier.

This invention is also directed to a method for effecting an NK$_1$ receptor in a patient comprising administering to said patient an effective amount of at least one (e.g., one) compound of formula (I).

This invention is also directed to a method for treating an NK$_1$ receptor mediated disease (i.e., a disease associated with an NK$_1$ receptor, or a disease involving an NK$_1$ receptor in part of the disease process) in a patient in need of such treatment comprising administering to said patient an effective amount of at least one (e.g., one) compound of formula (I).

This invention is also directed to a method of treating a disease (or disorder or condition) in a patient in need of such treatment, wherein said disease is selected from the group consisting of: respiratory diseases (e.g., chronic lung disease, bronchitis, pneumonia, asthma, allergy, cough and bronchospasm), inflammatory diseases (e.g., arthritis and psoriasis), skin disorders (e.g., atopic dermatitis and contact dermatitis), ophthalmological disorders (e.g., retinitis, ocular hypertension and cataracts), central nervous system conditions, such as depressions (e.g., neurotic depression), anxieties (e.g., general anxiety, social anxiety and panic anxiety disorders), phobias (e.g., social phobia), and bipolar disorder, addictions (e.g., alcohol dependence and psychoactive substance abuse), epilepsy, nociception, psychosis, schizophrenia, Alzheimer's disease, AID's related dementia, Towne's disease, stress related disorders (e.g., post tramautic stress disorder), obsessive/compulsive disorders, eating disorders (e.g., bulimia, anorexia nervosa and binge eating), sleep disorders, mania, premenstrual syndrome, gastrointestinal disorders (e.g., irritable bowel syndrome, Crohn's disease, colitis, and emesis), atherosclerosis, fibrosing disorders (e.g., pulmonary fibrosis), obesity, Type II diabetes, pain related disorders (e.g., headaches, such as migraines, neuropathic pain, post-operative pain, and chronic pain syndromes), bladder and genitourinary disorders (e.g., interstitial cystitis and urinary incontinence), emesis (e.g., chemotherapy-induced (e.g., cisplatin, doxorubicin, and taxane), radiation-induced, motion sickness, ethanol-induced, and post operative nausea and vomiting), and nausea, comprising administering to said patient an effective amount of at least one (e.g., one) compound of formula (I).

This invention is also directed to a method of treating a disease (or disorder or condition) in a patient in need of such treatment, wherein said disease is selected from the group consisting of: respiratory diseases (e.g., cough), depression, anxiety, phobia, and bipolar disorder, alcohol dependence, psychoactive substance abuse, nociception, psychosis, schizophrenia, stress related disorders, obsessive/compulsive disorder, bulemia, anorexia nervosa and binge eating, sleep disorders, mania, premenstrual syndrome, gastrointestinal disorders, obesity, pain related disorders, bladder disorders, genitourinary disorders, emesis and nausea, comprising administering to said patient an effective amount of at least one (e.g., one) compound of formula (I).

This invention is also directed to a method of treating a disease wherein there is microvascular leakage and mucus secretion in a patient in need of such treatment, comprising administering to said patient an effective amount of at least one (e.g., one) compound of formula (I).

This invention is also directed to a method of treating asthma, emesis, nausea, depressions, anxieties, cough and pain related disorders in a patient in need of such treatment comprising administering to said patient an effective amount of at least one (e.g., one) compound of formula (I).

This invention is also directed to a method of treating emesis, depression, anxiety and cough in a patient in need of such treatment comprising administering to said patient an effective amount of at least one (e.g., one) compound of formula (I).

This invention is also directed to a method for antagonizing an effect of a Substance P at a neurokinin-1 receptor site in a patient in need of such treatment, comprising administering to said patient at least one (e.g., one) compound of formula (I).

This invention is also directed to a method for the blockade of neurokinin-1 receptors in a patient in need of such treatment, comprising administering to said patient at least one (e.g., one) compound of formula (I).

This invention is also directed to a method for treating depression and/or anxiety in a patient in need of such treatment comprising administering to said patient an effective amount of one or more (e.g., one) compounds of formula (I) in combination with an effective amount of one or more (e.g., one) anti-depressant agents and/or one or more (e.g., one) anti-anxiety agents.

This invention is also directed to a method of treating an $NK_1$ receptor mediated disease in a patient in need of such treatment comprising administering to said patient an effective amount of one or more (e.g., one) compounds of formula (I) in combination with an effective amount of one or more (e.g., one) selective serotonin reuptake inhibitors ("SSRIs").

This invention is also directed to a method of treating depression and/or anxiety in a patient in need of such treatment comprising administering to said patient an effective amount of one or more (e.g., one) compounds of formula (I) in combination with an effective amount of one or more (e.g., one) selective serotonin reuptake inhibitors.

This invention is also directed to a method of treating an $NK_1$ receptor mediated disease in a patient in need of such treatment comprising administering to said patient an effective amount of at least one (e.g., one) compound of formula (I) in combination with at least one (e.g., one) therapeutic agent selected from the group consisting of: other types of $NK_1$ receptor antagonists (e.g., those that are disclosed in the neurokinin receptor antagonist patents cited in the above Background Section), prostanoids, $H_1$ receptor antagonists, α-adrenergic receptor agonists, dopamine receptor agonists, melanocortin receptor agonists, endothelin receptor antagonists, endothelin converting enzyme inhibitors, angiotensin II receptor antagonists, angiotensin converting enzyme inhibitors, neutral metalloendopeptidase inhibitors, $ET_A$ antagonists, renin inhibitors, serotonin 5-$HT_3$ receptor antagonists (e.g., ondansetron), serotonin 5-$HT_{2c}$ receptor agonists, nociceptin receptor agonists, glucocorticoids (e.g., dexamethasone), rho kinase inhibitors, potassium channel modulators and inhibitors of multi-drug resistance protein 5.

This invention is also directed to a method for treating an $NK_1$ mediated disease in a patient in need of such treatment comprising administering to said patient an effective amount of a compound of formula (I) in combination at least one (e.g., one) therapeutic agent selected from the group consisting of: prostanoids, such as prostaglandin $E_1$; α-adrenergic agonists, such as phentolamine mesylate; dopamine receptor agonists, such as apomorphine; angiotensin II antagonists, such as losartan, irbesartan, valsartan and candesartan; $ET_A$ antagonists, such as bosentan and ABT-627; serotonin 5-$HT_3$ receptor antagonists, such as ondansetron; and glucocorticoids, such as dexamethasone.

This invention is also directed to a method for treating an $NK_1$ mediated disease in a patient in need of such treatment comprising administering to said patient an effective amount of at least one (e.g., one) compound of formula (I) in combination with and effective amount of at least one (e.g., one) therapeutic agent selected from the group consisting of: other types of $NK_1$ receptor antagonists, SSRIs, dopamine receptor agonists, serotonin 5-$HT_3$ receptor antagonists, serotonin 5-$HT_{2c}$ receptor agonists, nociceptin receptor agonists, glucocorticoids and inhibitors of multi-drug resistance protein 5.

This invention is also directed to a method for treating emesis, nausea and/or vomiting in a patient in need of such treatment comprising administering to said patient an effective amount of at least one (e.g., one) compound of formula (I) in combination with and effective amount of at least one (e.g., one) serotonin 5-$HT_3$ receptor antagonist (e.g., ondansetron) and/or at least one glucocorticoid (e.g., dexamethasone).

DETAILED DESCRIPTION OF THE INVENTION

Unless indicated other wise, the following definitions apply throughout the specifications and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc.

Unless otherwise indicated, when a substituent can be present more than once in a formula, each selection for that substituent is made independently of any other selections (e.g., for $(R^{21})_r$ each $R^{21}$ substituent is independently selected).

"At least one", examples include 1–3, 1–2 or 1.

"Heteroatom" means a nitrogen, sulfur, or oxygen atom. Multiple heteroatoms in the same group may be the same or different.

"One or more", examples include 1–3, or 1–2 or 1.

"Patient" means a mammal, such as a human, and preferably a human.

"Alkyl" means an unsubstituted or substituted, straight or branched, hydrocarbon chain having, preferably, from one to twenty-four carbon atoms, more preferably, from one to twelve carbon atoms, and even more preferably, from one to six carbon atoms.

"Cycloalkyl" or "cycloalkane" means an unsubstituted or substituted, saturated, stable, non-aromatic, carbocyclic ring, having, preferably, from three to fifteen carbon atoms, more preferably, from three to eight carbon atoms, most preferably 5 to 6 carbon atoms. The cycloalkyl ring can be fused with one to two cycloalkyl, aromatic (e.g., a benzo-fused ring), heterocyclic or heteroaromatic rings. The cycloalkyl ring can be attached at any endocyclic carbon atom that results in a stable structure. Examples of cycloalkyl rings include cyclopropyl, cyclobutyl, cyclopentyl, cyclohexyl, cycloheptyl, and the like.

"Aryl" means a substituted or unsubstituted aromatic carbocyclic ring system comprising, for example, from one to two aromatic rings. The aryl moiety generally comprises from 6 to 14, preferably 6 to 10, carbon atoms with all available substitutable carbon atoms of the aryl moiety being intended as possible points of attachment. Representative examples include phenyl, tolyl, xylyl, cumenyl, naphthyl, tetrahydronaphthyl, indanyl, indenyl and the like. The carbocyclic ring can optionally be substituted with from one to five, preferably one to three, moieties, such as mono- through pentahalo, alkyl, trifluoromethyl, phenyl, hydroxy, alkoxy, phenoxy, amino, monoalkylamino, dialkylamino, and the like, said moieties being independently selected.

"Heteroaryl" means an aromatic ring system comprising, for example, one or two aromatic rings and at least one nitrogen, oxygen or sulfur hetero atom in an aromatic ring. The heteroaryl group typically comprises 5 to 10 ring atoms (e.g., 5–6 or 9–10). The heteroaryl groups can be unsubstituted or substituted with a one or more substituents, preferably, one to five substituents, more preferably, one, two or three substituents (e.g., mono- through pentahalo, alkyl, trifluoromethyl, phenyl, hydroxy, alkoxy, phenoxy, amino, monoalkylamino, dialkylamino, and the like). Representative heteroaryl (heteroaromatic) groups are pyridinyl, pyrimidinyl, pyrazinyl, pyridazinyl, furanyl, benzofuranyl, thienyl, benzothienyl, thiazolyl, thiadiazolyl, imidazolyl, pyrazolyl, triazolyl, isothiazolyl, benzothiazolyl, benzoxazolyl, oxazolyl, pyrrolyl, isoxazolyl, 1,3,5-triazinyl and indolyl groups.

"Heterocycloalkyl" means an unsubstituted or substituted, saturated, cyclic ring system comprising from three to fifteen ring atoms, preferably, from three to eight ring atoms, and comprising carbon atoms and at least one heteroatom as part of the ring.

"Heterocycloalkenyl" means an unsubstituted or substituted, non-aromatic cyclic ring system comprising at least one (e.g., one) double bond, said ring system comprising from three to fifteen ring atoms, preferably, from three to eight ring atoms, and comprising carbon atoms and at least one heteroatom as part of the ring, and comprising.

"Heterocyclic ring" or "heterocycle" means an unsubstituted or substituted, saturated, unsaturated or aromatic mono cyclic or polycyclic ring, comprising carbon atoms and one or more heteroatoms in the ring. Monocyclic rings preferably contain from three to eight atoms in the ring structure, most preferably, five to seven atoms. Polycyclic ring systems comprising two rings preferably comprise from six to sixteen atoms, most preferably, ten to twelve atoms. Polycyclic ring systems comprising three rings comprise, preferably, from thirteen to seventeen atoms, most preferably, fourteen to fifteen atoms. Each heterocyclic ring has at least one heteroatom. Unless otherwise stated, the heteroatoms are each independently selected from the group consisting of: nitrogen, sulfur and oxygen atoms.

"Carbocyclic ring" or "carbocycle" means an unsubstituted or substituted, saturated, unsaturated or aromatic (e.g., aryl) hydrocarbon ring. Carbocycles may be monocyclic or polycyclic. Monocyclic rings, preferably, contain from three to eight atoms, more preferably, five to seven atoms. Polycyclic rings having two rings, preferably, contain from six to sixteen atoms, more preferably, ten to twelve atoms, and those having three rings, preferably, contain from thirteen to seventeen atoms, more preferably, fourteen to fifteen atoms.

"Alkoxy" means an oxygen atom bonded to an alkyl group(-O-alkyl). Representative alkoxy groups include methoxy, ethoxy and isopropoxy groups.

"Hydroxyalkyl" means an alkyl group, as defined above, comprising at least one hydroxy substituent (-alkyl-OH). Additional substituents to the alkyl group may also be present. Representative hydroxyalkyl groups include hydroxymethyl, hydroxyethyl and hydroxypropyl groups.

"Halo," "halogen" or "halide" means a chloro, bromo, fluoro or iodo atom radical. Chlorides, bromides and fluorides are preferred halides.

"Sulfonyl" represents a group having the formula —S(O)$_2$—.

"Prodrug" represents compounds that are drug precursors which, following administration to a patient, release the drug in vivo via a chemical or physiological process (e.g., a prodrug on being brought to a physiological pH or through an enzyme action is converted to the desired drug form). A discussion of prodrugs is provided in T. Higuchi and V. Stella, *Pro-drugs as Novel Delivery Systems*, Vol. 14 of A.C.S. Symposium Series (1987), and in *Bioreversible Carriers in Drug Design*, E. B. Roche, ed., American Pharmaceutical Ass'n and Pergamon Press (1987), each of which is incorporated herein by reference thereto.

"Effective amount" means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, and the particular active ingredient(s) being employed, and like factors within the knowledge and expertise of the attending physician.

This invention is directed to compounds having the formula (I) or Ia (defined below), including any and all isomers, such as enantiomers, stereoisomers, diastereomers, rotomers, and tautomers, and prodrugs of the compounds having the formula (I) or (Ia), and the isomers thereof, and their corresponding salts, solvates (e.g., hydrates), esters, and the like.

The invention is also directed to pharmaceutical compositions comprising one or more compounds of formula (I) or (Ia) and one or more pharmaceutically acceptable excipients/carriers, or salts, solvates, and esters thereof.

The compounds of formula (I) or (Ia) can be useful for treating a variety of diseases, symptoms and physiological disorders, such as emesis, depression, anxiety and cough. Thus, the invention is also directed to methods of treating such types of diseases, symptoms and disorders by administering to a patient in need of such treatment an effective amount of a pharmaceutical composition comprising at least one compound having the formula (I) or (Ia) and at least one pharmaceutically acceptable excipient/carrier.

Another aspect of the invention is to provide a kit comprising separate containers in a single package, wherein the inventive pharmaceutical compounds, compositions and/or salts thereof are used in combination with pharmaceutically-acceptable carriers to treat a variety of physiological disorders, symptoms and diseases.

Compounds having the formula (I) or (Ia) can have at least one asymmetrical carbon atom. All isomers, including stereoisomers, diastereomers, enantiomers, tautomers and rotational isomers, are contemplated as being part of the invention. Prodrugs, salts, solvates, esters, etc., derived from the compounds having the formula (I) or (Ia), or precursors thereof, are also within the scope of the invention. The invention includes d- and l-isomers in pure form and in admixture, including racemic mixtures. Isomers can be prepared using conventional techniques, either by reacting optically pure or optically enriched starting materials or by separating isomers of a compound having the formula (I) or (Ia).

The inventive compounds can exist in unsolvated as well as solvated forms, including hydrated forms. In general, the solvated forms, with pharmaceutically-acceptable solvents, such as water, ethanol, and the like, are equivalent to the unsolvated forms for purposes of this invention.

The inventive compounds may form pharmaceutically-acceptable salts with organic and inorganic acids. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. The salts are prepared by contacting the free base forms with a sufficient amount of the desired acid to produce a salt in a conventional manner. The free base forms may be regenerated by treating the salt with a suitable dilute aqueous base solution, such as dilute aqueous sodium hydroxide, potassium carbonate, ammonia or sodium bicarbonate. The free base forms may differ somewhat from their respective salt forms in certain physical properties, such as solubility in polar solvents, but the salts are otherwise equivalent to their respective free base forms for purposes of the invention. Acidic compounds of the invention (e.g., those compounds which possess a carboxyl group) form pharmaceutically-acceptable salts with inorganic and organic bases. Representative examples of such types of salts are sodium, potassium, calcium, aluminum, gold and silver salts. Also included are salts formed with pharmaceutically-acceptable amines, such as ammonia, alkyl amines, hydroxyalkylamines, N-methylglucamine, and the like. Many such types of salts are known in the art, for example, those that are described in WO 87/05297, which is incorporated in its entirety by reference herein. Preferred cationic salts include alkali metal salts (e.g., sodium and potassium) and alkaline earth metal salts (e.g., magnesium and calcium). Preferred anionic salts include halide (e.g., chloride), acetate and phosphate salts.

For compounds of formula (I), n8 is preferably 0–2 and most preferably 0–1.

For compounds of formula (I), t is preferably 1–2.

For compounds of formula (I) $R^{30}$ and $R^{31}$ are preferably selected from the group consisting of: H, and $(C_1-C_6)$alkyl, and most preferably H and —$CH_3$.

For compounds of formula (I) $R^{45}$ is preferably selected from the group consisting of: H, and $(C_1-C_6)$alkyl, and most preferably H and —$CH_3$.

For compounds of formula (I) $R^{20}$ is preferably H in the substituent —$NR^{20}$—.

Examples of moieties formed as a result of $R^6$ and $R^7$ being taken together with the carbon atom to which they are bound include:

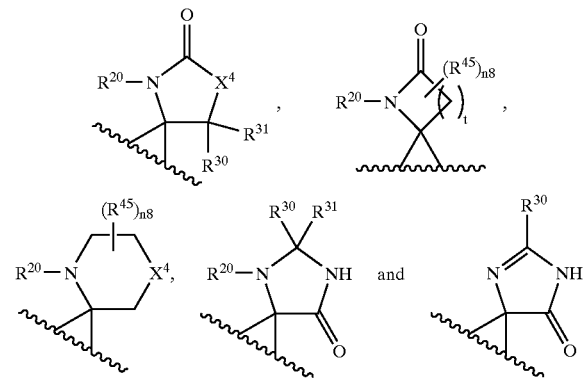

wherein t is from 1 to 4, and $X^4$ is selected from the group consisting of —O—, —S— or —$NR^{20}$— (wherein $R^{20}$, $R^{30}$, $R^{31}$, $R^{45}$, and $n_8$ are as defined for formula (I)).

Examples of moieties formed as a result of $R^6$ and $R^7$ being taken together with the carbon atom to which they are bound also include:

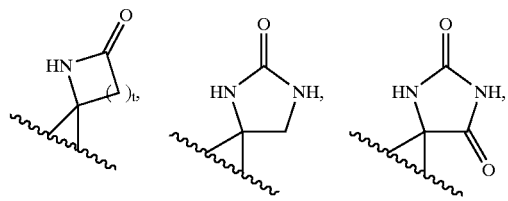

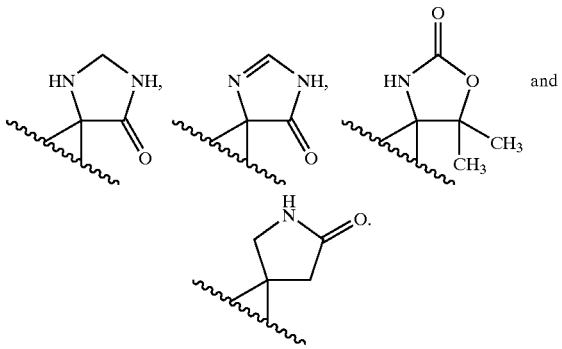

wherein t is 1 to 4.

One embodiment of the invention is directed to compounds wherein $R^6$ and $R^7$ taken together with the carbon atom to which they are bound form a ring selected from the group consisting of:

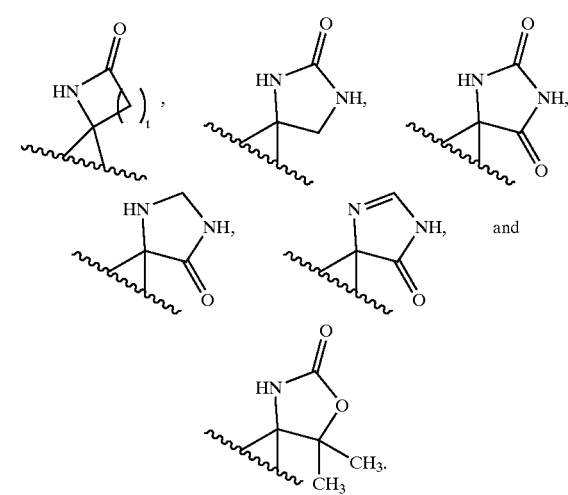

wherein t is 1 to 4.

One embodiment of the invention is directed to compounds of formula (I) wherein $R^6$ and $R^7$ taken together with the carbon to which they are bound form the ring:

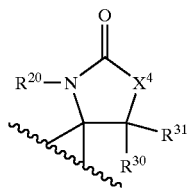

wherein $X^4$ is selected from the group consisting of: —O—, —S— and —$NR^{20}$—, and wherein $R^{20}$, $R^{30}$ and $R^{31}$ are as defined for formula (I).

One embodiment of the invention is directed to compounds of formula (I) wherein $R^6$ and $R^7$ taken together with the carbon to which they are bound form the ring:

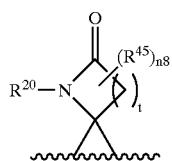

wherein t is 1–4, and $R^{20}$, $R^{45}$ and n8 are as defined for formula (I).

One embodiment of the invention is directed to compounds of formula (I) wherein $R^6$ and $R^7$ taken together with the carbon to which they are bound form the ring:

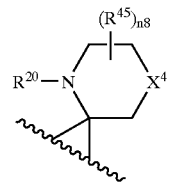

wherein $X^4$ is selected from the group consisting of: —O—, —S— and —$NR^{20}$—, and wherein $R^{20}$, $R^{45}$ and n8 are as defined for formula (I).

One embodiment of the invention is directed to compounds of formula (I) wherein $R^6$ and $R^7$ taken together with the carbon to which they are bound form the ring:

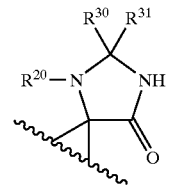

wherein $R^{20}$, $R^{30}$, and $R^{31}$ are as defined for formula (I).

One embodiment of the invention is directed to compounds of formula (I) wherein $R^6$ and $R^7$ taken together with the carbon to which they are bound form the ring:

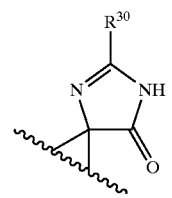

wherein $R^{30}$ is as defined for formula (I).

One embodiment of the invention is directed to compounds of formula (I) wherein $R^6$ and $R^7$ taken together with the carbon to which they are bound form the ring:

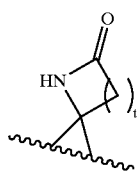

wherein t is 1 to 4.

One embodiment of the invention is directed to compounds of formula (I) wherein $R^6$ and $R^7$ taken together with the carbon to which they are bound form the ring:

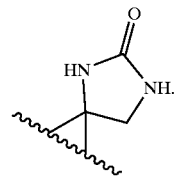

One embodiment of the invention is directed to compounds of formula (I) wherein $R^6$ and $R^7$ taken together with the carbon to which they are bound form the ring:

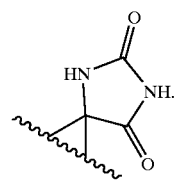

One embodiment of the invention is directed to compounds of formula (I) wherein $R^6$ and $R^7$ taken together with the carbon to which they are bound form the ring:

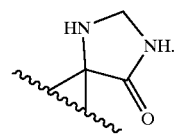

One embodiment of the invention is directed to compounds of formula (I) wherein $R^6$ and $R^7$ taken together with the carbon to which they are bound form the ring:

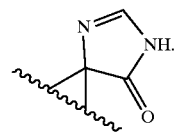

One embodiment of the invention is directed to compounds of formula (I) wherein $R^6$ and $R^7$ taken together with the carbon to which they are bound form the ring:

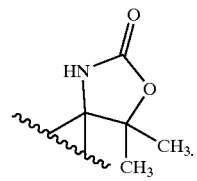

One embodiment of the invention is directed to compounds of formula (I) wherein $R^6$ and $R^7$ taken together with the carbon to which they are bound form the ring:

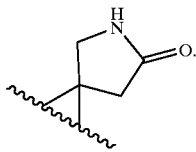

One embodiment of the invention is directed to compounds of formula (I) wherein $R^6$ or $R^7$ is

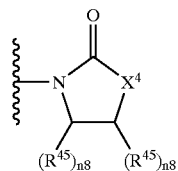

wherein n8 is 0–1 and $R^{45}$ is selected from the group consisting of —OH and —O($C_1$–$C_3$)alkyl, and all other substituents are as defined for formula (I).

One embodiment of the invention is directed to compounds of formula (I) wherein $R^6$ and $R^7$ together with the carbon to which they are bound form the ring

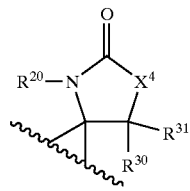

wherein $R^{30}$ is selected from the group consisting of —OH and —O($C_1$–$C_3$)alkyl, and $R^{31}$ is H, and all other substituents are as defined for formula (I).

One embodiment of the invention is directed to compounds of formula (I) wherein $R^4$ is H and $R^5$ is —OH, and all other substituents are as defined for formula (I).

One embodiment of the invention is directed to compounds of formula (I) wherein $R^6$ or $R^7$ is

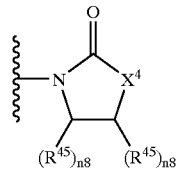

wherein n8 is 0–1, $R^{45}$ is selected from the group consisting of —OH and —O($C_1$–$C_3$)alkyl, $R^4$ is H and $R^5$ is —OH, and all other substituents are as defined for formula (I).

One embodiment of the invention is directed to compounds of formula (I) wherein $R^6$ and $R^7$ together with the carbon to which they are bound form the ring

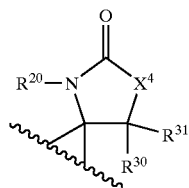

wherein $R^{30}$ is selected from the group consisting of —OH and —O($C_1$–$C_3$)alkyl, $R^{31}$ is H, $R^4$ is H and $R^5$ is —OH, and all other substituents are as defined for formula (I).

One embodiment of the invention is directed to compounds of formula (I) wherein $R^8$ is H and $R^9$ is —OH, and all other substituents are as defined for formula (I).

One embodiment of the invention is directed to compounds of formula (I) wherein $R^6$ or $R^7$ is

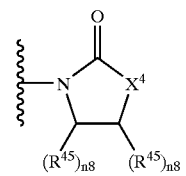

wherein n8 is 0–1, $R^{45}$ is selected from the group consisting of —OH and —O($C_1$–$C_3$)alkyl, $R^8$ is H and $R^9$ is —OH, and all other substituents are as defined for formula (I).

One embodiment of the invention is directed to compounds of formula (I) wherein $R^6$ and $R^7$ together with the carbon to which they are bound form the ring

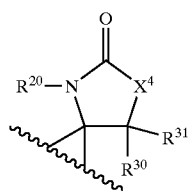

wherein $R^{30}$ is selected from the group consisting of —OH and —O($C_1$–$C_3$)alkyl, $R^{31}$ is H, $R^8$ is H and $R^9$ is —OH, and all other substituents are as defined for formula (I).

Preferred embodiments of this invention are directed to compounds of formula (I) comprising one of, or any two or more of, the groups of substituents defined in (1) to (7) below:

(1) $Ar^1$ and $Ar^2$ are each independently

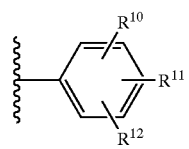

(i.e., Ar$^1$ and Ar$^2$ are the same or different

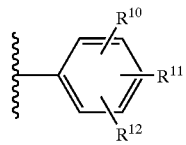

group)
wherein R$^{10}$, R$^{11}$ and R$^{12}$ are as defined for formula (1); more preferably, R$^{10}$, R$^{11}$ and R$^{12}$ are each independently selected from the group consisting of H, C$_1$–C$_6$ alkyl, C$_3$–C$_8$ cycloalkyl, —OR$^{20}$, halogen, —CN, —NO$_2$, —CF$_3$, —CHF$_2$, —CH$_2$F, —CH$_2$CF$_3$, —OCF$_3$, —OCHF$_2$, —OCH$_2$F, —OCH$_2$CF$_3$, heteroaryl, and heteroaryl substituted with (R$^{21}$)$_r$; even more preferably, R$^{10}$, R$^{11}$ and R$^{12}$ are each independently selected from the group consisting of H, C$_1$–C$_6$ alkyl, halogen, —CF$_3$, —CHF$_2$ and —CH$_2$F; and still more preferably, when X$^1$ is —O—, R$^{10}$, R$^{11}$ and R$^{12}$ are each independently selected from the group consisting of H, halogen, —CF$_3$, —OH, C$_1$–C$_6$alkyl, and —O(C$_1$–C$_6$) alkyl;

(2) X$^1$ is selected from the group consisting of —O— and —NR$^{20}$—; and more preferably X$^1$ is —O—;

(3) R$^1$ and R$^2$ are each independently selected from the group consisting of H, C$_1$–C$_6$ alkyl, hydroxy(C$_1$–C$_3$ alkyl)-, C$_3$–C$_8$ cycloalkyl, —CH$_2$F, —CHF$_2$ and —CF$_3$; more preferably R$^1$ and R$^2$ are each independently selected from the group consisting of H and C$_1$–C$_6$ alkyl; and even more preferably R$^1$ and R$^2$ are each independently selected from the group consisting of H and —CH$_3$;

(4) R$^3$ is selected from the group consisting of —H, C$_1$–C$_6$ alkyl, —CH$_2$F, —CHF$_2$ and —CF$_3$; more preferably R$^3$ is selected from the group consisting of H and C$_1$–C$_6$ alkyl; and even more preferably R$^3$ is H;

(5) R$^4$ and R$^5$ are each independently selected from the group consisting of H, C$_1$–C$_6$ alkyl. —OH and halogen (e.g., Cl); more preferably R$^4$ and R$^5$ are each independently selected from the group consisting of H and C$_1$–C$_6$ alkyl; and even more preferably R$^4$ and R$^5$ are each H;

(6) n$_1$ is 0, 1, or 2 for R$^6$, G for R$^6$ is selected from the group consisting of: H, —NR$^{15}$R$^{16}$, —NR$^{15}$SO$_2$R$^{17}$, —NR$^{15}$C(O)R$^{14}$, —NR$^{20}$C(O)NR$^{15}$R$^{16}$, —C(O)NR$^{15}$R$^{16}$, —C(O)OR$^{20}$, C$_3$–C$_8$ cycloalkyl,

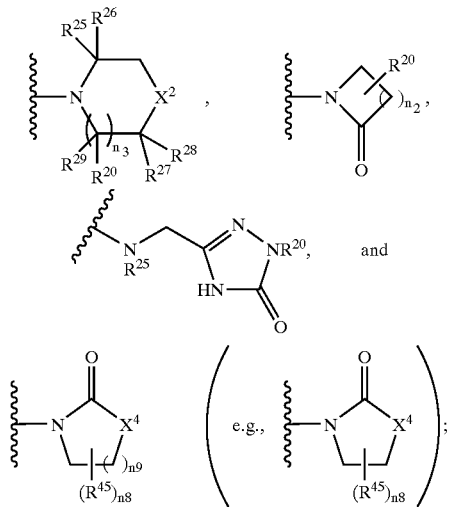

wherein R$^{14}$, R$^{15}$, R$^{16}$, R$^{17}$, R$^{20}$, R$^{25}$, R$^{26}$, R$^{27}$, R$^{28}$, R$^{29}$, X$^2$, R$^{45}$, n$_2$, n$_3$, and n$_8$ are as defined for formula (I); and (7) R$^7$ is —(CH$_2$)$_{n6}$-J (i.e., R$^{40}$ and R$^{41}$ are H) wherein n$_6$ is 0, 1 or 2, and J is selected from the group consisting of H, —CF$_3$, —CHF$_2$, —CH$_2$F, —NR$^{15}$R$^{16}$, —NR$^{15}$SO$_2$R$^{17}$, —NR$^{15}$C(O)R$^{14}$, —NR$^{20}$C(O)NR$^{15}$R$^{16}$, —C(O)NR$^{15}$R$^{16}$, —C(O)OR$^{20}$, C$_3$–C$_8$ cycloalkyl, —O—C(O)NR$^{15}$R$^{16}$,

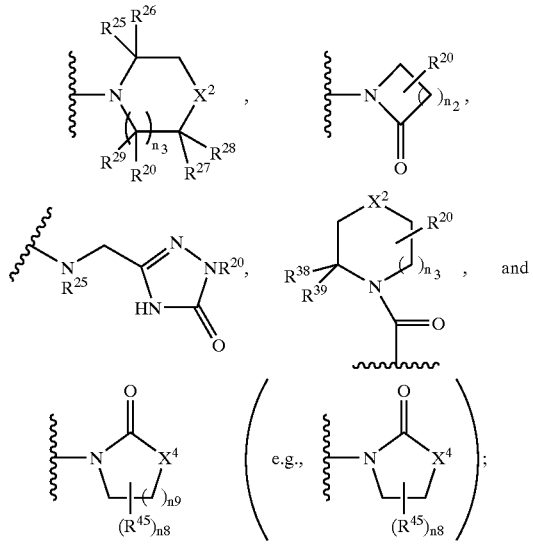

wherein R$^{14}$, R$^{15}$, R$^{16}$, R$^{17}$, R$^{20}$, R$^{25}$, R$^{26}$, R$^{27}$, R$^{28}$, R$^{29}$, X$^2$, R$^{45}$, n$_2$, n$_3$ and n$_8$ are as defined for formula (I).

In another preferred embodiment of the invention, R$^6$ and R$^7$, together with the carbon atom to which they are both attached, form a 4- to 7-membered ring comprising from, preferably, 0 to 2 heteroatoms that are each independently selected from the group consisting of —O—, —S—, —S(O)—, —SO$_2$—, —N= and —NR$^{20}$—, the 4- to 7-membered ring being optionally substituted with from 1 to 4 R$^{45}$ substituents wherein each R$^{45}$ substituent is independently selected. More preferably, the ring is selected from the group consisting of:

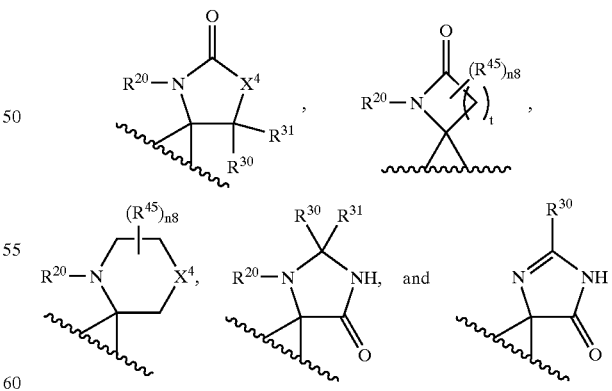

wherein t is 1 to 4, X$^4$ is selected from the group consisting of: —O—, —S—, and —NR$^{20}$—, and R$^{20}$, R$^{30}$, R$^{31}$, R$^{45}$, and n$_8$ are as defined for formula (I). Even more preferably the ring is selected from the group consisting of:

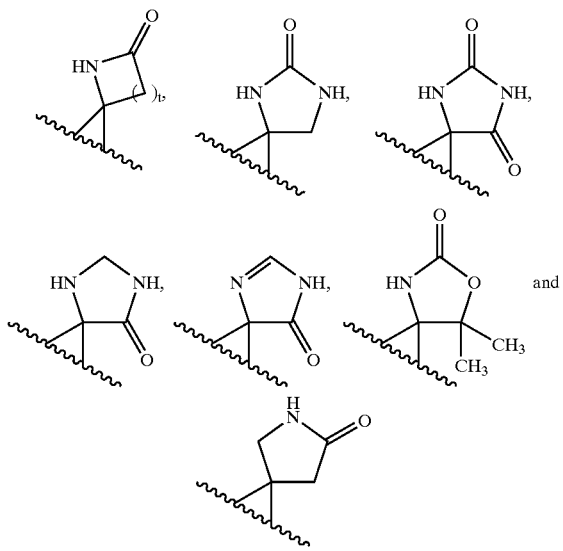

wherein t is 1 to 4. Still more preferably the ring is selected from the group consisting of:

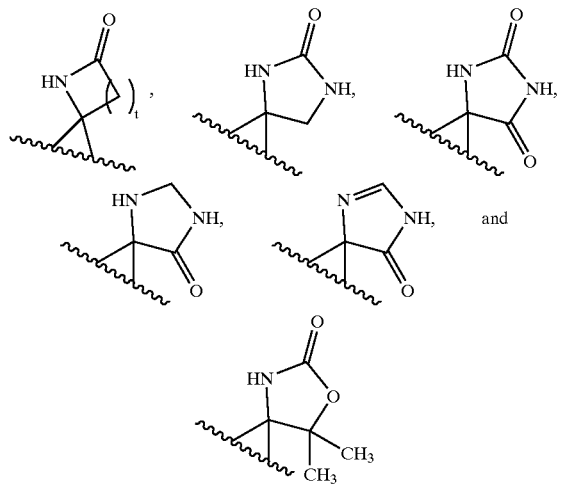

wherein t is 1 to 4.

In another preferred embodiment of the invention, $R^6$ is as defined for formula (I) (and most preferably n, for $R^6$ is 0 to 3, and $R^7$ is selected from the group consisting of —$NR^{15}R^{16}$ (e.g., —$NH_2$), —$NR^{15}C(O)R^{14}$ and —$NR^{20}C(O)NR^{15}R^{16}$, wherein $R^{14}$, $R^{15}$, $R^{16}$ and $R^{20}$ are as defined for formula(I). In still another preferred embodiment of the invention, $R^6$ is selected from the group consisting of —$CH_3$, —$CF_3$, —$CHF_2$, —$CH_2F$, —OH, —O—($C_1$-$C_6$ alkyl), —O—($C_3$-$C_8$ cycloalkyl), —$NR^{15}R^{16}$, —$NR^{15}C(O)R^{14}$, —$NR^{20}C(O)NR^{15}R^{16}$, —$C(O)NR^{15}R^{16}$ and —$C(O)OR^{20}$, wherein $R^{14}$, $R^{15}$, $R^{16}$ and $R^{20}$ are as defined for formula (I). In yet another preferred embodiment of the invention, $R^6$ and $R^7$, together with the carbon atom to which they are both attached, form a —C(=O)—, —C(=$CH_2$)—, or —C(=$NR^{13}$)— group.

Preferably $R^8$ and $R^9$ are each independently selected from the group consisting of H, —OH, $C_1$-$C_6$ alkyl and halogen (e.g., F or Cl), or $R^8$ and $R^9$, together with the carbon atom to which they are both attached, form a —C(=O)— group. More preferably, $R^8$ and $R^9$ are each independently selected from the group consisting of H and $C_1$-$C_6$ alkyl. Even more preferably, $R^8$ and $R^9$ are each H.

Preferably each $R^{13}$ is independently selected from the group consisting of —OH and —$OCH_3$.

Preferably each $R^{14}$ is independently selected from the group consisting of H, $C_1$-$C_6$ alkyl (e.g., methyl, ethyl, n-propyl, isopropyl, n-butyl, sec-butyl, tert-butyl, etc.), —$C_1$-$C_6$ alkyl$NH_2$ and —$C_1$-$C_6$ alkylNHC(O)O$C_1$-$C_6$ alkyl. More preferably, each $R^{14}$ is independently selected from the group consisting of H and —$CH_3$.

Preferably $R^{15}$ and $R^{16}$ are each independently selected from the group consisting of H, $C_1$-$C_6$ alkyl and $C_3$-$C_8$ cycloalkyl, or $R^{15}$ and $R^{16}$, together with the nitrogen atom to which they are both attached form a 4- to 7-membered ring that is optionally substituted with —$OR^{20}$, wherein one of the carbon atoms in the ring is optionally replaced by a heteroatom selected from the group consisting of —O—, —S— and —$NR^{20}$—, and wherein $R^{20}$ is as defined for formula (I). In one preferred embodiment of the invention, $R^{15}$ and $R^{16}$ are each independently selected from the group consisting of H and $CH_3$.

Preferably each $R^{17}$ is selected from the group consisting of $C_1$-$C_6$ alkyl and —$CF_3$. More preferably, each $R^{17}$ is $C_1$-$C_6$ alkyl (e.g., —$CH_3$).

Preferably each $R^{20}$ is independently selected from the group consisting of H and $C_1$-$C_6$ alkyl. More preferably, each $R^{20}$ is independently selected from the group consisting of H and —$CH_3$.

Preferably each $R^{21}$ is independently selected from the group consisting of H, $C_1$-$C_6$ alkyl, —$CF_3$, —$CHF_2$, —$CH_2F$, —$OCF_3$, —$OCHF_2$ and —$OCH_2F$. More preferably, each $R^{21}$ is selected from the group consisting of H and $C_1$-$C_6$ alkyl.

Preferably $R^{22}$ is selected from the group consisting of H and $C_1$-$C_6$ alkyl. More preferably, $R^{22}$ is selected from the group consisting of H and —$CH_3$.

Preferably $R^{23}$ and $R^{24}$ are each independently selected from the group consisting of H and $C_1$-$C_6$ alkyl. More preferably, $R^{23}$ and $R^{24}$ are each independently selected from the group consisting of H and —$CH_3$.

Preferably $R^{25}$ and $R^{26}$ are each independently selected from the group consisting of H and $C_1$-$C_6$ alkyl. More preferably, $R^{25}$ and $R^{26}$ are each independently selected from the group consisting of H and —$CH_3$.

Preferably $R^{27}$ and $R^{28}$ are each independently selected from the group consisting of H and $C_1$-$C_6$ alkyl. More preferably, $R^{27}$ and $R^{28}$ are each independently selected from the group consisting of H and —$CH_3$.

When $n_3$ is 0, and $R^{27}$ and $R^{28}$ are each H, and $n_3$ is 0, then $X^2$ is selected from the group consisting of —$CH_2$, —$CF_2$— and —$CR^{20}F$—, where $R^{20}$ is defined the same as above in the summary of the invention.

Preferably $R^{29}$ is selected from the group consisting of H and $C_1$-$C_6$ alkyl. More preferably $R^{29}$ is selected from the group consisting of H and —$CH_3$.

Preferably $R^{30}$ and $R^{31}$ are each independently selected from the group consisting of H and $C_1$-$C_2$ alkyl (e.g., —$CH_3$), or $R^{30}$ and $R^{31}$, together with the carbon atom to which they are both attached form a —C(=O)— group.

Preferably $R^{38}$ and $R^{39}$ are each independently selected from the group consisting of H and $C_1$-$C_2$ alkyl; or $R^{38}$ and $R^{39}$, together with the carbon atom to which they are both attached, form a cyclopropyl group.

Preferably each $R^{45}$ is independently a $C_1$-$C_2$ alkyl (e.g., —$CH_3$), or two $R^{45}$ substitutents, together with the carbon atom to which they are both attached, form a —C(=O)— group.

Preferably $X^2$ is selected from the group consisting of —$NR^{22}$, —O—, —S—, —S(O)—, —$SO_2$—, —$CH_2$—, —CF$_2$— and —CR$^{12}$F—. More preferably, X$^2$ is selected from the group consisting of —NR$^{22}$, —O— and —CH$_2$—.

Preferably r is 1 or 2, and more preferably 1.
Preferably n$_2$ is 2 or 3.
Preferably n$_3$ is 0, 1 or 2, and more preferably 1.
Preferably n$_4$ is 1, 2 or 3, and more preferably 1.
Preferably n$_5$ is 0 or 1.
Preferably n$_8$ is 0–2, and more preferably 0–1.

Preferred embodiments of the invention are also directed to compounds of formula (I) having one, or a combination of any two or more, of the groups of substituents defined in (1) to (8) below:

(1) X$^1$ is —O— or —NR$^{20}$—;
(2) Ar$^1$ and Ar$^2$ are each independently:

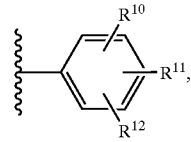

(i.e., Ar$^1$ and Ar$^2$ are the same or different

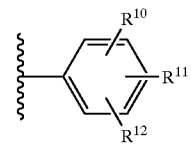

group)
wherein
(a) R$^{10}$, R$^{11}$ and R$^{12}$ are as defined for formula (I); or
(b) For Ar$^1$:
  (i) R$^{10}$, R$^{11}$ and R$^{12}$ are each H; or
  (ii) at least one (e.g., 1) of R$^{10}$, R$^{11}$ and R$^{12}$ is halogen, preferably, F; or
(c) For Ar$^2$:
  (i) at least two (e.g., 2) of R$^{10}$, R$^{11}$ and R$^{12}$ are each —CF$_3$; or
  (ii) at least two (e.g., 2) of R$^{10}$, R$^{11}$ and R$^{12}$ are each independently selected from the group consisting of F and Cl;
(3) (a) R$^1$ and R$^2$ are each independently selected from the group consisting of H and C$_1$–C$_6$ alkyl (e.g., —CH$_3$); or
(b) One of R$^1$ and R$^2$ is C$_1$–C$_6$ alkyl, preferably —CH$_3$;
(4) R$^3$ is H;
(5) (a) R$^4$ and R$^5$ are each H; or
(b) R$^4$ and R$^5$ are each Cl; or
(c) R$^4$ and R$^5$, together with the carbon atom to which they are both attached, form a —C(=O)— group;
(6) (a) R$^8$ and R$^9$ are each H; or
(b) R$^8$ and R$^9$, together with the carbon atom to which they are both attached, form a —C(=O)— group;
(7) (a) R$^6$ is —NH$_2$, and R$^7$ is selected from the group consisting of H, —CH$_3$, —C(O)NH$_2$, —C(O)NHCH$_3$, —C(O)N(CH$_3$)$_2$ and —C(O)OH;
(b) R$^6$ is —NH$_2$, and R$^7$ is selected from the group consisting of H, C$_1$–C$_6$alkyl (e.g., —CH$_3$, —CH$_2$CH$_3$, —CH$_2$CH$_2$CH$_3$, —CH$_2$CH$_2$CH$_2$CH$_3$, and —CH$_2$CH$_2$CH$_2$CH$_3$), —C(O)NR$^{15}$R$^{16}$ and —C(O)OR$^{20}$, wherein R$^{15}$, R$^{16}$ and R$^{20}$ are as defined for formula (I);
(c) R$^6$ is H, and R$^7$ is selected from the group consisting of —NH$_2$, —NHC(O)CH$_3$, —NHC(O)C(NH$_2$)(CH$_3$)$_2$,

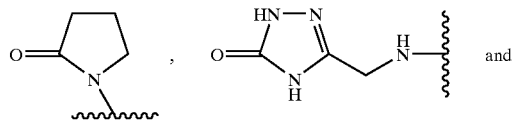

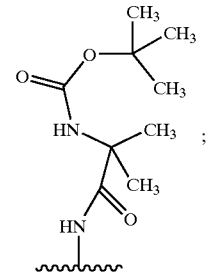

(d) R$^6$ is H, and R$^7$ is selected from the group consisting of —NR$^{15}$R$^{16}$, —NR$^{15}$C(O)R$^{14}$ and NR$^{20}$C(O)NR$^{15}$R$^{16}$, wherein R$^{14}$, R$^{15}$ and R$^{16}$ are as defined for formula (I);

(e) R$^6$ and R$^7$, together with the carbon atom to which they are both attached, form a 4- to 7-membered ring selected from the group consisting of:

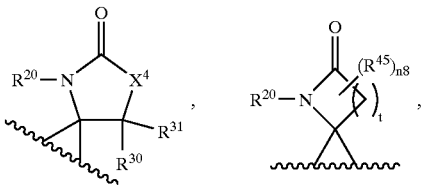

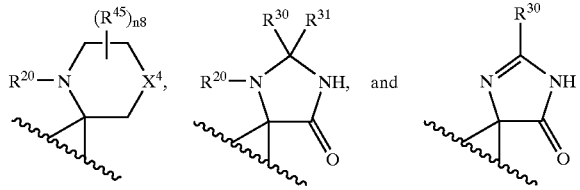

wherein t is from 1 to 4, X$^4$ is selected from the group consisting of: —O—, —S— and —NR$^{20}$—, and R$^{20}$, R$^{30}$, R$^{31}$, R$^{45}$ and n$_8$ are as defined for formula (I);

(f) R$^6$ and R$^7$, together with the carbon atom to which they are both attached, form a 4- to 7-membered ring selected from the group consisting of:

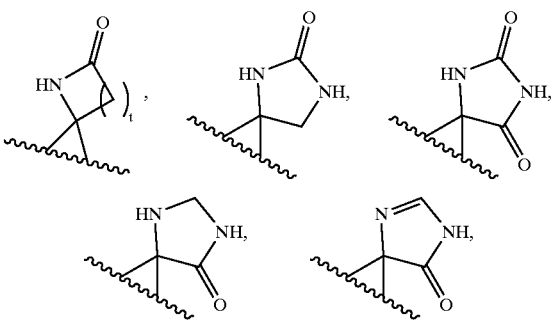

-continued

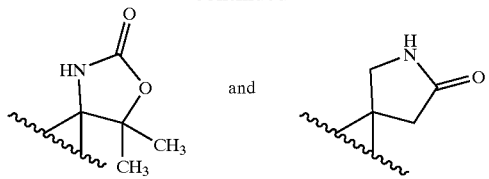

wherein t is from 1 to 4; or
(g) $R^6$ and $R^7$, together with the carbon atom to which they are both attached, form a 4- to 7-membered ring selected from the group consisting of:

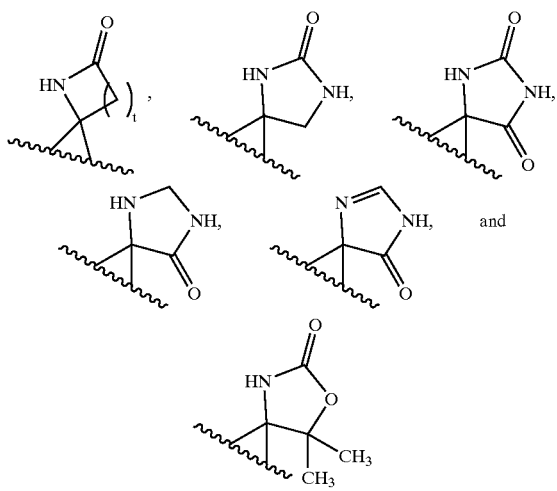

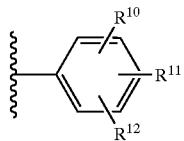

wherein t is from 1 to 4; and
(8) $X^1$ is —O— or —$NR^{20}$—;
$Ar^1$ and $Ar^2$ are each independently represented by the formula:

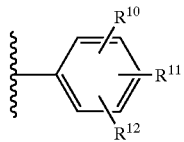

(i.e., $AR^1$ and $Ar^2$ are the same or different group)
wherein $R^{10}$, $R^{11}$ and $R^{12}$ are each independently selected from the group consisting of H, F, Cl, $C_1$–$C_6$ alkyl, —$CF_3$, —$CHF_2$, —$CH_2F$, —$OR^{20}$, —$OCF_3$, —$OCHF_2$, heteroaryl, and heteroaryl substituted with $(R^{21})_r$;
$R^1$ and $R^2$ are each independently selected from the group consisting of H, $C_1$–$C_6$ alkyl and hydroxy ($C_1$–$C_3$alkyl)-; or $R^1$ and $R^2$, together with the carbon atom to which they are both attached, form a —C(=O)— group;

$R^3$ is selected from the group consisting of H and $C_1$–$C_6$ alkyl;
$R^4$ and $R^5$ are each independently selected from the group consisting of H, —OH, $C_1$–$C_6$ alkyl and halogen; or $R^4$ and $R^5$, together with the carbon atom to which they are both attached, form a —C(=O)— group; and
$R^8$ and $R^9$ are each independently selected from the group consisting of H, —OH, $C_1$–$C_6$ alkyl and halogen; or $R^8$ and $R^9$, together with the carbon atom to which they are both attached, form a —C(=O)— group.

Another preferred embodiment of the invention is directed to a compound of formula (I) having formula (Ia):

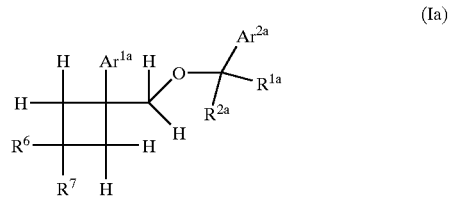

(Ia)

or pharmaceutically acceptable salts or solvates thereof, wherein:
$Ar^{1a}$ is represented by the following formula:

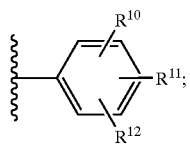

wherein $R^{10}$, $R^{11}$ and $R^{12}$ are each independently selected from the group consisting of H, halogen, —OH, —O($C_1$–$C_6$)alkyl, $C_1$–$C_6$alkyl and —$CF_3$ (preferably $R^{10}$, $R^{11}$ and $R^{12}$ are each H);
$Ar^{2a}$ is represented by the following formula:

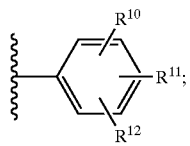

wherein $R^{10}$, $R^{11}$ and $R^{12}$ are independently selected from the group consisting of: H, $C_1$–$C_6$ alkyl, $C_3$–$C_8$ cycloalkyl, —$OR^{20}$ (wherein $R^{20}$ is as defined for formula (I)), halogen, —CN, —$NO_2$, —$CF_3$, —$CHF_2$, —$CH_2F$, —$CH_2CF_3$, —$OCF_3$, —$OCHF_2$, —$OCH_2F$, —$OCH_2CF_3$, heteroaryl, and heteroaryl substituted with $(R^{21})_r$ wherein each $R^{21}$ substituent is independently selected and $R^{21}$ is as defined for formula (I) (preferably $R^{10}$, $R^{11}$ and $R^{12}$ are each independently selected from the group consisting of H, halogen, —OH, —O($C_1$–$C_6$)alkyl, $C_1$–$C_6$alkyl and —$CF_3$);
$R^{1a}$ and $R^{2a}$ are each independently selected from the group consisting of H, $C_1$–$C_6$ alkyl and hydroxy ($C_1$–$C_3$alkyl)-; and
$R^6$ and $R^7$ are as defined for formula (I).
$R^6$ is —$NR^{15}R^{16}$, and $R^7$ is selected from the group consisting of H, $C_1$–$C_6$ alkyl (e.g., —$CH_3$, —$CH_2CH_3$, —$CH_2CH_2CH_3$, —$CH_2CH_2CH_2CH_3$, and)- $CH_2CH_2CH_2CH_2CH_3$), —C(O)$NR^{15}R^{16}$ and —C(O)$OR^{20}$, wherein $R^{15}$, $R^{16}$ and $R^{20}$ are as defined for formula (I). More preferably, $R^6$ is —$NH_2$, and $R^7$ is selected from the group consisting of H, —$CH_3$, —$CH_2CH_3$, —$CH_2CH_2CH_3$, —CH$_2$CH$_2$CH$_2$CH$_3$, —CH$_2$CH$_2$CH$_2$CH$_2$CH$_3$, —C(O)NH$_2$, —C(O)NHCH$_3$, —C(O)N(CH$_3$)$_2$ and —C(O)OH. In another preferred embodiment, R$^6$ and R$^7$, together with the carbon atom to which they are both attached, form a 4- to 7-membered ring, and preferably a 4- to 7-membered ring having 0 to 2 heteroatoms, said ring being as defined for formula (I). More preferably, the 4- to 7-membered ring is selected from the group consisting of:

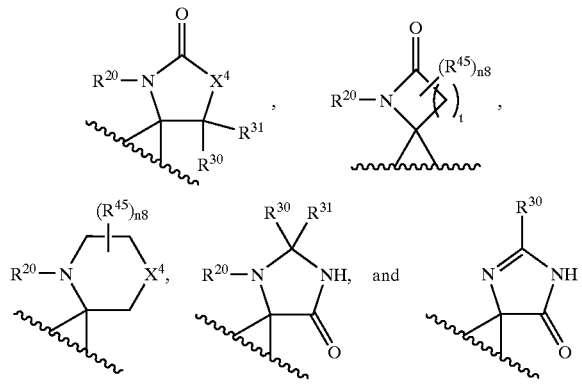

wherein t is from 1 to 4, X$^4$ is selected from the group consisting of: —O—, —S— and —NR$^{20}$—, and R$^{20}$, R$^{30}$, R$^{31}$, R$^{45}$ and n$_8$ are as defined for formula (I). Most preferably the 4- to 7-membered ring is selected from the group consisting of:

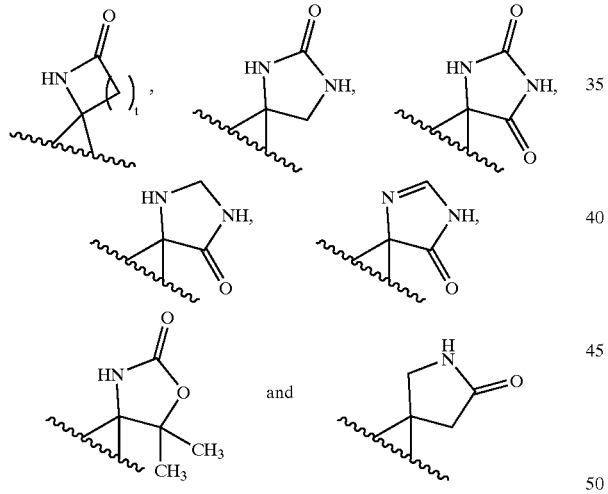

wherein t is 1 to 4. Still more preferably the ring is selected from the group consisting of:

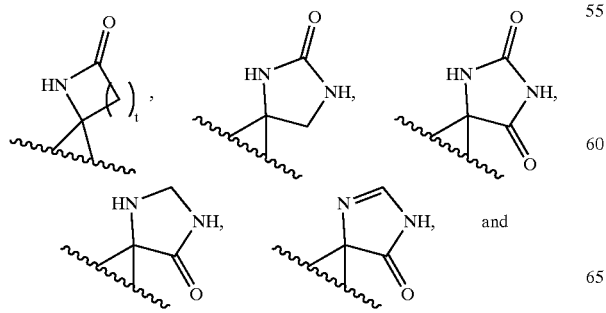

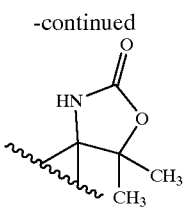

wherein t is 1 to 4.

Representative compounds of the invention include, but are not limited to, the compounds in Table I. In the structures in Table I, "Me" represents methyl.

TABLE I

| EXAMPLE | STRUCTURE |
|---|---|
| 1a | 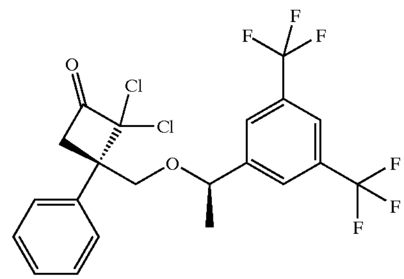 |
| 1b | 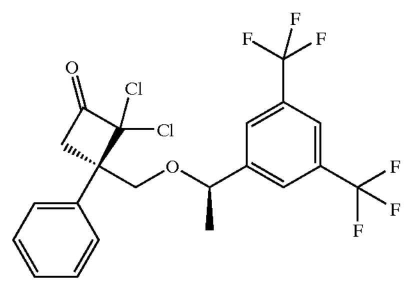 |
| 2 | 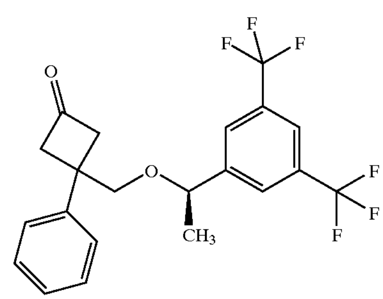 |
| 3 | 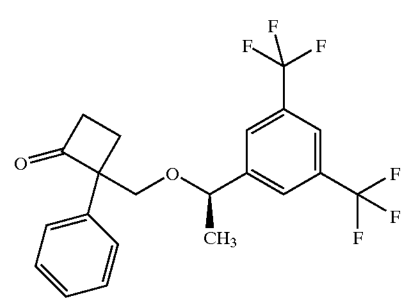 |

TABLE I-continued

| EXAMPLE | STRUCTURE |
|---|---|
| 4 | 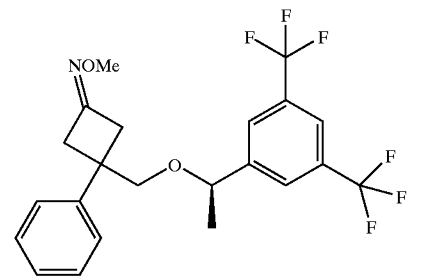 |
| 5 | 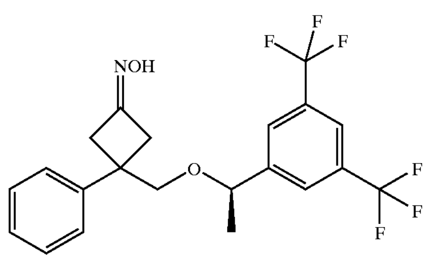 |
| 6 | 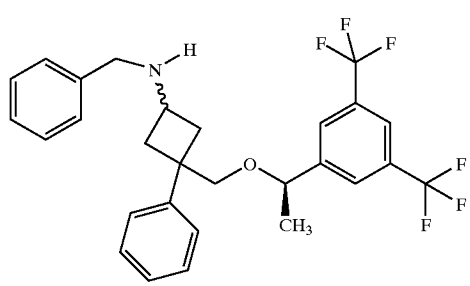 |
| 7 | 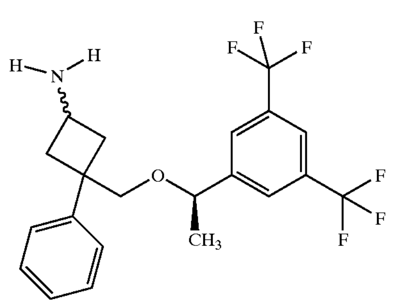 |
| 8a | 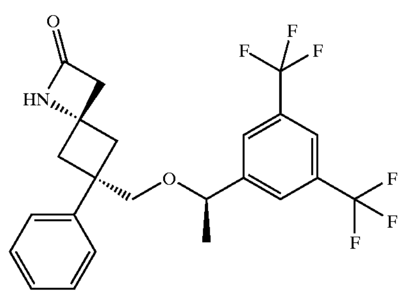 |
| 8b | |
| 9a | |
| 9b | |
| 9c | |
| 10a | |

TABLE I-continued
| EXAMPLE | STRUCTURE |
|---|---|
| 10b | 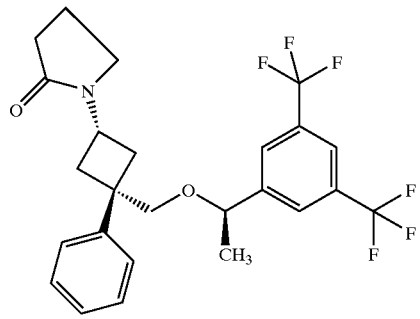 |
| 11a | 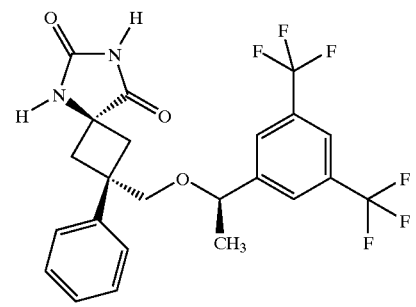 |
| 11b | 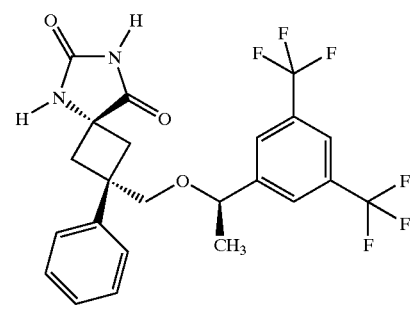 |
| 12a | 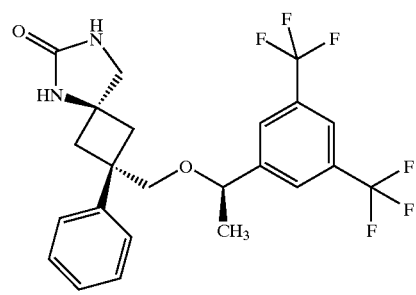 |
TABLE I-continued
| EXAMPLE | STRUCTURE |
|---|---|
| 12b | 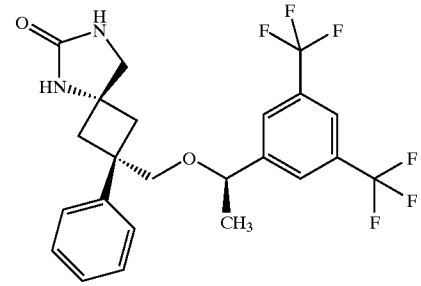 |
| 13 | 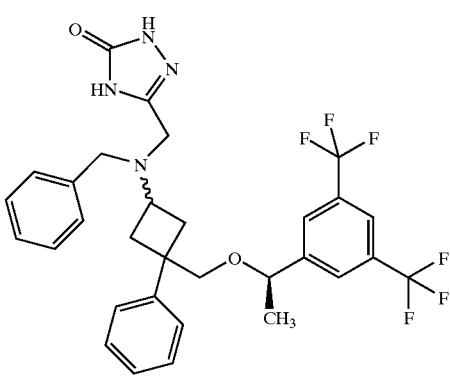 |
| 14 | 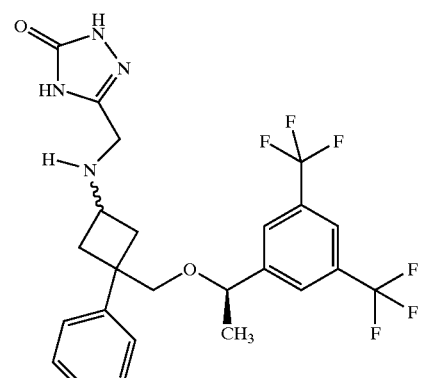 |
| 15a | 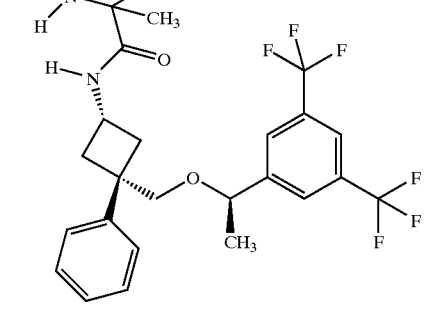 |

TABLE I-continued

| EXAMPLE | STRUCTURE |
|---|---|
| 15b | |
| 16a | |
| 16b | |
| 17a | |
| 17b | 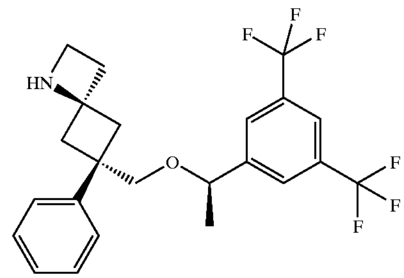 |
| 18 | 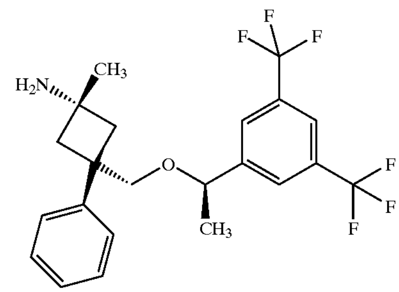 |
| 19 | 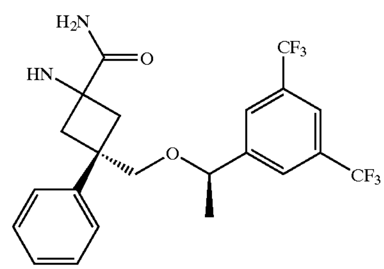 |
| 20 | 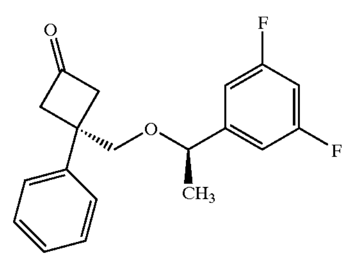 |
| 21a | 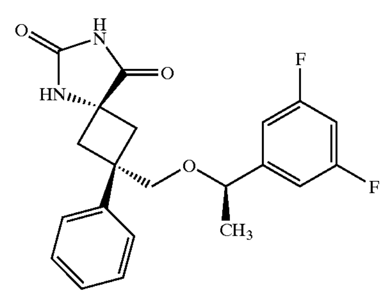 |

TABLE I-continued
| EXAMPLE | STRUCTURE |
|---|---|
| 21b | 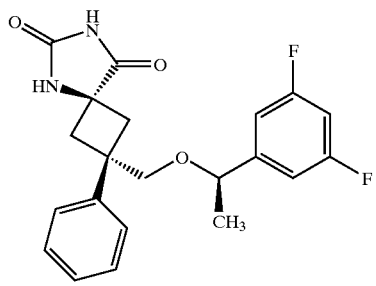 |
| 22a | 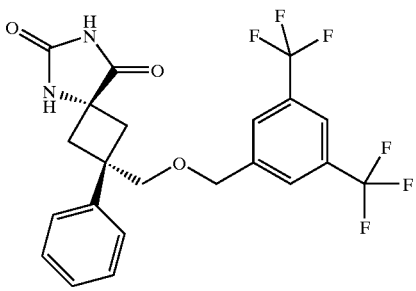 |
| 22b | 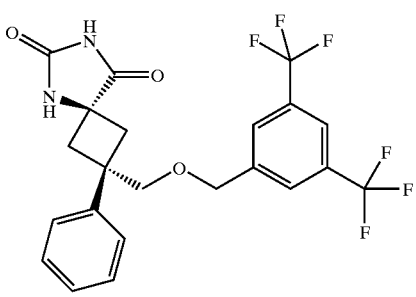 |
| 23a | 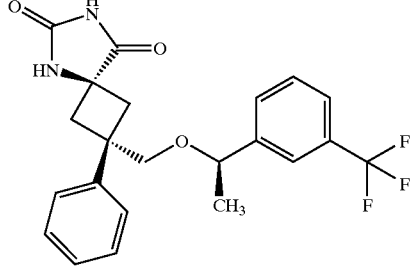 |
| 23b | 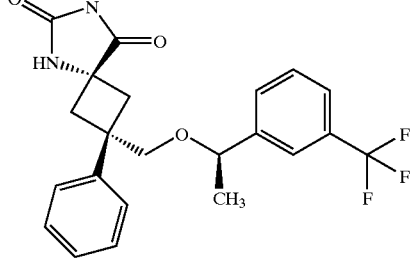 |
TABLE I-continued
| EXAMPLE | STRUCTURE |
|---|---|
| 24 | 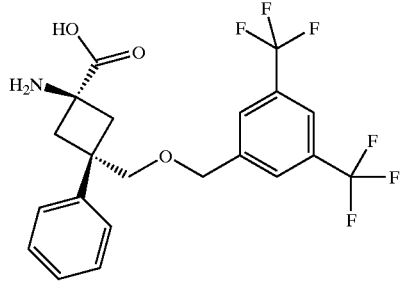 |
| 25 | 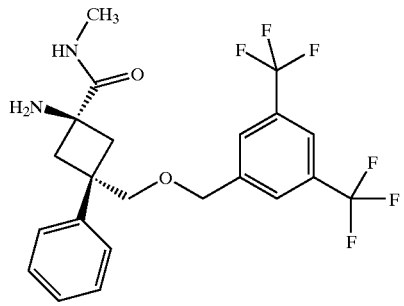 |
| 26a | 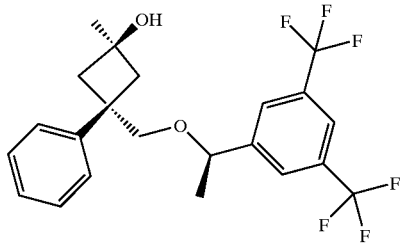 |
| 26b | 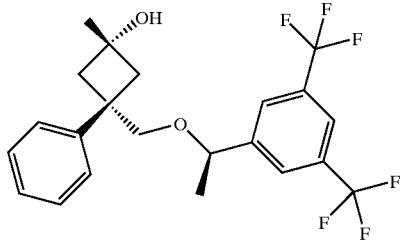 |
| 27 | 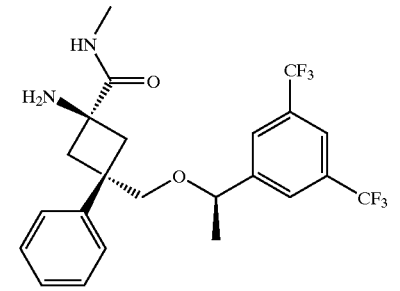 |

TABLE I-continued

| EXAMPLE | STRUCTURE |
|---|---|
| 28 | (1-amino-3-phenyl-3-{[(1R)-1-(3,5-bis(trifluoromethyl)phenyl)ethoxy]methyl}cyclobutyl)carboxamide |
| 29 | N,N-dimethyl variant of example 28 |
| 30 | pyrrolidinyl amide variant |
| 31 | piperidinyl amide variant |
| 32 | morpholinyl amide variant |
| 33 | N-methyl amide variant |
| 34 | carboxamide variant |
| 35 | hydroxymethyl variant |
| 36 | spiro-oxazolidinone variant |
| 37 | spiro-morpholinone variant |

TABLE I-continued
| EXAMPLE | STRUCTURE |
|---|---|
| 38 | 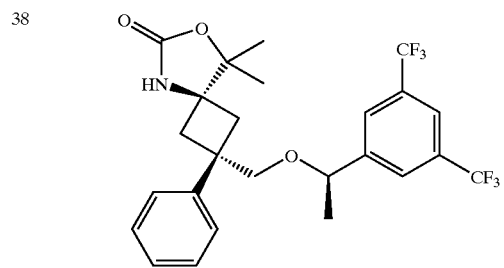 |
| 39 | 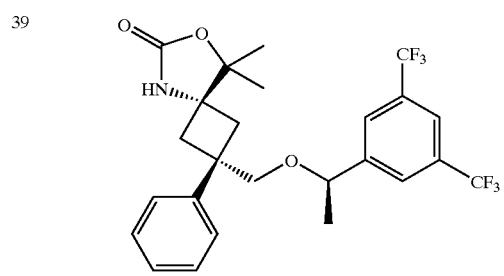 |
| 40 | 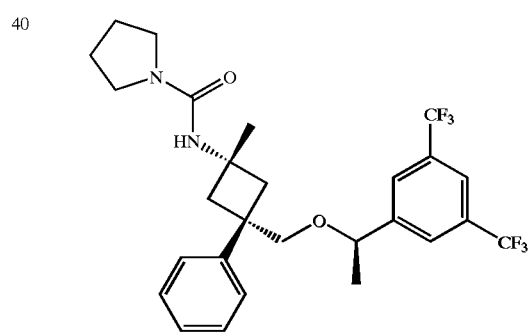 |
| 41 | 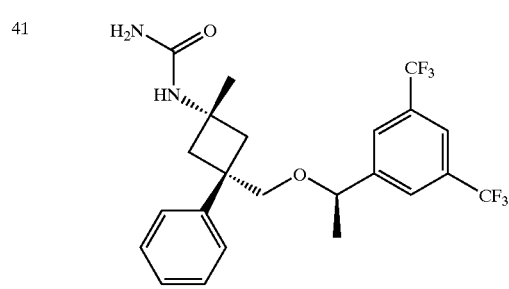 |
| 42 | 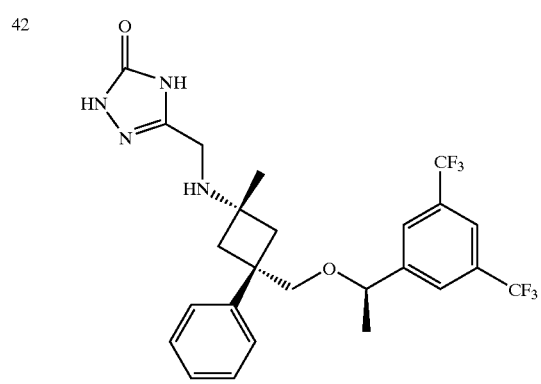 |
| 43 | 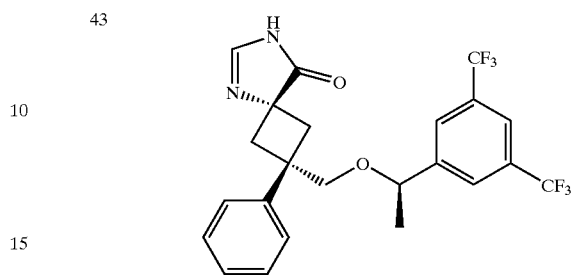 |
| 44 | 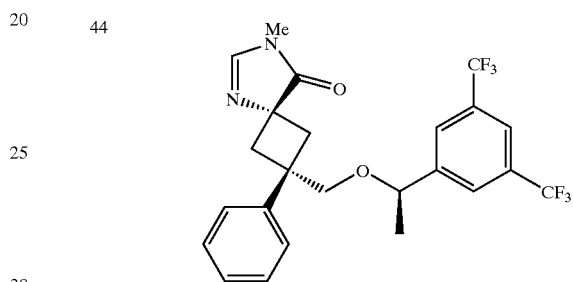 |
| 45 | 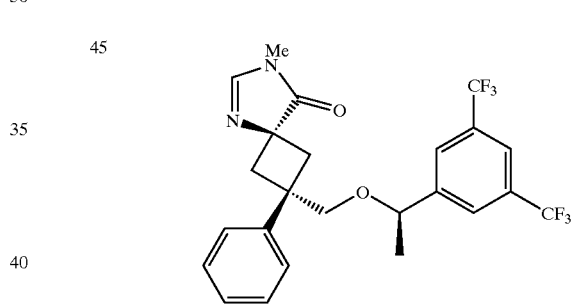 |
| 46 | 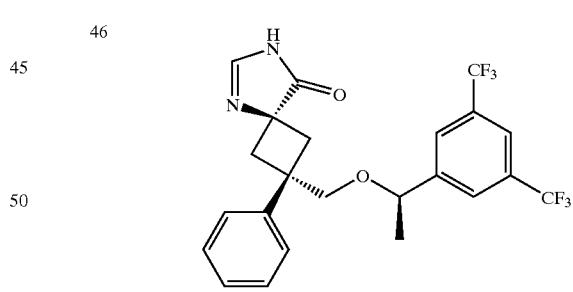 |
| 47 | 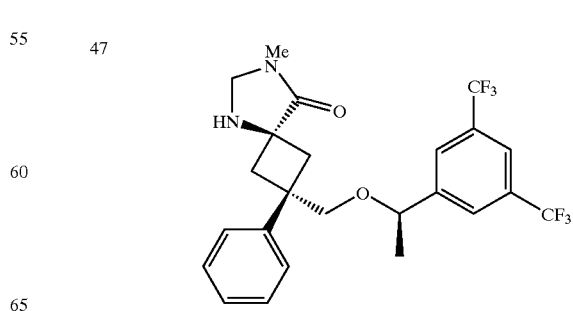 |

TABLE I-continued

| EXAMPLE | STRUCTURE |
|---------|-----------|
| 48 | 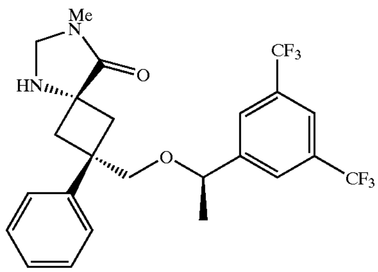 |
| 49 | 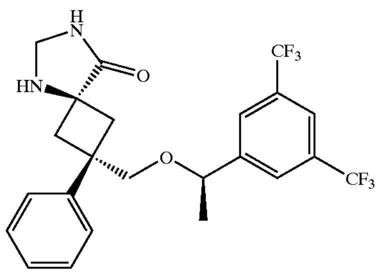 |
| 50 | 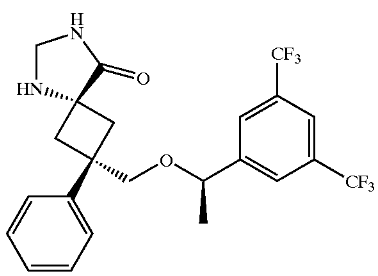 |
| 51 | 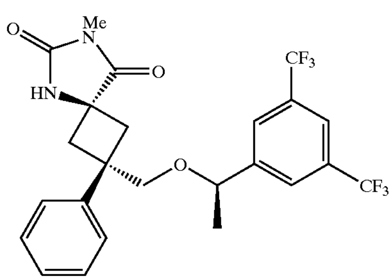 |
| 52 | 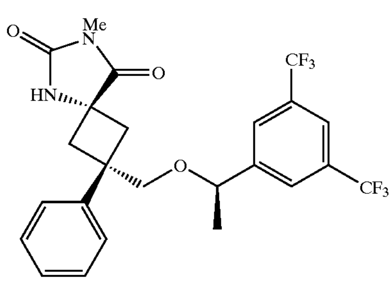 |
| 53 | |
| 54 | |
| 55 | |
| 56 | |
| 57 | |

TABLE I-continued

| EXAMPLE | STRUCTURE |
|---|---|
| 58 | 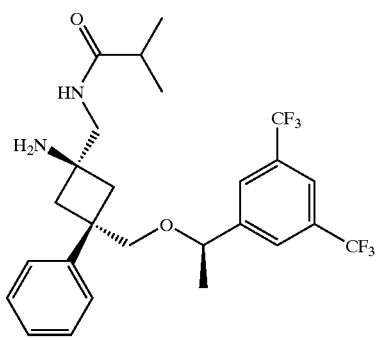 |
| 59 | 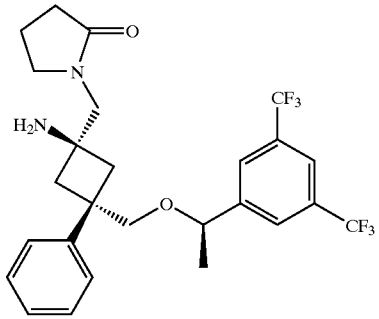 |
| 60 | 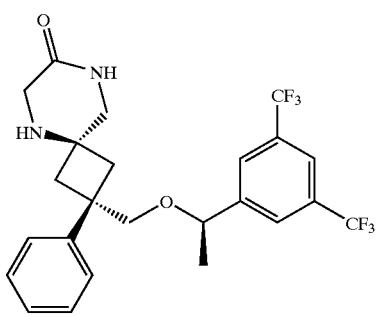 |
| 61 | 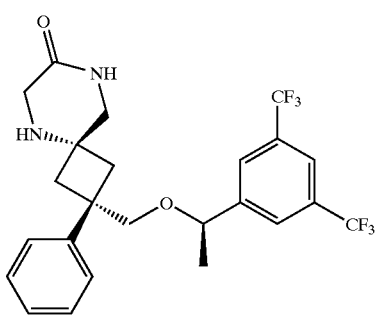 |
| 62 | 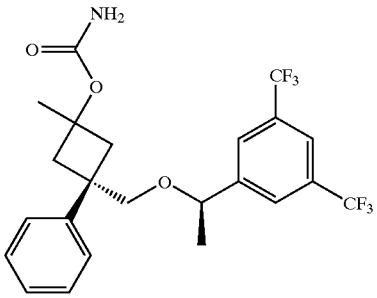 |
| 63a | 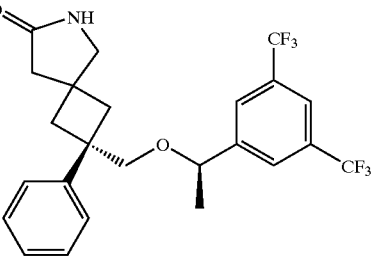 |
| 63b | 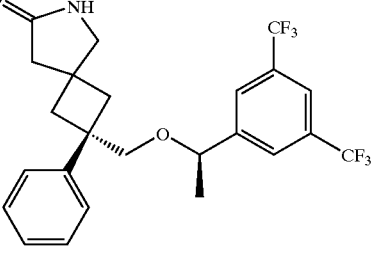 |
| 64 | 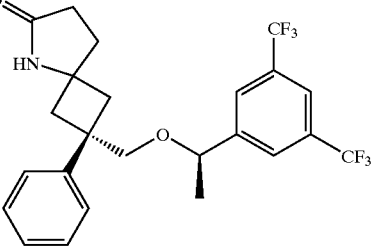 |

Preferred compounds of the invention are compounds of Examples 7, 8a, 8b, 9c, 10a, 11a, 11b, 12a, 12b, 14, 16b, 17a, 17b, 18, 26b, 27–36, 39, 43–54, 57, 63b, and 64 in Table I.

More preferred compounds of the invention are compounds of Examples 11a, 11b, 12a, 12b, 27–29, 39, 43, 44–50 in Table I.

Even more preferred compounds of the invention are compounds of Examples 11a, 11b, 12b, 27, 28, 46 and 49 in Table I.

Assay

The in vitro and in vivo $NK_1$, $NK_2$ and $NK_3$ activities of the compounds having the formulas (I) and (Ia) can be determined by various procedures known in the art, such as a test for their ability to inhibit the activity of the $NK_1$ agonist Substance P. The percent inhibition of neurokinin agonist activity is the difference between the percent of maximum specific binding ("MSB") and 100%. The percent of MSB is defined by the following equation, wherein "dpm" represents "disintegrations per minute":

$$\% \text{ MSB} = \frac{(\text{dpm of unknown}) - (\text{dpm of nonspecific binding})}{(\text{dpm of total binding}) - (\text{dpm of nonspecific binding})} \times 100.$$

The concentration at which a compound having the formula (I) or (Ia) produces 50% inhibition of binding is then used to determine an inhibition constant ("$K_i$") using the Chang-Prusoff equation.

The $K_i$ values can be determined following the procedure of Duffy, Ruth A. et al., "Correlation of Neurokinin (NK) 1 Receptor Occupancy in Gerbil Striatum with Behavioral Effects of NK1 Antagonists", J Pharmacol Exp Ther, 2002, 301:536–542, the disclosure of which is incorporated herein by reference thereto.

In vivo activity may be measured by inhibition of an agonist-induced foot tapping in a gerbil, as described in *Science*, 281, 1640–1695 (1998), the disclosure of which is incorporated herein by reference thereto.

The compounds of Examples 1a, 1b, 2–7, 8a, 8b, 9a, 9b, 9c, 10a, 10b, 11a, 11b, 12a, 12b, 13, 14, 15a, 15b, 16a, 16b, 17a, 17b, 18–20, 21a, 21b, 22a, 22b, 23a, 23b, 24, 25, 26a, 26b, 27–62, 63a, 63b, and 64 in Table I had a $K_i$ in the range of 0.02 to 93.20 nM The compounds of Examples 7, 8a, 8b, 9c, 10a, 11a, 11b, 12a, 12b, 14, 16b, 17a, 17b, 18, 26b, 27–36, 39, 43–54, 57, 63b, and 64 in Table I had a $K_i$ in the range of 0.02 to 5.32 nM.

The compounds of Examples 11a, 11b, 12a, 12b, 27–29, 39, 43, and 44–50 in Table I had a $K_i$ in the range of 0.11 to 5.32 nM.

The compounds of Examples 11a, 11b, 12b, 27, 28, 46 and 49 in Table I had a $K_i$ in the range of 0.13 to 1.78 nM.

The compound of Example 49 had a $K_i$ of 0.2 nM.

Compounds having the formula (I) or (Ia) can be effective antagonists of the $NK_1$ receptor, and of an effect of its endogenous agonist, Substance P, at the $NK_1$ receptor site, and therefore, can be useful in treating conditions caused or aggravated by the activity of said receptor Compounds having the formulas (I) or (Ia) have a number of utilities. For instance, the inventive compounds can be useful as antagonists of neurokinin receptors, particularly, $NK_1$ receptors in a mammal, such as a human. As such, they may be useful in treating and preventing one or more of a variety of mammalian (human and animal) disease states (physiological disorders, symptoms and diseases) in a patient in need of such treatment, for instance, respiratory diseases (e.g., chronic lung disease, bronchitis, pneumonia, asthma, allergy, cough and bronchospasm), inflammatory diseases (e.g., arthritis and psoriasis), skin disorders (e.g., atopic dermatitis and contact dermatitis), ophthalmalogical disorders (e.g., retinitis, ocular hypertension and cataracts), central nervous system conditions, such as depressions (e.g., neurotic depression), anxieties (e.g., general anxiety, social anxiety and panic anxiety disorders), phobias (e.g., social phobia), and bipolar disorder, addictions (e.g., alcohol dependence and psychoactive substance abuse), epilepsy, nociception, psychosis, schizophrenia, Alzheimer's disease, AIDs related dementia, Towne's disease, stress related disorders (e.g., post tramautic stress disorder), obsessive/ compulsive disorders, eating disorders (e.g., bulemia, anorexia nervosa and binge eating), sleep disorders, mania, premenstrual syndrome, gastrointestinal disorders (e.g., irritable bowel syndrome, Crohn's disease, colitis, and emesis), atherosclerosis, fibrosing disorders (e.g., pulmonary fibrosis), obesity, Type II diabetes, pain related disorders (e.g., headaches, such as migraines, neuropathic pain, postoperative pain, and chronic pain syndromes), bladder and genitourinary disorders (e.g., interstitial cystitis and urinary incontinence), and nausea.

Preferably, the inventive compounds can be useful in treating and preventing one of the following mammalian (e.g., human) disease states in a patient in need of such treatment: respiratory diseases (e.g., cough), depression, anxiety, phobia, and bipolar disorder, alcohol dependence, psychoactive substance abuse, nociception, psychosis, schizophrenia, stress related disorders, obsessive/ compulsive disorder, bulemia, anorexia nervosa and binge eating, sleep disorders, mania, premenstrual syndrome, gastrointestinal disorders, obesity, pain related disorders, bladder disorders, genitourinary disorders and nausea. In particular, the compounds having the formulas (I) and (Ia) are useful for treating disease states related to microvascular leakage and mucus secretion. Consequently, the compounds of the invention are especially useful in the treatment and prevention of asthma, emesis, nausea, depressions, anxieties, cough and pain related disorders, more especially, emesis, depression, anxiety and cough.

In another aspect, the invention relates to pharmaceutical compositions comprising at least one compound (e.g., one to three compounds, preferably, one compound) represented by the formula (I) or (Ia) and at least one pharmaceutically-acceptable excipient/carrier. The invention also relates to the use of such pharmaceutical compositions in the treatment of mammalian (e.g., human) disease states, such as those listed above.

In still another aspect of the invention, a method is provided for antagonizing an effect of a Substance P at a neurokinin-1 receptor site or for the blockade of one or more neurokinin-1 receptors in a mammal (i.e., a patient, e.g., a human) in need of such treatment, comprising administering to the mammal an effective amount of at least one (e.g., one) compound having the formula (I) or (Ia).

In another embodiment of the invention, an effective amount of one or more of the inventive $NK_1$ receptor antagonists may be combined with an effective amount of one or more anti-depressant agents and/or one or more anti-anxiety agents (e.g., gepirone (e.g., gepirone hydrochloride), and nefazodone (e.g., nefazodone hydrochloride, e.g., Serzone®) to treat depression and/or anxiety. U.S. Pat. No. 6,117,855 (2000) which is incorporated herein by reference thereto, discloses a method for treating or preventing depression or anxiety with a combination therapy of a specific $NK_1$ receptor antagonist together with an anti-depressant and/or anti-anxiety agent. Thus, anti-depressant and/or anti-anxiety agents, such as those disclosed in U.S. Pat. No. 6,117,855 (2000), can be combined with one or more (e.g., one) compounds having the formulas (I) and/or (Ia) to treat depression and/or anxiety disease states in a mammal, preferably, a human.

In still another embodiment of the invention, an effective amount of one or more (e.g., one) of the inventive $NK_1$ receptor antagonists may be combined with an effective amount of one or more (e.g., one) selective serotonin reuptake inhibitors ("SSRIs") to treat a variety of mammalian disease states, such as those described above. SSRIs alter the synaptic availability of serotonin through their inhibition of presynaptic reaccumulation of neuronally released serotonin. U.S. Pat. No. 6,162,805 (2000), which is incorporated herein by reference thereto, discloses a method for treating obesity with a combination therapy of a $NK_1$ receptor antagonist and an SSRI. An inventive compound(s) having the formula (I) or (Ia) can be combined together with an SSRI(s) in a single pharmaceutical composition, or it can be administered simultaneously, concurrently or sequentially with an SSRI. This combination may be useful in the treatment and prevention of obesity or another of the above-identified human and animal disease states. In particular, an effective amount of at least one (e.g., one) compound having the formula (I) or (Ia), alone or together with an effective amount of at least one (e.g., one) selective serotonin reuptake inhibitor, can be useful in the treatment and prevention of emesis, depression, anxiety and/or cough.

Numerous chemical substances are known to alter the synaptic availability of serotonin through their inhibition of presynaptic reaccumulation of neuronally released serotonin. Representative SSRIs include, without limitation, the following: fluoxetine (e.g., fluoxetine hydrochloride, e.g., Prozac®), fluvoxamine (e.g., fluvoxamine maleate, e.g. Luvox®), paroxetine (e.g., paroxetine hydrochloride, e.g., Paxil®), sertraline (e.g., sertraline hydrochloride, e.g., Zoloft®), citalopram (e.g., citalopram hydrobromide, e.g., Celexa™), duloxetine (e.g., duloxetine hydrochloride, e.g., and venlafaxine (e.g., venlafaxine hydrochloride, e.g., Effexor®). Further SSRIs include those disclosed in U.S. Pat. No. 6,162,805 (2000). Other compounds can readily be evaluated to determine their ability to selectively inhibit serotonin reuptake. Thus, one aspect of the invention relates to a pharmaceutical composition comprising at least one (e.g., one) $NK_1$ receptor antagonist having the formula (I) or (Ia), at least one (e.g., one) SSRI, and at least one pharmaceutically-acceptable excipient/carrier. Another aspect of the invention relates to a method of treating the above identified mammalian (e.g., human) disease states, the method comprising administering to a patient in need of such treatment an effective amount of a pharmaceutical composition comprising at least one (e.g., one) $NK_1$ receptor antagonist having the formula (I) or (Ia) in combination with at least one (e.g., one) SSRI, such as one of those recited above, and at least one pharmaceutically-acceptable excipient/carrier.

In a preferred aspect, the invention relates to a method of treating emesis, depression, anxiety and/or cough, the method comprising administering to a patient in need of such treatment an effective amount of at least one (e.g., one) $NK_1$ receptor antagonist having the formula (I) or (Ia) in combination with at least one (e.g., one) SSRI, such as one of those described above. When an inventive $NK_1$ receptor antagonist is combined with an SSRI for administration to a patient in need of such treatment, the two active ingredients can be administered simultaneously, consecutively (one after the other within a relatively short period of time), or sequentially (first one and then the other over a period of time). In general, when the two active ingredients are administered consecutively or sequentially, the inventive $NK_1$ receptor antagonist is, preferably, administered before the administration of the SSRI.

Thus, the compounds of the invention may be employed alone or in combination with other active agents. Combination therapy includes the administration of two or more active ingredients to a patient in need of treatment. In addition to the above described $NK_1$ receptor antagonist/SSRI combination therapy, the compounds having the formula (I) and (Ia) may be combined with one or more other active agents, such as the following: other types of $NK_1$ receptor antagonists (e.g., those that are disclosed in the neurokinin receptor antagonist patents cited above in the related art description section), prostanoids, $H_1$ receptor antagonists, α-adrenergic receptor agonists, dopamine receptor agonists, melanocortin receptor agonists, endothelin receptor antagonists, endothelin converting enzyme inhibitors, angiotensin II receptor antagonists, angiotensin converting enzyme inhibitors, neutral metalloendopeptidase inhibitors, $ET_A$ antagonists, renin inhibitors, serotonin 5-$HT_3$ receptor antagonists (e.g., ondansetron (e.g., ondansetron hydrochloride, e.g., Zolfran®), palonosetron and granisetron (e.g., granisetron hydrochloride, e.g., Kytril®)), serotonin 5-$HT_{2c}$ receptor agonists, nociceptin receptor agonists, glucocorticoids (e.g., dexamethasone), rho kinase inhibitors, potassium channel modulators and/or inhibitors of multi-drug resistance protein 5.

Preferable therapeutic agents for combination therapy with compounds of the invention are the following: prostanoids, such as prostaglandin $E_1$; α-adrenergic agonists, such as phentolamine mesylate; dopamine receptor agonists, such as apomorphine; angiotensin II antagonists, such as losartan, irbesartan, valsartan and candesartan; $ET_A$ antagonists, such as bosentan and ABT-627; serotonin 5-$HT_3$ receptor antagonists, such as ondansetron; and glucocorticoids, such as dexamethasone. In preferred embodiments of the invention, the inventive compounds can be combined with: other types of $NK_1$ receptor antagonists, SSRIs, dopamine receptor agonists, serotonin 5-$HT_3$ receptor antagonists, serotonin 5-$HT_{2c}$ receptor agonists, nociceptin receptor agonists, glucocorticoids and/or inhibitors of multi-drug resistance protein 5. A preferred embodiment of the invention is directed to a combination therapy comprising the administration to a patient of an effective amount of at least one (e.g., one) compound having the formula (I) or (Ia) in combination with an effective amount of at least one (e.g., one) serotonin 5-$HT_3$ receptor antagonist (e.g., ondansetron) and/or at least one (e.g., one) glucocorticoid (e.g., dexamethasone).

Pharmaceutical compositions may contain from about 0.1 to about 99.9 weight percent, or from about 5 to about 95 weight percent, or from about 20 to about 80 weight percent of active ingredient (compound having the formula (I) or (Ia)).

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington: The Science and Practice of Pharmacy, $20^{th}$ Edition, (2000), Lippincott Williams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparations subdivided into suitably sized unit doses containing appropriate quantities of the active component, e.g., an effective amount to achieve the desired purpose.

The quantity of active compound in a unit dose of preparation may be varied or adjusted from about 0.01 mg to about 4000 mg, preferably from about 0.02 mg to about 1000 mg, more preferably from about 0.3 mg to about 500 mg, and most preferably from about 0.04 mg to about 250 mg according to the particular application.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.02 mg/day to about 2000 mg/day, in two to four divided doses.

The pharmaceutical compositions of the invention may be administered from about 1 to about 5 times per day, or alternatively, as a continuous infusion. Such administration can be used as a chronic or acute therapy.

The quantity of $NK_1$ receptor antagonist in combination with a selective serotonin reuptake inhibitor ("SSRI") in a unit dose of preparation may be from about 10 to about 300 mg of $NK_1$ receptor antagonist combined with from about 10 to about 100 mg of SSRI. In another combination the quantity of $NK_1$ receptor antagonist in combination with a SSRI in a unit dose of preparation may be from about 50 to about 300 mg of $NK_1$ receptor antagonist combined with from about 10 to about 100 mg of SSRI. In another combination the quantity of $NK_1$ receptor antagonist in combination with SSRI in a unit dose of preparation may be from about 50 to about 300 mg of $NK_1$ receptor antagonist combined with from about 20 to about 50 mg of SSRI.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required. Upon improvement of a patient's condition, a maintenance dose of a compound, composition or combination of the invention may be administered, if necessary. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of disease symptoms.

Specific dosage and treatment regimens for any particular patient may be varied and will depend upon a variety of factors, including the activity of the specific compound employed, the age, body weight, general health status, sex and diet of the patient, the time of administration, the rate of excretion, the specific drug combination, the severity and course of the symptoms being treated, the patient's disposition to the condition being treated and the judgment of the treating physician. Determination of the proper dosage regimen for a particular situation is within the skill of the art.

Compounds having the formula (I) or (Ia) can be prepared using methods known to those skilled in the art. Typical procedures are described below, although a skilled artisan will recognize that other procedures may be applicable, and that the procedures may be suitably modified to prepare the same or other compounds within the scope of formula (I) or (Ia).

Definitions for abbreviations disclosed in the experimental section are as follows: Me is methyl; Bu is butyl; OH is hydroxyl; Ac is acetyl; Et is ethyl; Ph is phenyl; THF is tetrahydrofuran; OAc is acetate; $Et_2O$ is diethyl ether; $(Boc)_2O$ is di-tert-butyl dicarbonate; (Boc) is tert-butoxy carbonyl; TLC is thin layer chromatography; LDA is lithium diisopropyl amine; DCC is 1,3-dicyclohexylcarbodiimide; HATU is O-(7-azabenzotriazol-1-yl)-N,N,N',N',-tetramethyluronium hexafluorophosphate; TFA is trifluoroacetic acid; DIBAL or DIBAL-H is diisobutylaluminum hydride; DIEA or i-$Pr_2$EtN is diisopropylethyl amine; UNCA is Urea protected N-carboxy Anhydrides; IPA is 2-propanol; DMF is dimethylformamide; TBAF is tetrabutylammonium fluoride; TASF is tris(dimethylamino)sulfur (trimethylsilyl)difluoride; and equiv is equivalents.

Compounds having the formula (I) or (Ia) may be generally prepared from the corresponding ketone A1 (described in WO 01/44200, which is incorporated herein by reference thereto) as shown under the following conditions:

wherein:

$Ar^1$, $Ar^2$, $X^1$, $R^1$ through $R^3$ and $R^{10}$ through $R^{35}$ are as defined for formula (I);

$R^4$ and $R^5$ are independently selected from the group consisting of —H and —Cl;

$R^6$ and $R^7$, together with the carbon atom to which they are both attached, form a —C(=O) group; and $R^8$ and $R^9$ are each —H.

Wittig olefination of ketone A1 with the methyltriphenylphosphonium bromide and a suitable base, such as sodium amide or n-butyllithium, in THF provides alkene A2. Cycloaddition of the alkene with dichloroketene, which is generated in situ with trichloroacetylchloride and zinc-copper couple, in a suitable solvent, such as diethyl ether or ethylene glycol dimethyl ether ("DME"), affords dichlorocyclobutanone A3. The ketene may also be prepared in situ with dichloroacetylchloride, triethylamine, and a suitable solvent such as hexane. Additionally, the zinc-copper couple can be replaced with zinc dust when the cycloaddition is performed using ultrasound. Reduction of the dichlorides using a suitable reducing agent, such as sodium iodide and zinc dust in acetic acid gives cyclobutanone A4.

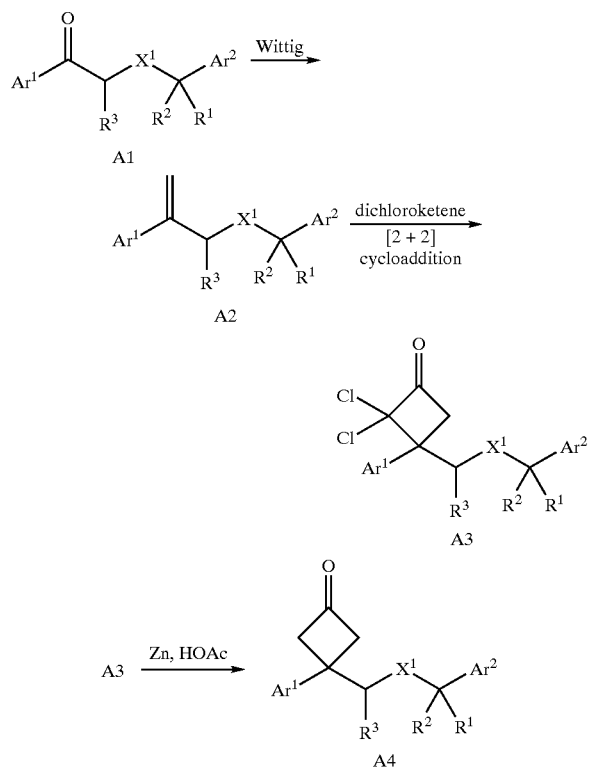

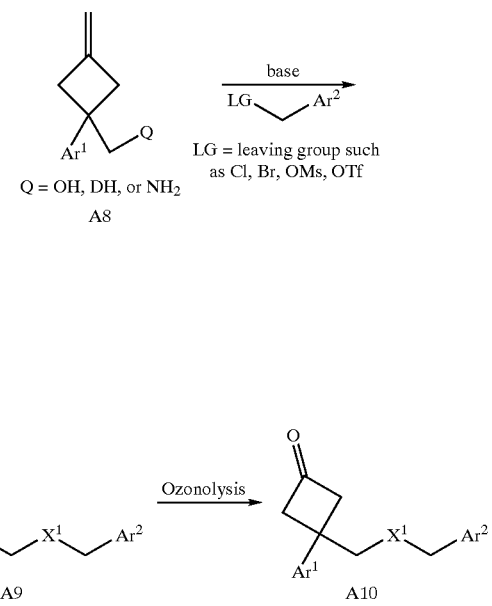

For derivatives where $R^1$ through $R^5$, $R^8$, and $R^9$ are equal to hydrogen an alternative cyclobutane synthesis can be utilized. Deprotonation of the benzyl nitrile A5 with sodium hydride in DMF is followed by the addition of 3-chloro-2-chloromethyl-1-propene to afford cyclobutane A6. Reduction of the nitrile preferably with DiBAL-H in THF yields the aldehyde A7. Additional methods for the reduction of the nitrile are with Raney nickel and sodium hypophosphate in aqueous acetic acid-pyridine or formic acid and with other hydride reducing agents such as $LiAlH_4$ and $NaAlH_4$. Those skilled in the art will recognize that the aldehyde can be converted to an alcohol (Q=OH) by reduction with a hydride reducing agent, a sulfide (Q=SH) by standard alkylation methods from the alcohol, or the amine (Q=NH$_2$) by reductive amination. Alkylation of A8 with an electrophile containing the second aryl moiety, $Ar^2$, further functionalizes the side chain to provide cyclobutane A9. Ozonolysis of the alkene in dichloromethane is the method of choice for the formation of ketone A10.

Further derivatization of cyclobutanone A4 may be performed through deprotonation with a suitable base, such as LDA or KHMDS, followed by the addition of an electrophile to provide the substituted cyclobutanone A11. Appropriate electrophiles can be, but are not limited, to alkyl halides, peroxide reagents, trisylazide, and disulfides. Those skilled in the art can elaborate these derivatives to prepare compounds, where $R^4$, $R^5$, $R^8$, and $R^9$ are independently selected from H, $C_1$-$C_6$ alkyl, —$OR^{20}$, —O—C(O)$NR^{15}R^{16}$, —$NR^{15}R^{16}$, —$NR^{15}SO_2R^{17}$, —$NR^{15}COR^{14}$, —$NR^{14}CONR^{15}R^{16}$, or —$SR^{20}$; or $R^4$ and $R^5$ together are =O or =$NR^{13}$.

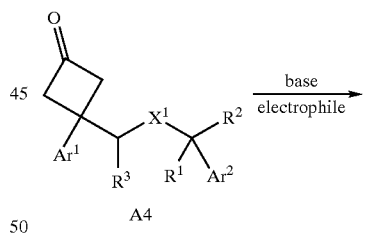

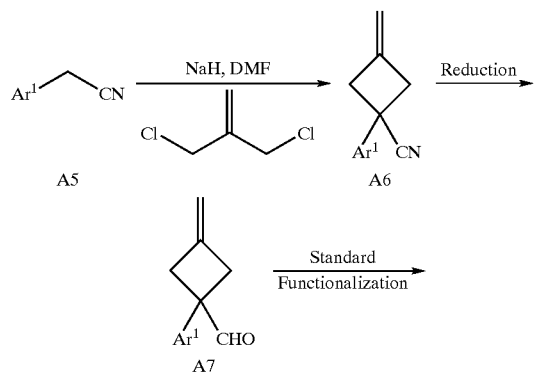

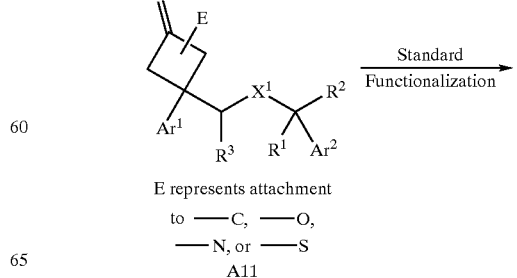

-continued

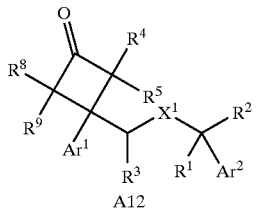
A12

To those skilled in the art, manipulation of the ketone moiety in A12 to the reported functional groups represented in $R^6$ and $R^7$ may require certain additional protection and deprotection steps. Accordingly, the order of synthetic operations may be different in order to maintain functional group compatibility with the operational steps in the synthesis.

The following modifications to ketone A12 can provide compounds of the type A13 where $R^6$ is H, and $R^7$ is either —OH, —O—($C_1$-$C_6$ alkyl), —$SO_2R^{15}$, —O—($C_3$-$C_8$ cycloalkyl), —O—C(O)$NR^{15}R^{16}$, —$NR^{15}R^{16}$, —$SO_2NR^{15}R^{16}$, —$NR^{15}SO_2R^{17}$, —$NR^{15}COR^{14}$, —$NR^{14}CONR^{15}R^{16}$ or one of the structures below:

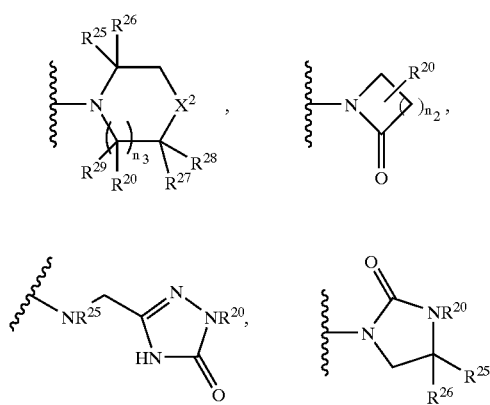

Reduction of the ketone A12 with a hydride reducing agent, such as lithium aluminum hydride or sodium borohydride, will provide a secondary alcohol. Conversion of the alcohol to ethers, thioethers, sulfones, carbamates and sulfonamides as defined above can be performed with standard methods. Preferably, reductive amination of ketone A12 with a primary or secondary amine and sodium triacetoxyborohydride readily afford amines. Alternatively, reductive aminations can be accomplished with sodium cyanoborohydride, sodium borohydride, zinc/HCl, or $BH_3$-pyridine as the reducing agent. Additional functionalization of the amines by standard alkylation, acylation, sulfonylation, addition to isocyanates, or coupling with an appropriate carboxylic acid to the above analogs can be recognized by those skilled in the art.

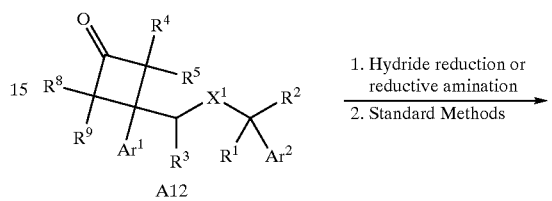

1. Hydride reduction or reductive amination
2. Standard Methods

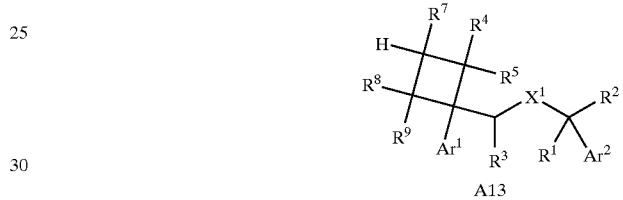
A13

The synthesis of compounds where $R^6$ or $R^7$ together are =$CH_2$, =$NR^{13}$, or =$NR^{15}$ originates with ketone A12. Wittig olefination of A12 with triphenylphosphonium bromide and n-butyllithium affords alkene A14. Oximes and oxime ethers, A15, are readily obtained from the reaction of the ketone with a hydroxyl- or alkoxyl-amine hydrochloride salt in pyridine as the solvent. Preferentially, imines are formed from ketones and primary amines in the presence of catalytic acid, such as para-toluenesulfonic acid, with the removal of water by a Dean-Stark apparatus.

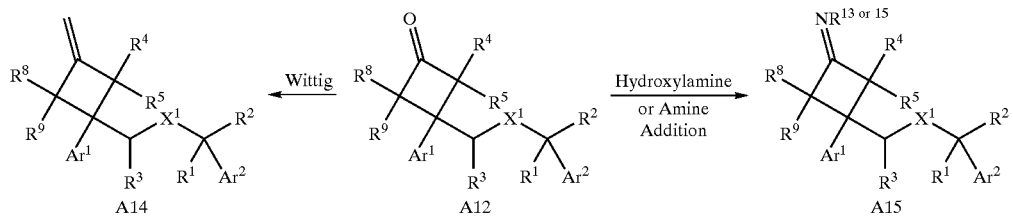

In cases where $R^6$ or $R^7$ is not hydrogen, a quaternary center may be generated from ketone A12 to provide compound A17 where $R^7$ is —$(CH_2)_{n_6}$-J, where $n_6$ is 0–5, J is H, —$CF_3$, —$CHF_2$, —$CH_2F$, —$C_3$-$C_8$ cycloalkyl, and $R^6$ is —OH, —O—($C_1$-$C_6$ alkyl), —O—($C_3$-$C_8$ cycloalkyl), —O—C(O)$NR^{15}R^{16}$, —$NR^{15}R^{16}$, —$NR^{15}SO_2R^{17}$, —$NR^{15}COR^{14}$, —$NR^{14}CONR^{15}R^{16}$, or one of the structures below.

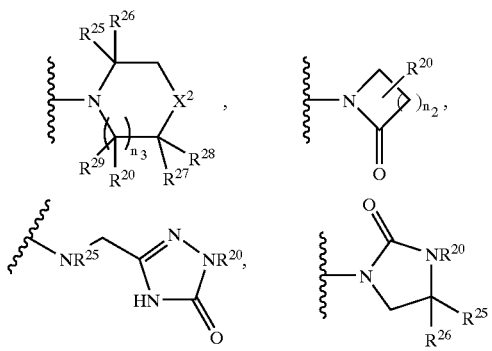

Incorporation of an alkyl group in the $R^7$ position of A12 to afford a tertiary alcohol can be completed with the addition of a Grignard reagent to the ketone. Organometallic reagents such as alkyllithiums and alkylzincs may also be employed for this transformation. For —$CF_3$ and —$CHF_2$ moieties where the organometallic reagent cannot be generated the following protocol is applied. The method of choice for introducing a trifluoromethyl group to a ketone is with trimethylsilyltrifluoromethane (Ruppert's Reagent) and catalytic tetrabutylammonium fluoride in THF. Subsequent addition of aqueous mild acid hydrolyzes the silylether to the desired carbinol A16. In instances where acid sensitive functionality is present, basic hydrolysis with potassium carbonate and methanol or TBAF in THF can be used. The difluoromethyl group can be incorporated in a similar manner using (difluoromethyl)phenyldimethylsilane and catalytic TASF or potassium fluoride in DMF followed by mild acid hydrolysis. Functionalization of the alcohol A16 to ethers, thioethers, sulfones, and sulfonamides can be performed with standard methods.

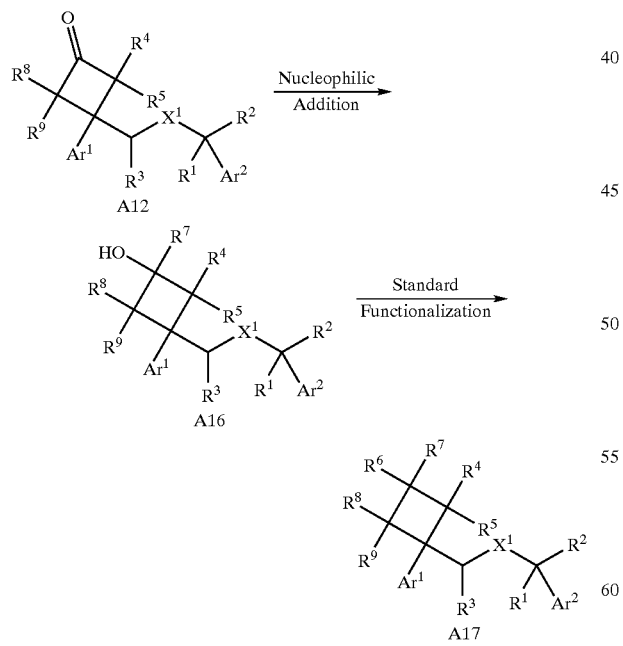

Additionally, the incorporation of alkyl groups, particularly —$CH_2F$, could be obtained through conversion of the ketone to an epoxide A18 with dimethyloxosulfonium methylide or diazomethane. Nucleophilic addition to the epoxide would provide an alternate route to tertiary alcohol derivative A16.

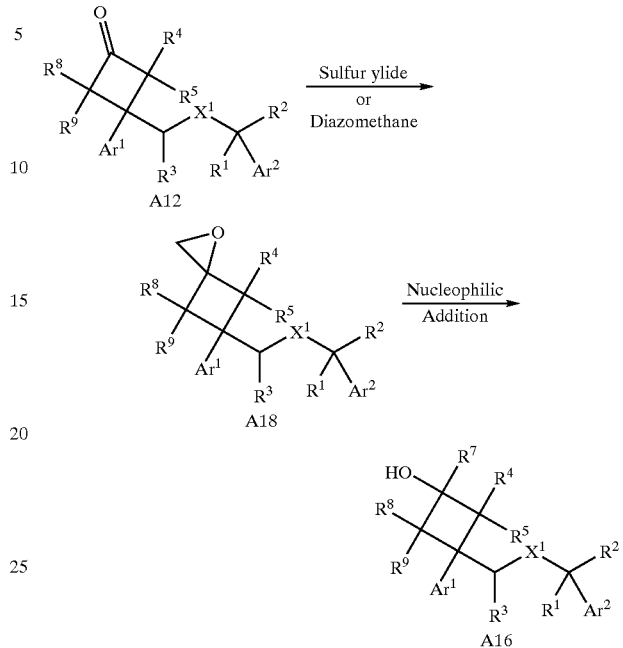

Preferentially, the formation of a quaternary center at $R^6$ and $R^7$, where $R^6$ is an amine, commences with the conversion of the ketone to a nitrone. Thus, formation of the nitrone with N-hydroxylbenzylamine and subsequent addition of a Grignard reagent generates the benzyl-protected hydroxylamine A19. Reduction to the secondary amine with zinc dust in acetic acid affords the benzylamine, which can be derivatized to nitrogen-containing analogs by the previously listed methods. Those skilled in the art will recognize that an imine, iminium salt, or a chiral sulfoxylimine is also a viable intermediate. Grignard reagents add to iminium salts, however, when using a sulfoxylimine or imine, alkyllithiums are the reagents of choice. The previously described chemistry to incorporate a —$CF_3$ or —$CHF_2$ can be applied to imines with the addition of trimethylsilylimidazole to the reaction and the use of stoichiometric cesium fluoride.

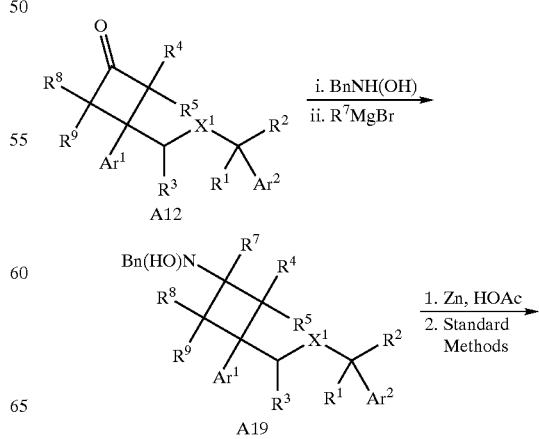

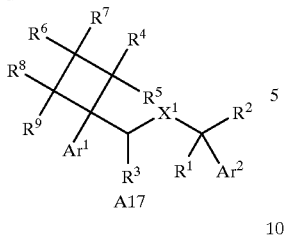

A17

Analogous to the chemistry described with epoxide A18, the —CH$_2$F moiety, along with other alkyl analogs, are accessible through an aziridine A20. Aziridination of the alkene A8 can be accomplished with chloramine-T or (N-(p-toluenesulfonyl)imino)-phenyliodinane. Nucleophilic addition to A20 followed by further functionalization will provide the previously listed nitrogen-containing derivatives.

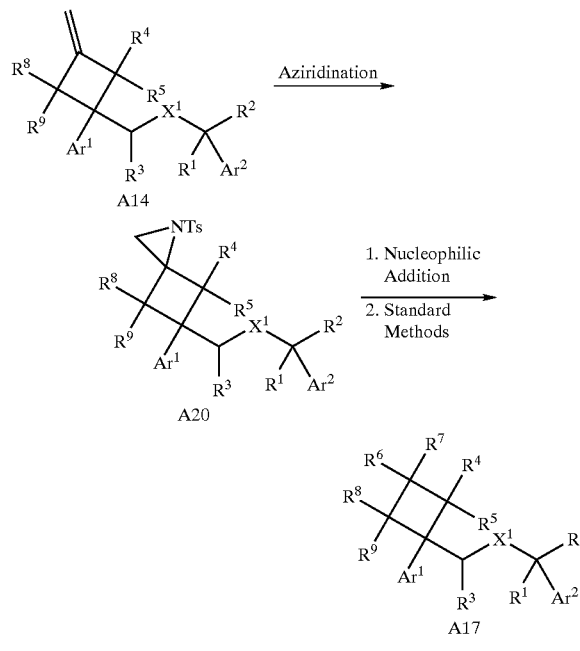

Spirocyclic analogs can be prepared where R$^6$ and R$^7$ together with the carbon to which they are attached form a four to seven-member heterocycloalkyl or heterocycloalkenyl ring, which includes but is not limited to hydantoins, ureas, lactams, imidazolones, imidazolidinones, piperazines, morpholines, and cyclic amines. Ketone A12 is converted to hydantoin A21 with potassium cyanide and ammonium carbonate in aqueous ethanol with heating. Reduction of the hydantoin to the cyclic urea A22 occurs with the addition of lithium aluminum hydride and aluminum trichloride in THF.

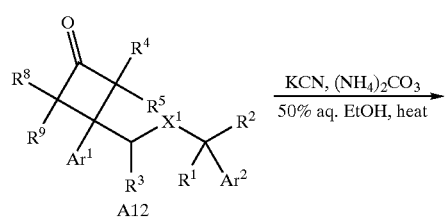

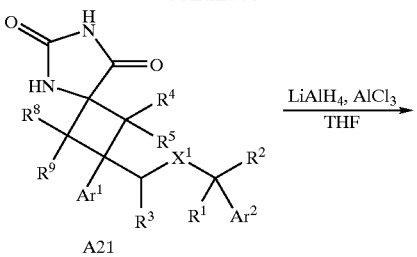

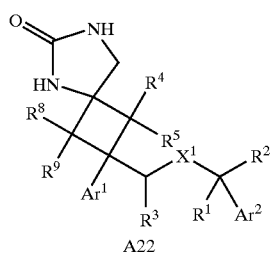

The above transformation of ketone A12 to a hydantoin may also be accomplished through a stepwise process using the Strecker reaction. Initial formation of an aminonitrile from ketone A12 is obtained with sodium cyanide, and a suitably protected-primary amine, such as benzylamine, in methanol and acetic acid. Preferential basic hydrolysis of the nitrile with hydrogen peroxide and sodium hydroxide in ethanol provides the amino amide A23. Deprotection of the amine can be performed by methods known to those skilled in the art. The addition of triphosgene to the amino amide affords the spirocyclic hydantoin A21.

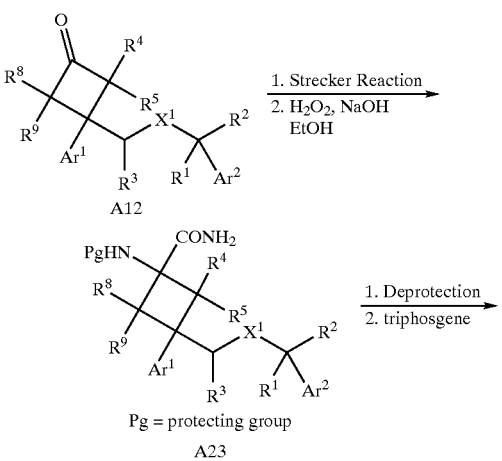

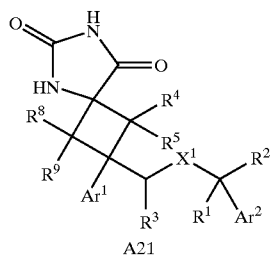

The spirocyclic beta-lactam is synthesized from alkene A14 by a [2+2] addition with N-chlorosulfonylisocyanate to afford lactam A24. Ring expansion of the beta- to the gamma-lactam may be achieved through the following route where the lactam nitrogen is protected preferably as the t-butyl carbamate. Opening of the imide system with trimethylsilyldiazomethane, a safer alternative to diazomethane, generates a diazoketone. Wolff rearrangement of the diazoketone is carried out photolytically in benzene or in the presence of a catalytic amount of silver benzoate and triethylamine in THF. Deprotection of the lactam nitrogen with TFA in dichloromethane provides the desired lactam A25. As represented with beta-lactam A26, reduction of a lactam to the cyclic amine derivative A27 is completed with lithium aluminum hydride and aluminum trichloride.

reduction of the UNCA to the alcohol, preferably with lithium borohydride, and subsequent oxidation to the aldehyde with the Swern protocol generates Boc-amino aldehyde A31. Homologation of the aldehyde by aldol condensation or preferably by Horner-Wadsworth-Emmons olefination provides ester A32. Subsequent hydrogenation and removal of the Boc-protecting group with trifluoroacetic acid will provide the desired lactam A25.

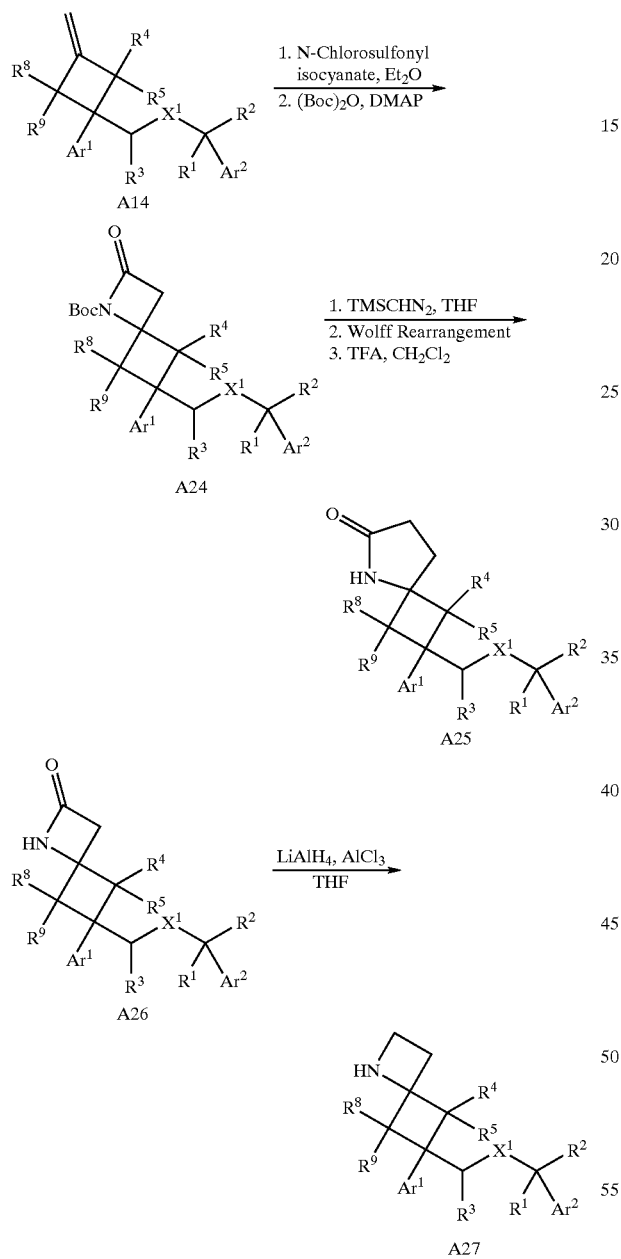
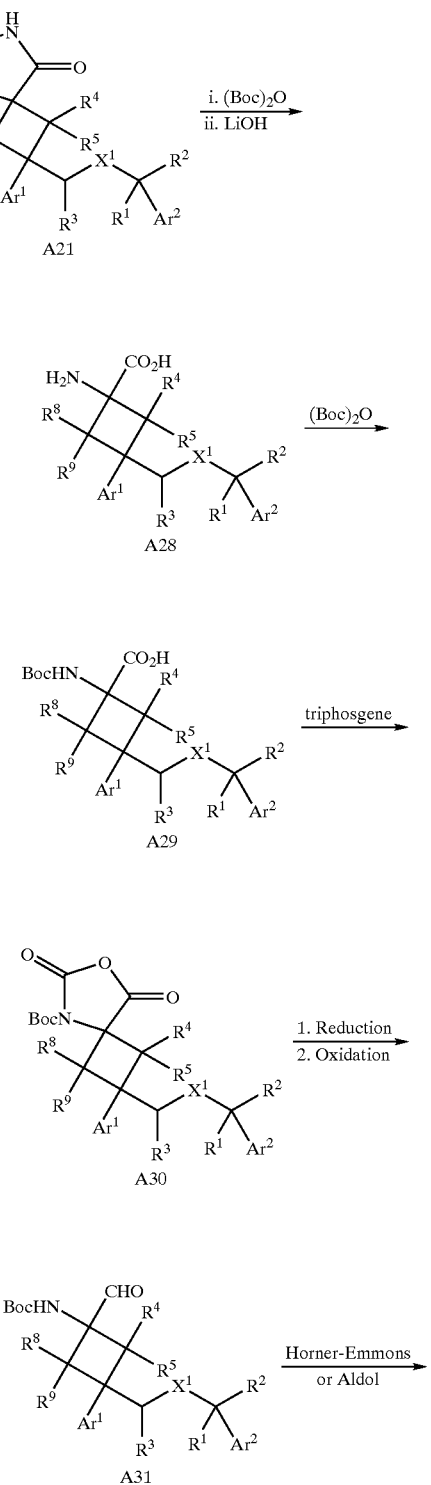

An alternative method for the preparation of lactam A25 involves hydrolysis of the hydantoin A 21 by protection of the hydantoin with Boc-anhydride and the subsequent addition of lithium hydroxide solution to form the amino acid A28. An alternate method for the basic hydrolysis of the hydantoin is with sodium hydroxide in aqueous ethanol at elevated temperatures. Protection of the nitrogen as the tert-butyl carbamate A29 followed by cyclization with triphosgene then affords the UNCA derivative A30. Hydride

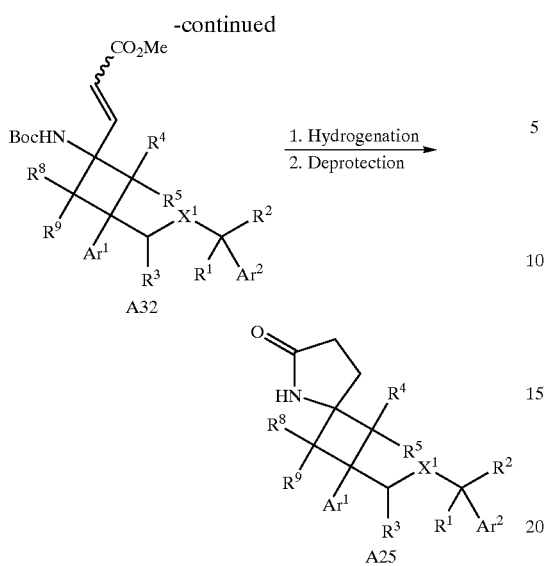

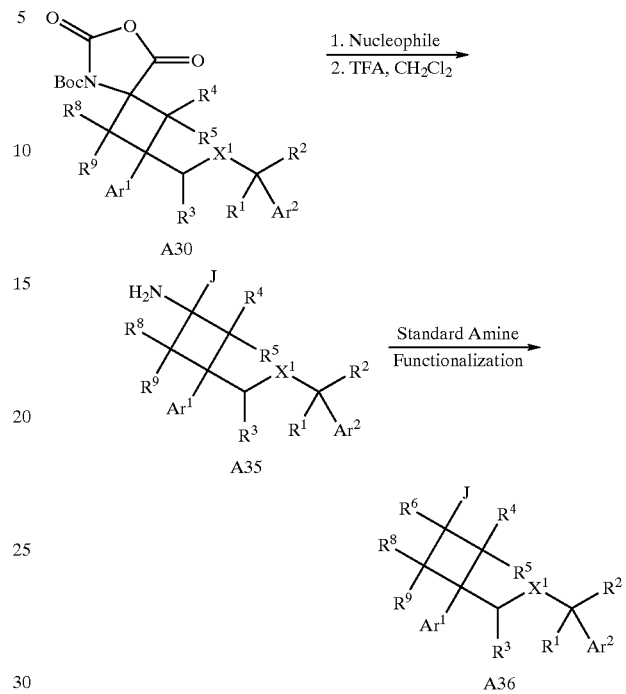

The spirocyclic gamma-lactam positional isomer is prepared from cyclobutanone A12. An initial Horner-Wadsworth-Emmons reaction with an ester phosphonate is followed by a Michael addition with nitromethane in the presence of a suitable base, such as TBAF, in refluxing THF to provide nitro ester A33. The nitro group is reduced by hydrogenation in the presence of Raney nickel to the amine which spontaneously cyclizes to afford the lactam A34.

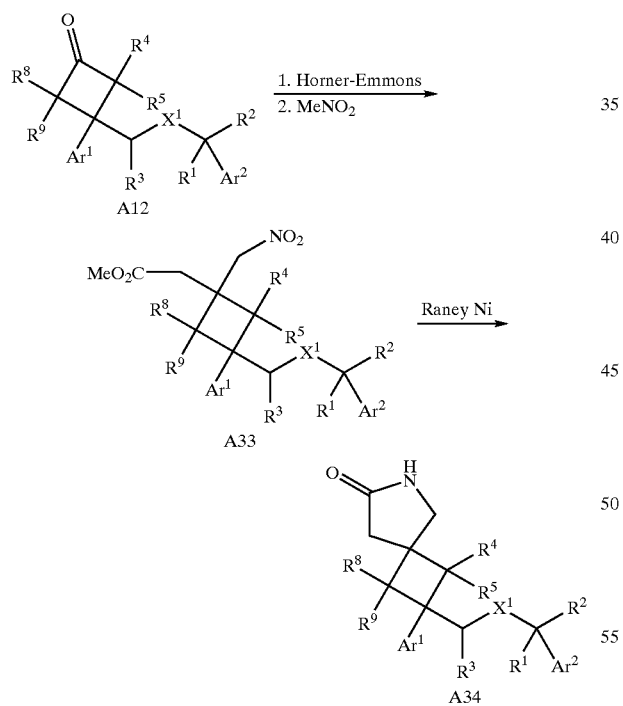

The following route can be applied in cases when $R^7$ is —(CH$_2$)$_{n6}$-J, where $n_6$=0, J is —C(O)NR$^{15}$R$^{16}$ or —C(O)OR$^{14}$ and R$^6$ is —NR$^{15}$R$^{16}$, —NR$^{15}$SO$_2$R$^{17}$, —NR$^{15}$COR$^{14}$, or —NR$^{14}$CONR$^{15}$R$^{16}$. Starting with the Boc-protected UNCA derivative A30, addition of an alkoxide or amine would provide an ester or amide analog. Preferentially, the Boc-protecting group is removed with trifluoroacetic acid in dichloromethane to afford A35. Functionalization of the amine by standard alkylation, acylation, sulfonylation, addition to isocyanates, or coupling with an appropriate carboxylic acid can be recognized by those skilled in the art.

In addition to the formation of amino amides through the UNCA derivative A30, the following route can be applied in cases when $R^7$ is —(CH$_2$)$_{n6}$-J, where $n_6$=0, J is —C(O)NR$^{15}$R$^{16}$ and R$^6$ is —NR$^{15}$R$^{16}$, —NR$^{15}$SO$_2$R$^{17}$, —NR$^{15}$COR$^{14}$, or —NR$^{14}$CONR$^{15}$R$^{16}$. The Boc-protected amino acid A29 can undergo a coupling reaction with ammonia, primary or secondary amines, preferably in the presence of PyBOP to activate the carboxylic acid, to provide Boc-amino amide A37. Those who are skilled in the art recognize other coupling reagents, such as CDI, DCC, EDC/HOBt, and HATU, can be used in the conversion of carboxylic acids to amides. Removal of the Boc-protecting group preferably with TFA in dichloromethane can be followed by elaboration of the amine by the previously described methods to afford derivatives of the type A36.

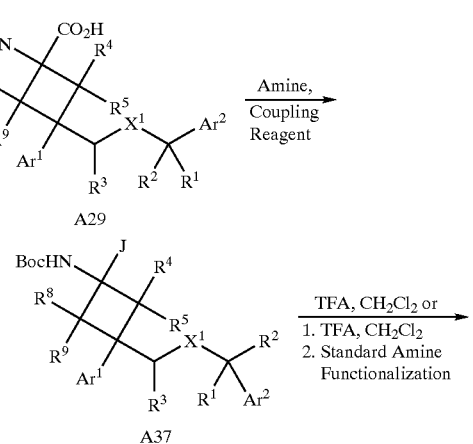

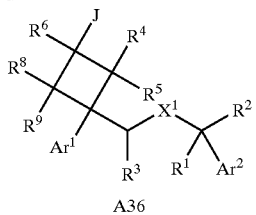

A36

Nitrogen-substituted analogs of hydantoin A21 can be prepared from secondary amino amides A38 where $R^{20}$ is $C_1$–$C_6$ alkyl, $C_3$–$C_8$ cycloalkyl, hydroxy($C_2$–$C_8$)alkyl, or ($C_1$–$C_6$)alkoxy($C_1$–$C_6$)alkyl. The addition of triphosgene in the presence of an amine base affords substituted hydantoin A39.

where $R^{15}$ is the same as defined in the summary of the invention. Condensation of the amino amide with an orthoformate, preferably triethylorthoformate, in refluxing toluene with catalytic acetic acid affords the imidazolone A42. Reduction to the imidazolone is accomplished preferably with sodium borohydride in methanol to give imidazolidinone A43. The imidazolone can also be reduced by hydrogenation over platinum oxide, Raney nickel, or palladium on carbon.

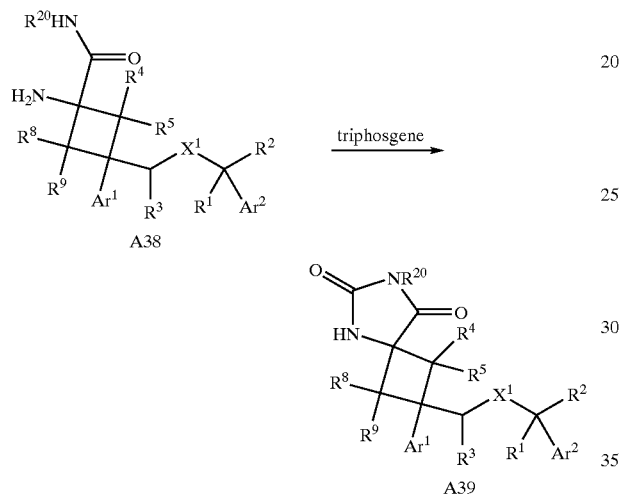

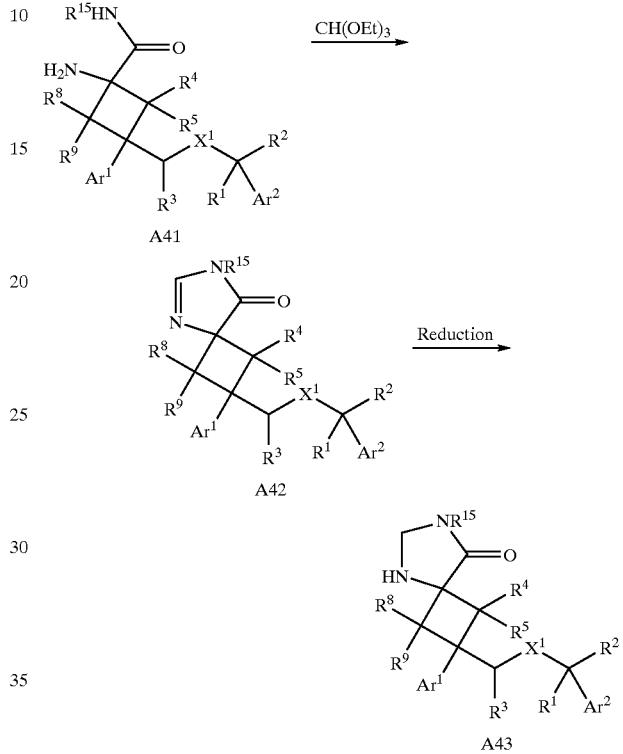

In addition to the above method, N-alkyl substituted hydantoins can be prepared from hydantoin A21 by standard alkylation conditions with potassium carbonate and an alkyl bromide in DMF to obtain A39. Alkylation of the less reactive nitrogen of the hydantoin to provide analog A40 could be accomplished through protection of the more reactive nitrogen, standard alkylation, and subsequent removal of the protecting group.

Those skilled in the art will also recognize that the addition of an orthoester in place of an orthoformate to an amino amide would provide alkyl- or aryl-substituted imidazolones A44. Likewise, condensation of the amino amide with acetone in methanol with acid, such as para-toluenesulfonic acid, would afford the dimethyl-substituted imidazolidinone A45.

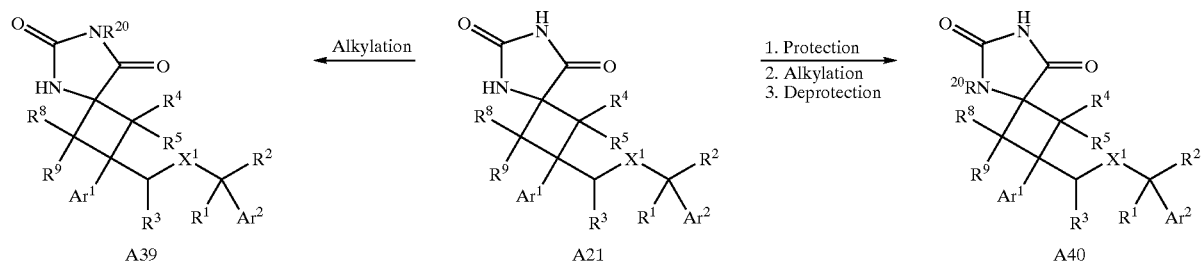

Spirocyclic imidazolones and imidazolidinones can be prepared from primary and secondary amino amides A41,

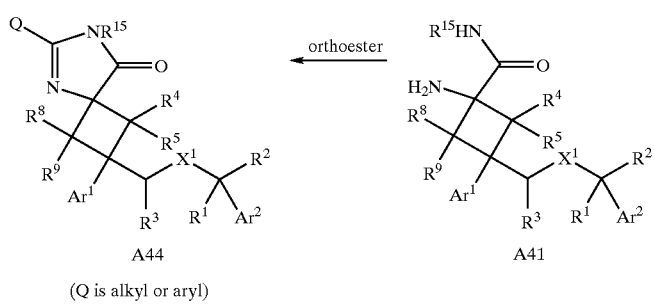
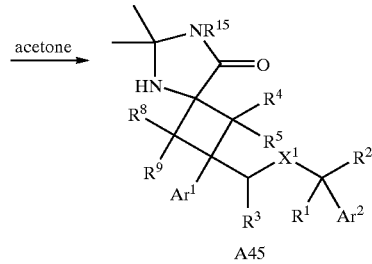

(Q is alkyl or aryl)

For derivatives when $R^7$ is —$(CH_2)_{n6}$-J, where $n_6$=1–5, J is —C(O)$NR^{15}R^{16}$, or —C(O)$OR^{14}$ and $R^6$ is —$NR^{15}R^{16}$, —$NR^{15}SO_2R^{17}$, —$NR^{15}COR^{14}$, or —$NR^{14}CONR^{15}R^{16}$ the following route can be used. One carbon homologation of aldehyde A31 can be obtained using Wittig reagents such as methoxymethyl triphenylphosphonium bromide or cyanomethyltriphenylphosphonium bromide. Additionally, formation of an acid chloride followed by the Arndt-Eistert protocol will afford the homologated ester or amide analogs. Further chain extensions can be obtained through Wittig and Horner-Wadsworth-Emmons chemistry. Functionalization of the amine to afford derivatives of the type A47 is analogous to the previously reported procedures.

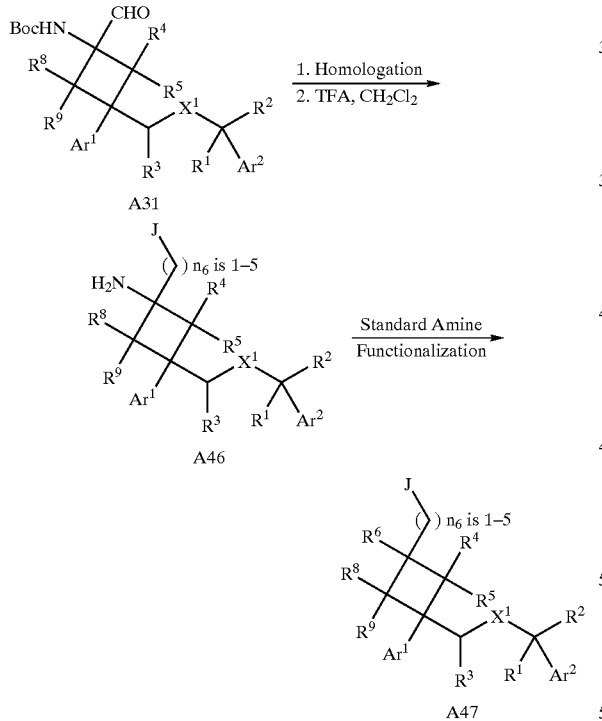

For derivatives where $R^7$ is —$(CH_2)_{n6}$-J, where $n_6$=1, J is is —$NR^{15}R^{16}$, —$NR^{15}SO_2R^{17}$, —$NR^{15}COR^{14}$, or —$NR^{14}CONR^{15}R^{16}$ and $R^6$ is —$NR^{15}R^{16}$, —$NR^{15}SO_2R^{17}$, —$NR^{15}COR^{14}$, or —$NR^{14}CONR^{15}R^{16}$ the following route can be used. Initial formation of an amino nitrile from ketone A12 is obtained with sodium cyanide, and a suitable protected primary amine, such as benzylamine, in methanol and acetic acid. Reduction of the nitrile, preferably with lithium aluminum hydride, in ether affords the protected diamine A48. Those who are skilled in the art will recognize other methods to reduce nitriles to amines with other hydride reducing agents or hydrogenation with a catalyst. Deprotection of the amine or further functionalization followed by deprotection will afford derivatives with the structure A49.

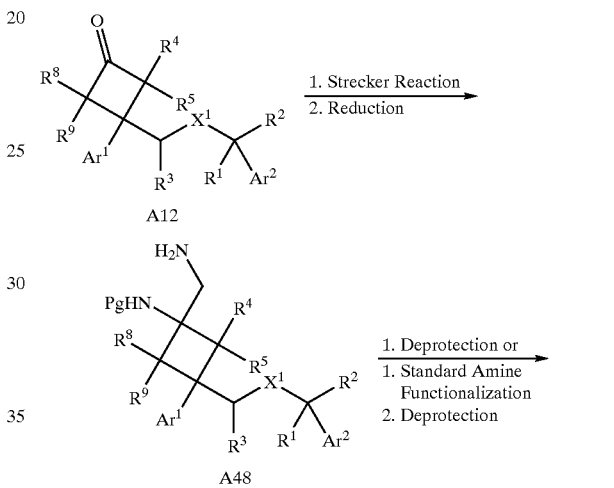

In addition to the A49 analogs, $R^6$ and $R^7$, together with the carbon atom to which they are both attached, can form a piperazine ring. Deprotection of diamine A48 followed by cyclization with chloroacetyl chloride will provide the ketopiperazine derivative A50.

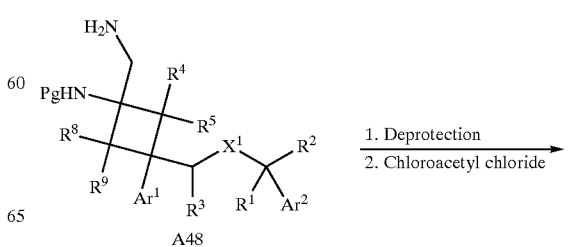

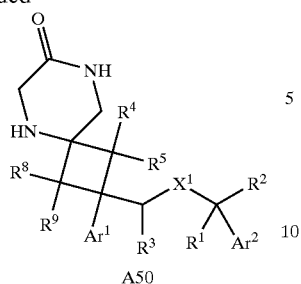

A50

Cyclic carbamates and morpholine analogs can be prepared from amino acid A28. Reduction of the carboxylic acid with lithium borohydride in the presence of trimethylsilyl chloride in THF provides amino alcohol A51. Cyclization to carbamate A52 and keto-morpholine A53 is accomplished with triphosgene or phenylbromoacetate addition, respectively, to the amino alcohol in the presence of diisopropylethylamine.

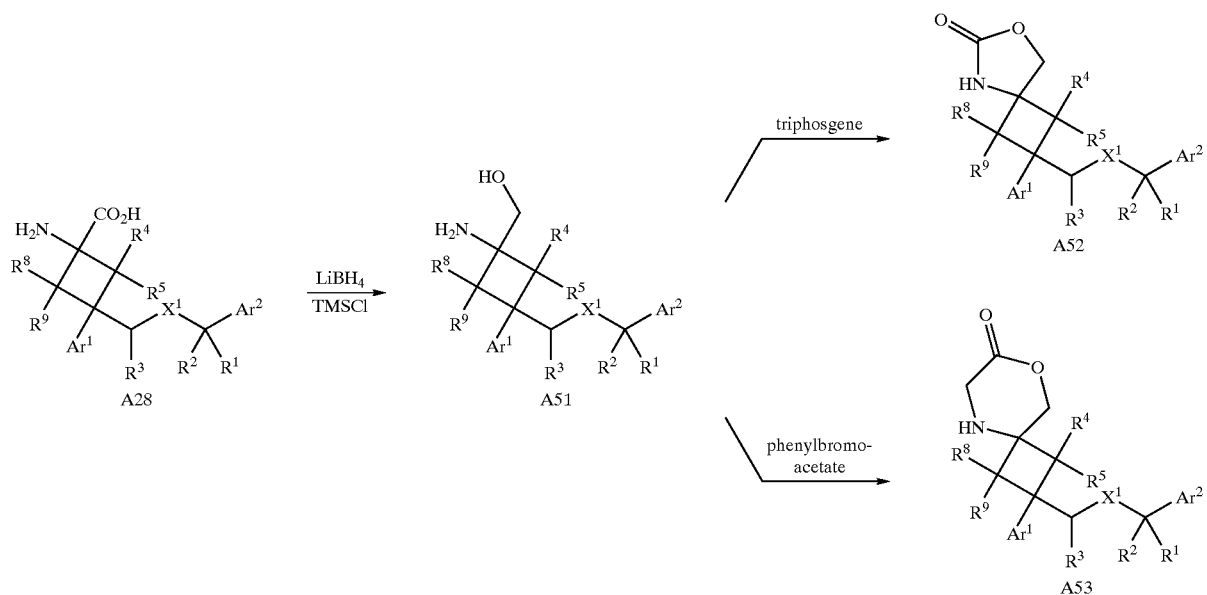

For derivatives where $R^7$ is —$(CR^{40}R^{41})_{n6}$-J, where $R^{40}$ and $R^{41}$ are not hydrogen and $n_6=1$, J is is —OH, —O—($C_1$-$C_6$ alkyl), —O—($C_3$-$C_8$ cycloalkyl), —O—C(O)$NR^{15}R^{16}$ and $R^6$ is —$NR^{15}R^{16}$, —$NR^{15}SO_2R^{17}$, —$NR^{15}COR^{14}$, or —$NR^{14}CONR^{15}R^{16}$ the following route can be used. Esterification of the Boc-amino acid A29 with trimethylsilyldiazomethane, a safer alternative to diazomethane, followed by addition of methyl magnesium bromide affords a mixture of the Boc-amino alcohol A54 and cyclic carbamate A55. Derivative A54 can afford an amino alcohol upon deprotection of the Boc-moiety with TFA or with further functionalization of the alcohol followed by deprotection afford amino ethers or amino carbamates. A ketomorpholine derivative analogous to A53 can be prepared by the previously defined conditions.

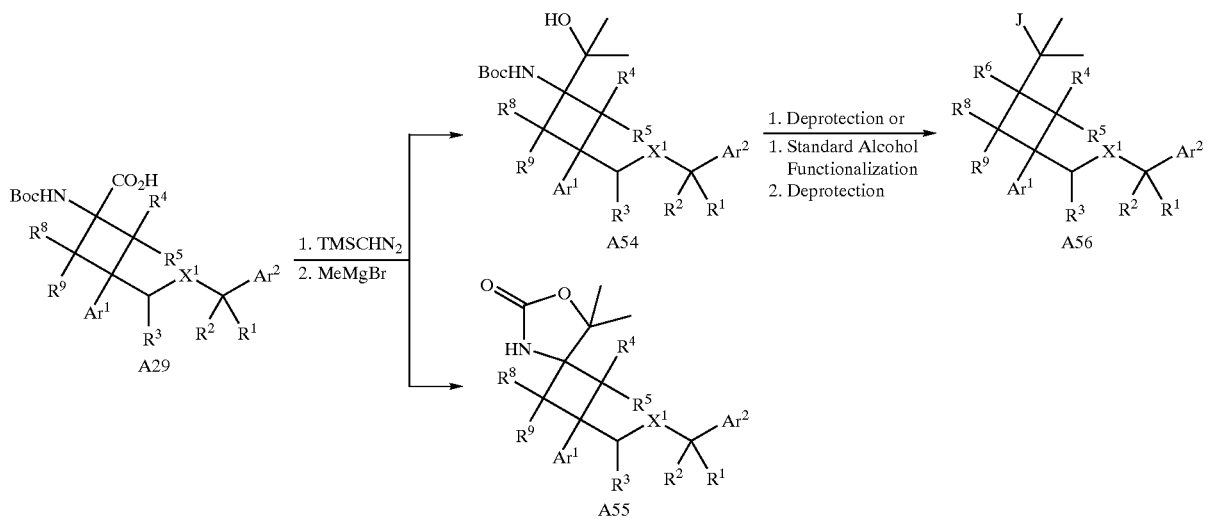

In examples where $R^4$ and $R^5$ together with the carbon atom to which they area attached, form a —C(=O) group and $R^6$ through $R^9$ is hydrogen, the following preparation of the core cyclobutanone employs ketone A1. Using a protocol reported by Trost, B. M.; Bogdanowicz, M. J. J. Am. Chem. Soc., 95, 5321(1973), which is incorporated by reference in its entirety, the addition of diphenylcyclopropyl ylide to the ketone A1 initially affords an oxaspiropentane. This intermediate rearranges to the cyclobutanone upon treatment with lithium perchlorate or lithium tetrafluoroborate. The chemistry described for the elaboration of the cyclobutanone A4 is applicable to the functionalization of cyclobutanone A57.

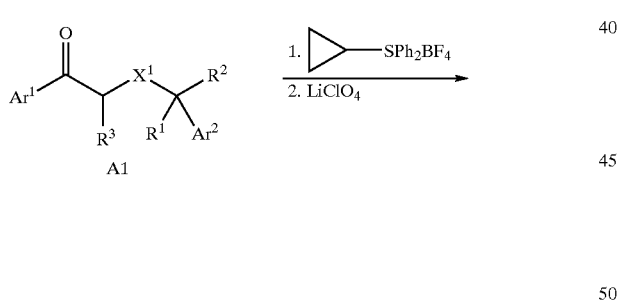

The invention disclosed herein is exemplified by the following examples which should not be construed to limit the scope of the disclosure. Alternative mechanistic pathways and analogous structures may be apparent to those skilled in the art.

PREPARATION OF EXAMPLES 1a AND 1b

EXAMPLE 1a

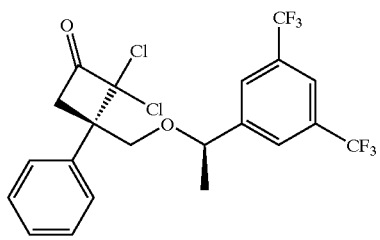

EXAMPLE 1b

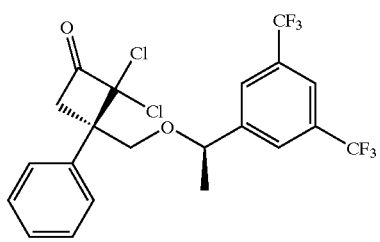

Step 1:

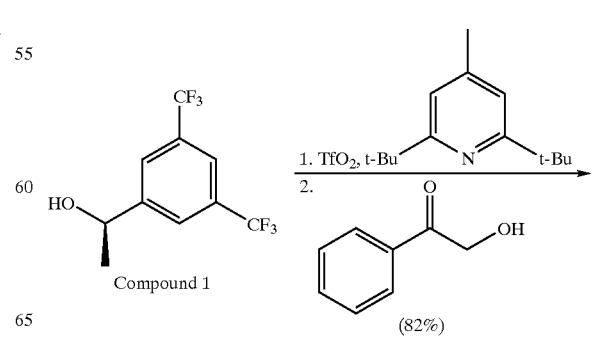

-continued

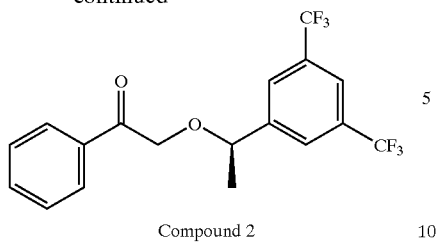

Compound 2

Procedures for preparing Compound 1 and Compound 2 are shown in WO 01/44200.

Step 2:

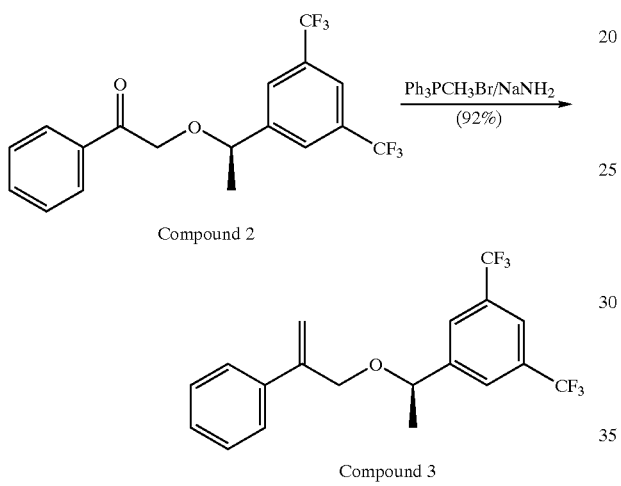

To methyltriphenylphosphonium bromide/sodium amide ("Instant Ylide" reagent) (20.9 g, 50.1 mmol, 1.3 equiv) in a 500 mL RBF under N$_2$ was added anhydrous THF (210 mL). The yellow suspension became warm and was allowed to stir for 20 minutes. Compound 2 (14.5 g, 38.5 mmol, 1.0 equiv) as a solution in anhydrous THF (50 mL) was added via cannula over 20 minutes. The reaction mixture was allowed to stir at rt for 24 h. The solution was filtered through a 1" plug of silica gel and rinsed with 1 L of 5% EtOAc/hexane. The solution was concentrated in vacuo to provide a solid/oil mixture. The crude material was using a 5" silica plug in a glass-fritted funnel eluting with 2% EtOAc/hexane to afford pure alkene Compound 3 (13.2 g, 92.2%) as a bright yellow oil.

Step 3:

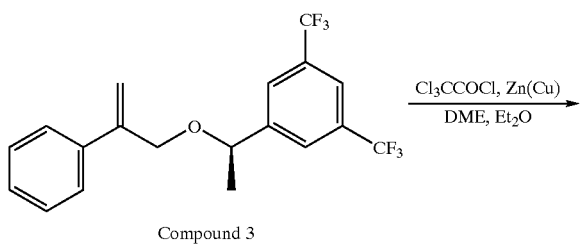

-continued

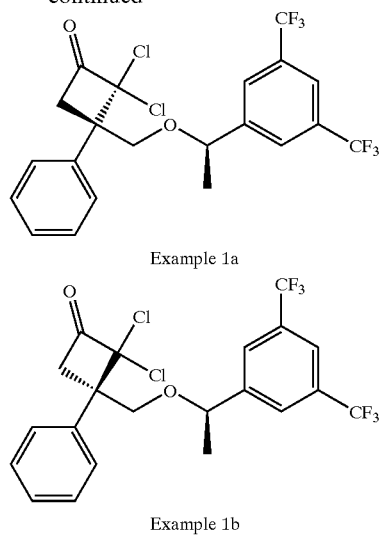

To Compound 3 (5.2 g, 13.9 mmol, 1.0 equiv) in a 200 mL RBF was added anhydrous Et$_2$O (50 mL) and anhydrous DME (7 mL) under N$_2$. Zinc copper couple (2.7 g, 41.3 mmol, 3.0 equiv) was added to the reaction mixture followed by dropwise addition of trichloroacetylchloride (4.7 mL, 42 mmol, 3.0 equiv) over 5 minutes. The reaction mixture was allowed to stir for 48 hours. After this time additional zinc copper couple (2.0 g) and trichloroacetylchloride (2.0 mL) was added. After 65 h, hexane (100 mL) was added and the brown suspension was allowed to cool to room temperature. After 2 h, the suspension was filtered through celite washing with 5% Et$_2$O/hexane (3×200 mL). The solution was concentrated in vacuo to afford a brown oil (9.6 g). The crude material was purified using a SiO$_2$ plug eluting with a solvent gradient of hexane to 5% EtOAc/hexane to 10% EtOAc/hexane to afford the desired isomers Example 1a and 1b (5.8 g, 86% yield). The ratio of Isomer A: B is 1:1.

Electrospray MS [M+Na]$^+$ 507.1 for Example 1a.
Electrospray MS [M+Na]$^+$ 507.1 for Example 1b.

PREPARATION OF EXAMPLE 2

EXAMPLE 2

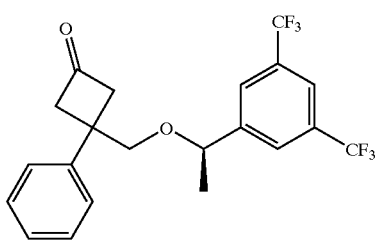

To the dichloroketene Example 1a and 1b (4.3 g, 8.86 mmol, 1.0 equiv) in acetic acid (39 mL) was added zinc dust (4.46 g, 70.9 mmol, 8.0 equiv) followed by NaI (2.65 g, 17.7 mmol, 2.0 equiv). The reaction mixture was allowed to stir for 48 h. The solution was allowed to cool to room temperature and was filtered through a plug of celite washing with EtOAc. The reaction mixture was taken up in EtOAc and washed with saturated NaHCO$_3$ (1×100 mL) followed by brine (1×100 mL). The organic layers were combined, dried over Na$_2$SO$_4$, filtered, and concentrated in vacuo. The crude material was purified by flash chromatography using a biotage eluting with a solvent gradient of 5% EtOAc/hexane to 10% EtOAc/hexane to afford Example 2 as yellow oil (3.0 g, 82% yield).

Electrospray MS [M+1]$^+$ 417.1 for Example 2.

PREPARATION OF EXAMPLE 3

EXAMPLE 3

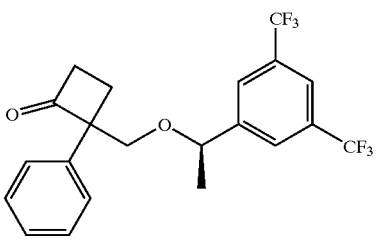

To Compound 2 (1.17 g, 3.1 mmol, 1.0 equiv) in anhydrous DMSO (10 mL) was added cyclopropyldiphenylsulfonium tetrafluoroborate (1.07 g, 3.4 mmol, 1.1 equiv). The reaction mixture was degassed well with $N_2$ and potassium hydroxide flakes (0.37 g, 7.0 mmol, 2.25 equiv) were added. After 18 h, the red reaction mixture was poured into hexane. The red oil was not soluble in hexane and was diluted with of ether (100 mL). The aqueous layer was extracted with (3×50 mL) ether. The combined organics were rinsed with saturated $NaHCO_3$ solution (2×50 mL), dried over $Na_2SO_4$, filtered, and concentrated in vacuo to afford 1.8 g of orange oil. The oil was diluted with benzene (8 mL) and lithium perchlorate (14 mg) was added. The suspension was heated to reflux for 4 hours. The reaction mixture was allowed to cool to room temperature, washed once with $H_2O$ and saturated $NaHCO_3$ solution, dried over $Na_2SO_4$ filtered, and concentrated in vacuo. The crude material was purified by flash chromatography using a biotage eluting with 3% EtOAc/hexane to give Example 3 (0.65 g, 52% yield) as yellow oil.

Electrospray MS [M+1]$^+$ 417.1 for Example 3.

PREPARATION OF EXAMPLE 4

EXAMPLE 4

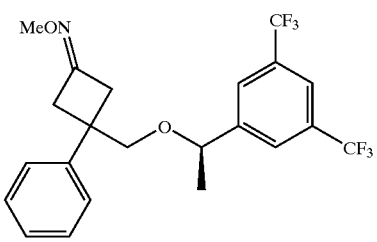

To Example 2 (0.091 g, 0.22 mmol, 1.0 equiv) in pyridine (1 mL) was added methoxylamine hydrochloride (0.22 g, 0.26 mmol, 1.2 equiv) and the reaction mixture was allowed to stir at room temperature for 24 hours. The reaction was quenched with $H_2O$ and diluted with EtOAc. The organic layer was washed twice with $H_2O$, and once with brine, dried over $Na_2SO_4$, filtered, and concentrated in vacuo to afford a yellow oil. The crude material was purified by flash chromatography using a biotage eluting with 5% EtOAc/hexane to afford the desired product Example 4 (0.10 g, 100% yield) as a colorless oil.

Electrospray MS [M+1]$^+$ 446.1 for Example 4.

PREPARATION OF EXAMPLE 5

EXAMPLE 5

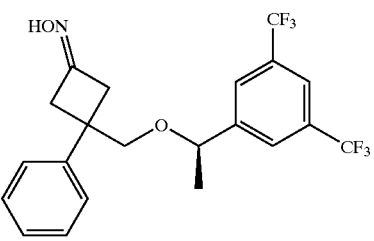

The title compound was prepared by a method analogous to that described for Example 4, using hydroxylamine hydrochloride in place of methoxylamine hydrochloride.

Electrospray MS [M+1]$^+$ 432.1 for Example 5.

PREPARATION OF EXAMPLE 6

EXAMPLE 6

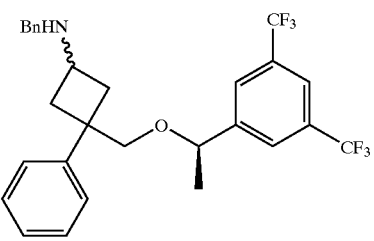

To Example 2 (2.9 g, 7.0 mmol, 1.0 equiv) in 1,2-dichloroethane (28 mL) under $N_2$ was added benzylamine (6.0 g, 56 mmol, 8.0 equiv). After 20 minutes, sodium triacetoxyborohydride (3.0 g, 14 mmol, 2.0 equiv) was added followed by acetic acid (0.5 g, 8.4 mmol, 1.2 equiv). The reaction was monitored by TLC and showed the presence of starting material after 6 hours. An additional 1.5 g of sodium triacetoxyborohydride was added and the reaction mixture was allowed to stir for an additional 18 h. The reaction was quenched with saturated $NaHCO_3$ solution and diluted with EtOAc. The organic layer was washed once with $H_2O$ and brine, dried over $Na_2SO_4$, filtered, and concentrated in vacuo to afford a yellow oil. The crude material was purified by flash chromatography using a biotage eluting with 40% EtOAc/hexane to afford Example 6, a 1:1 mixture of diastereomers, as a light yellow oil (3.33 g, 94% yield).

Electrospray MS [M+1]$^+$ 508.1 for Example 6.

PREPARATION OF EXAMPLE 7

EXAMPLE 7

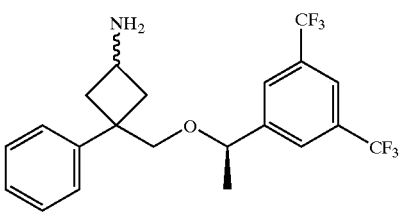

To Example 6 (1.9 g, 3.7 mmol, 1.0 equiv) in EtOH (30 mL) under $N_2$ was added 20% Pd(OH)$_2$ on carbon. The reaction mixture was allowed to stir overnight under $H_2$. The TLC indicated the presence of starting material, and an additional 0.3 g of 20% $Pd(OH)_2$ on carbon was added. After 36 h, the reaction mixture was filtered through celite and washed with EtOAc. The crude material was purified by flash chromatography using a biotage eluting with 5% $Et_3N/EtOAc$ to afford Example 7, a 1:1 mixture of diastereomers, as a pale yellow oil (1.25 g, 81% yield).

Electrospray MS $[M+1]^+$ 418.1 for Example 7.

PREPARATION OF EXAMPLES 8a AND 8b

EXAMPLE 8a

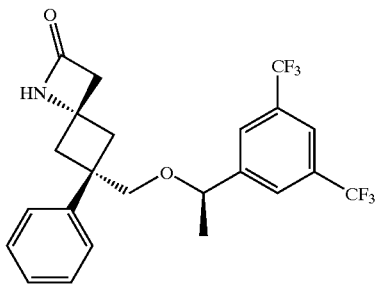

EXAMPLE 8b

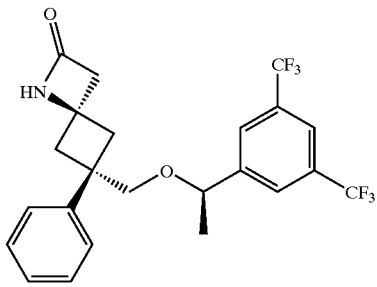

Step 1:

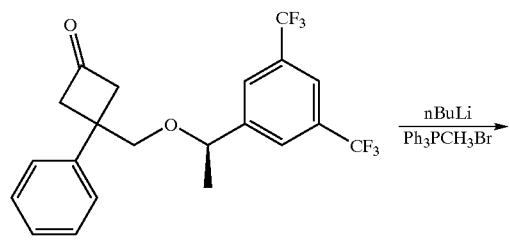

Example 2

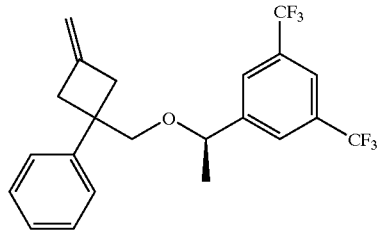

Compound 4

To methyltriphenylphosphonium bromide (0.86 g, 2.4 mol, 2.0 equiv) in anhydrous THF (50 mL) at 0° C. was added butyl lithium (1.5 mL, 2.4 mmol, 2.0 equiv) dropwise. After 30 minutes, the ice bath was removed and Example 2 (0.51 g, 1.2 mmol, 1.0 equiv) was added in THF (5 mL) via cannula over a period of 5 minutes. After 1 h, the solution was cooled to 0° C., quenched with saturated $NH_4Cl$ solution, and diluted with EtOAc. The organic layer was washed once with brine, dried over $Na_2SO_4$, filtered, and concentrated in vacuo to afford an orange residue. The crude material was purified by flash chromatography using a biotage eluting with the solvent gradient 5% EtOAc/hexane to 10% EtOAc/hexane to afford Compound 4 (0.036 g, 77% yield).

Step 2:

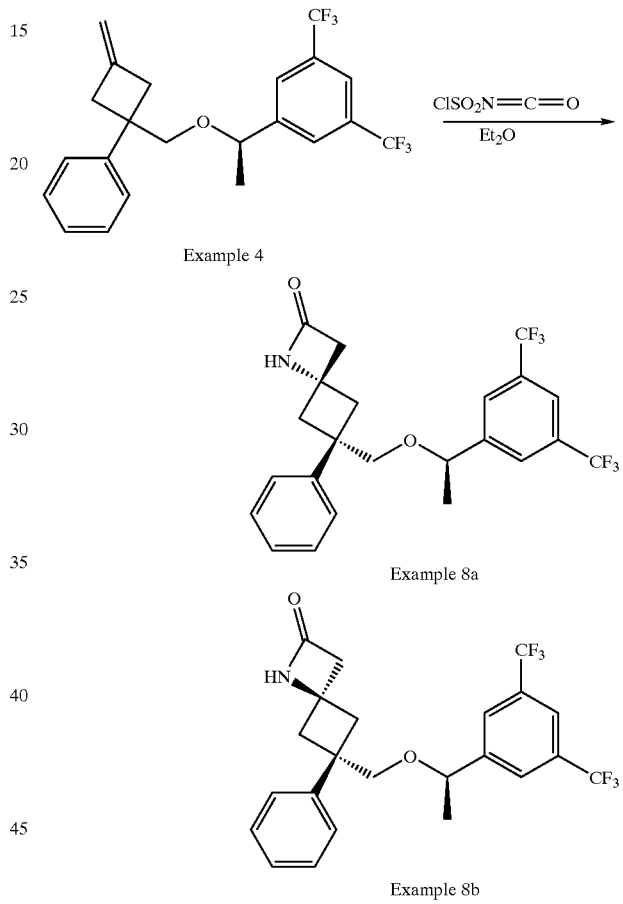

Example 4

Example 8a

Example 8b

To Compound 4 (0.49 g, 1.2 mmol, 1.0 equiv) in anhydrous ether (2.6 mL) at 0° C. was added chlorosulfonylisocyanate (0.018 g, 1.3 mmol, 1.1 equiv) dropwise. After 1 h the reaction mixture was allowed to warm to room temperature. After 19 h, additional isocyanate (55 μL) was added. After 4 h, the reaction mixture was concentrated in vacuo. The residue was diluted with ether (12 mL) and was added to a flask containing 25% sodium sulfate solution (12 mL) and ether (6 mL). The solution was adjusted to pH 8 with 2.0 M KOH solution. The biphasic mixture was allowed to stir for 1.5 hours. The organic layer was washed twice with brine, dried over $Na_2SO_4$, filtered, and concentrated in vacuo to afford the crude product as an oil/solid mixture. The crude material was purified by flash chromatography using a biotage eluting with the solvent gradient 15% EtOAc/hexane to 50% EtOAc/hexane to afford the desired product (0.033 g, 60% yield) as a mixture of two isomers. The isomers were separated by HPLC on a Chiralcel AD column using 9/1 hexane/IPA to afford Examples 8a and 8b.

Electrospray MS [M+1]⁺ 536.2 for Example 8a.

Electrospray MS [M+1]⁺ 536.2 for Example 8b.

PREPARATION OF EXAMPLES 9a, 9b AND 9c

EXAMPLES 9a, 9b AND 9c

Example 9a

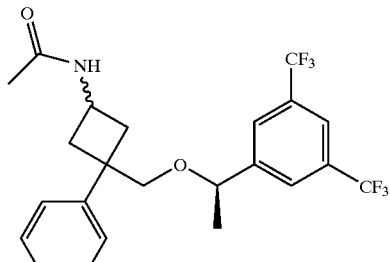

Example 9b

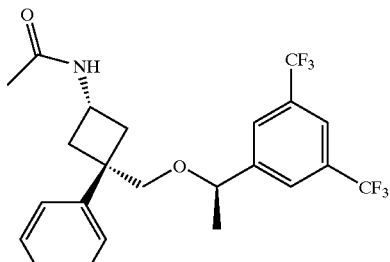

Example 9c

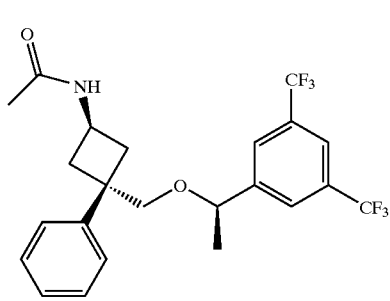

To Example 7 (0.1 g, 0.24 mmol, 1.0 equiv) in 1,2-dichloroethane (2 mL) under N₂ at 0° C. was added triethyl amine (0.61 g, 0.6 mmol, 2.5 equiv) followed by acetyl chloride (0.020 g, 0.26 mmol, 1.1 equiv). After 2 h at 0° C., the solution was concentrated under vacuo to afford the crude product as a white solid. The crude material was purified by flash chromatography using a biotage eluting with 70% EtOAc/hexane to afford Example 9a as a 1:1 diastereomeric mixture of isomers (0.102 g, 93% yield).

Separated 0.90 g of Example 9a by HPLC on a Chiralcel OD column using 9/1 hexane/IPA. Isomer A as Example 9b (0.042 g) and Isomer B as Example 9c (0.041 g) were obtained.

Electrospray MS [M+1]⁺ 460.1 for Example 9a.

Electrospray MS [M+1]⁺ 460.1 for Example 9b.

Electrospray MS [M+1]⁺ 460.1 for Example 9c.

PREPARATION OF EXAMPLES 10a AND 10b

EXAMPLE 10a

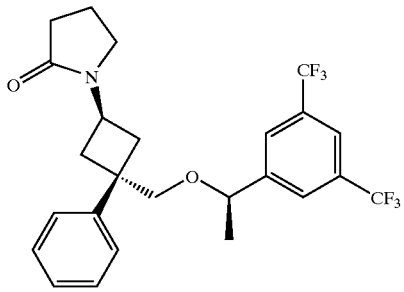

EXAMPLE 10b

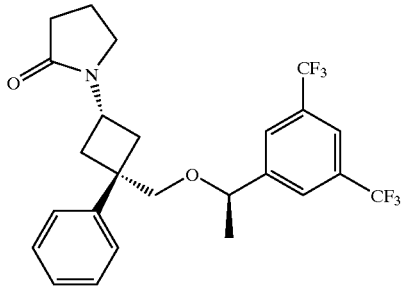

To Example 7 (0.097 g, 0.23 mmol, 1.0 equiv) in 1,2-dichloroethane (1.7 mL) under N₂ at 0° C. was added triethyl amine (0.81 mL, 0.58 mmol, 2.5 equiv) followed by 4-chlorobutyryl chloride (0.035 g, 0.25 mmol, 1.1 equiv). After 3 hours at 0° C., the reaction mixture was quenched with saturated NH₄Cl solution and diluted with CH₂Cl₂. The aqueous layer was extracted twice with CH₂Cl₂, dried over Na₂SO₄, filtered, and concentrated in vacuo to afford a colorless oil. The oil was diluted with anhydrous THF (2 mL) and cooled to 0° C. Sodium hydride as a 60% dispersion in mineral oil (0.019 g, 0.46 mmol, 2.0 equiv) was then added to the solution. The reaction mixture was allowed to warm to room temperature and stir for 14 h. The reaction was quenched with saturated NH₄Cl solution and diluted with EtOAc. The organic layer was washed once with brine, dried over Na₂SO₄, filtered, and concentrated in vacuo to afford a colorless oil. The crude material was purified by flash chromatography using a biotage eluting with 80% EtOAc/hexane to afford the desired product as mixture of isomers (0.090 g, 80% yield). Separated 0.90 g of the mixture by HPLC on a Chiralcel AD column using 9/1 hexane/IPA. Isomer A as Example 10a (0.034 g) and Isomer B as Example 10b (0.035 g) were obtained.

Electrospray MS [M+1]⁺ 486.1 for Example 10a.

Electrospray MS [M+1]⁺ 486.1 for Example 10b.

PREPARATION OF EXAMPLES 11a AND 11b

EXAMPLE 11a

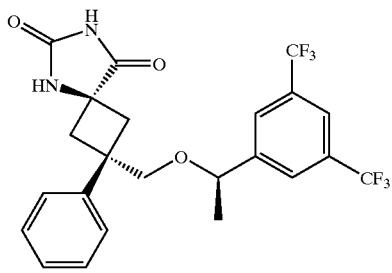

EXAMPLE 11b

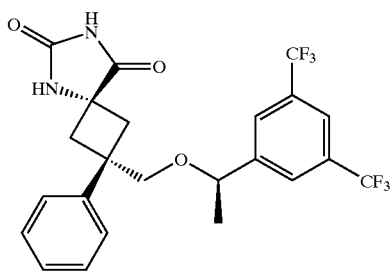

To Example 2 (1.35 g, 3.2 mmol, 1.0 equiv) in 50% EtOH (20 mL) was added KCN (0.42 g, 6.4 mmol, 2.0 equiv) and ammonium carbonate (1.25 g, 13 mmol, 4.0). The reaction mixture was heated in a steel bomb to 90° C. After 36 h, the bomb was allowed to cool to room temperature. The reaction mixture was diluted with EtOAc (200 mL). The organic layer was washed once with brine, dried over $Na_2SO_4$, filtered, and concentrated in vacuo to afford a white foam. The crude material was purified by flash chromatography using a biotage eluting with the solvent gradient 30% EtOAc/hexane to 40% EtOAc/hexane to afford Example 11a (0.71 g, 46% yield) as a white foam and Example 11b (0.66 g, 43% yield) as a white foam.

Electrospray MS [M+1]+ 487.1 for Example 11a.
Electrospray MS [M+1]+ 487.1 for Example 11b.

PREPARATION OF EXAMPLE 12a

EXAMPLE 12a

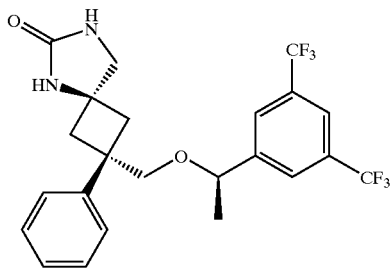

The title compound was prepared by a method analogous to Example 12b, using Example 11a in place of Example 11b.

Electrospray MS [M+1]+ 473.1 for Example 12a.

PREPARATION OF EXAMPLE 12b

EXAMPLE 12b

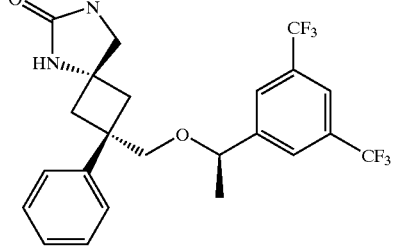

A flame-dried, 50 mL RBF under $N_2$ was charged with $AlCl_3$ (0.45 g, 3.4 mmol, 4.0 equiv). The solid was cooled to 0° C. in an ice bath and a 1M solution of $LiAlH_4$ (2.6 mL, 2.6 mmol, 3.0 equiv) in $Et_2O$ was added dropwise over 3 minutes. After 30 minutes, a solution of Example 11b (0.42 g, 0.86 mmol, 1.0 equiv) in dry THF (8 mL) was added via a cannula over a period of 2 minutes. After 1 h, the reaction mixture was allowed to warm to room temperature and was allowed to stir for an additional 24 h. The reaction mixture was cooled to 0° C. and quenched slowly with saturated sodium/potassium tartrate solution. After 1 h, the biphasic solution was diluted with EtOAc and the aqueous layer was extracted twice with EtOAc. The combined organics were washed once with brine, dried over $Na_2SO_4$, filtered, and concentrated in vacuo to afford the crude product as a white solid. The crude material was purified by flash chromatography using a biotage eluting with 90% EtOAc/hexane to afford the desired product (0.34 g, 84% yield) as white solid.

Electrospray MS [M+1]+ 473.1 for Example 12b.

PREPARATION OF EXAMPLE 13

EXAMPLE 13

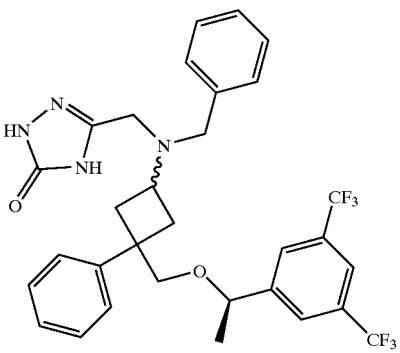

To a solution of Example 6 (0.4 g, 0.79 mmol, 1.0 equiv) and potassium carbonate (0.12 g, 0.87 mmol, 1.1 equiv) in DMF (1.0 mL) at 0° C. was added a solution of the chlorotriazolinone (0.1 g, 0.79 mmol, 1.0 equiv) in DMF (1.7 mL). After 5 h, an additional amount (0.01 g) of chlorotriazolinone was added to the reaction. After 4 h, the solution was concentrated in vacuo to afford a yellow oil.

The crude material was purified by flash chromatography using a biotage eluting with the solvent gradient 50% EtOAc/hexane (2% Et₃N) to 75% EtOAc/hexane (2% Et₃N) to afford a diastereomeric mixture of isomers Example 13 (0.3 g, 77% yield) as colorless oil.

Electrospray MS [M+1]⁺ 605.1 for Example 13.

PREPARATION OF EXAMPLE 14

EXAMPLE 14

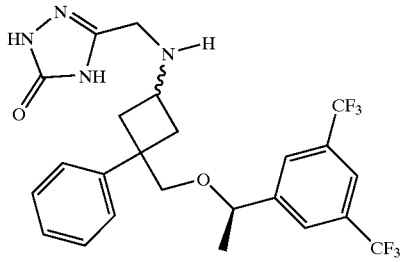

To Example 13 (0.31 g, 0.51 mmol, 1.0 equiv) in MeOH (5.0 mL) under N₂ was added 10% Pd/C (0.3 g) followed by ammonium formate (0.16 g, 2.6 mmol, 5.0 equiv). The reaction mixture was refluxed for one hour and then was allowed to cool to room temperature. The suspension was filtered through celite washing with EtOAc. The solution was concentrated in vacuo to afford a white solid (0.24 g, 92% yield) Example 14.

Electrospray MS [M+1]⁺ 515.1 for Example 14.

PREPARATION OF EXAMPLES 15a AND 15b

EXAMPLE 15a

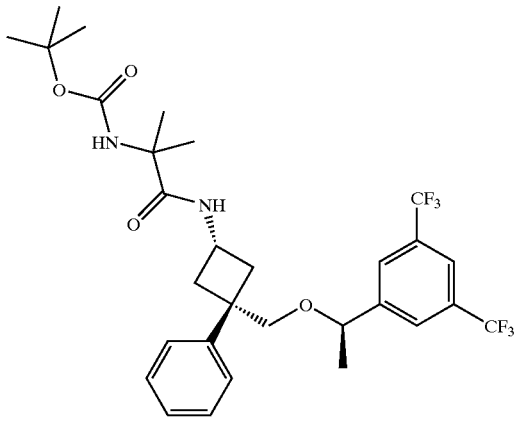

EXAMPLE 15b

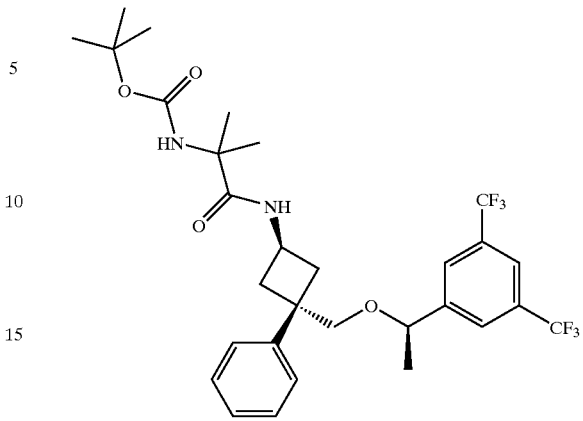

To a solution of Example 7 (0.47 g, 1.1 mmol, 1.0 equiv) in CH₂Cl₂ (5.5 mL) under N₂ was added Boc-α-methylalanine (0.1 g, 0.79 mmol, 1.0 equiv) followed by DCC (0.23 g, 1.1 mmol, 1.0 equiv). The reaction was complete after 18 h. The suspension was diluted with CH₂Cl₂ (20 mL) and filtered through a fritted-glass funnel. The reaction mixture was concentrated to afford a 0.74 g of a yellow solid. The crude material was purified by flash chromatography using a biotage eluting with the solvent gradient 25% EtOAc/hexane to 50% EtOAc/hexane to afford the desired product (0.56 g, 85% yield) as colorless oil. The isomers (0.56 g) were separated by HPLC on a Chiralcel OD column using 9/1 hexane/IPA. Isomer A as Example 15a (0.028 g) and Isomer B as Example 15b (0.021 g) were obtained.

Electrospray MS [M+1]⁺ 603.1 for Example 15a.
Electrospray MS [M+1]⁺ 603.2 for Example 15b.

PREPARATION OF EXAMPLE 16a

EXAMPLE 16a

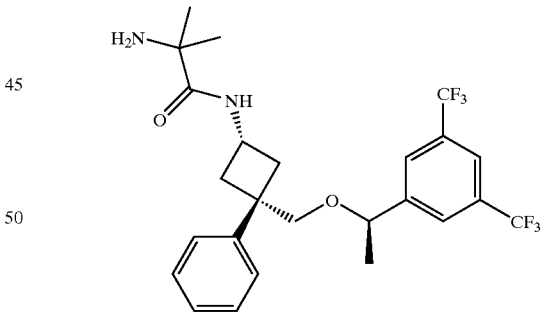

To a solution of Example 15a (0.26 g, 0.43 mmol, 1.0 equiv) in anhydrous CH₂Cl₂ (5.0 mL) under N₂ at 0° C. was added TFA (0.1 mL). The reaction mixture was monitored by TLC and showed a small amount of starting material after 4 hours. An excess amount of TFA (0.4 mL) was added and the reaction was allowed to warm to room temperature. After 2 h, the reaction mixture was cooled to 0° C., and quenched with saturated NaHCO₃ solution. The biphasic mixture was diluted with EtOAc, washed once with H₂O and brine, dried over Na₂SO₄, filtered, and concentrated in vacuo to afford Example 16a (0.22 g, 100% yield) as a colorless oil.

Electrospray MS [M+1]⁺ 503.2 for Example 16a.

PREPARATION OF EXAMPLE 16b

EXAMPLE 16b

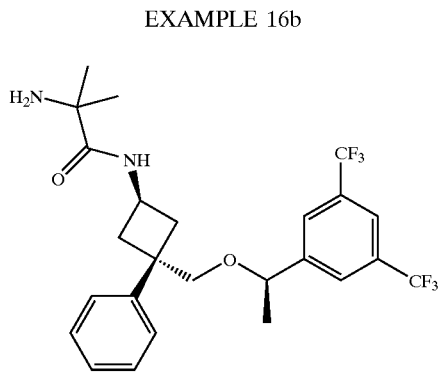

The title compound was prepared by a method analogous to Example 16a, using Example 15b.

Electrospray MS [M+1]⁺ 503.3 for Example 16b.

PREPARATION OF EXAMPLES 17a AND 17b

EXAMPLE 17a

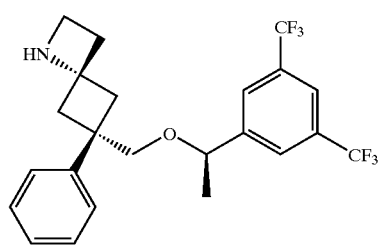

EXAMPLE 17b

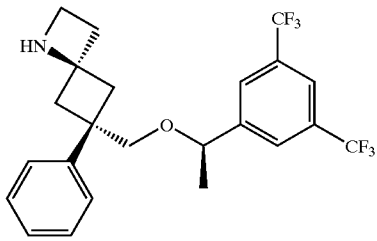

The title compounds were prepared by a method analogous to Example 12b, using Examples 8a and 8b. The isomers were separated by HPLC on a Chiralcel AD column using 9/1 hexane/IPA to afford Examples 17a and 17b.

Electrospray MS [M+1]⁺ 444.2 for Example 17a.

Electrospray MS [M+1]⁺ 444.2 for Example 17b.

PREPARATION OF EXAMPLE 18

EXAMPLE 18

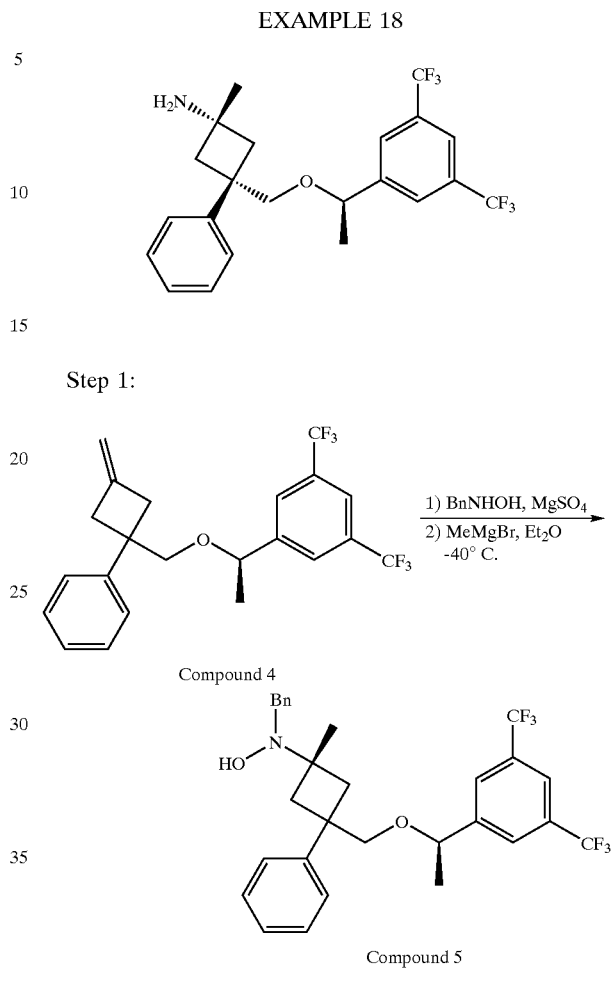

Step 1:

To Compound 4 (0.5 g, 1.2 mmol, 1.0 equiv) in anhydrous toluene (2 mL) was added sodium bicarbonate (0.092 g, 1.1 mmol, 0.95 equiv), N-benzyl hydroxylamine hydrochloride (0.18 g, 1.1 mmol, 0.95 equiv) and magnesium sulfate (0.05 g). The yellow suspension was allowed to stir for 4 hours, before being filtered and concentrated in vacuo to afford a yellow oil. The yellow oil was diluted with anhydrous ether (4 mL) and was cooled the solution to −78° C. Methyl magnesium bromide (0.43 mL, 1.3 mmol, 1.1 equiv) was added over 1 minute. The resulting yellow solution was allowed to warm to room temperature after 10 minutes. The reaction mixture was monitored by TLC and after 45 minutes indicated the presence of starting material. The solution was recooled to −78° C. and (0.43 mL) of MeMgBr was added. The cold bath removed after 10 minutes and the reaction mixture was allowed to stir for 2 h. The reaction mixture was cooled to 0° C. and quenched with saturated NH₄Cl solution and diluted with EtOAc. The organic layer was washed once with brine, dried over Na₂SO₄, filtered, and concentrated in vacuo to afford a yellow oil. The crude material was purified by flash chromatography using a biotage eluting with the solvent gradient 5% EtOAc/hexane to 40% EtOAc/hexane to afford Compound 5 (0.25 g, 38% yield).

Electrospray MS [M+1]⁺ 538.1 for Compound 5.

Step 2:

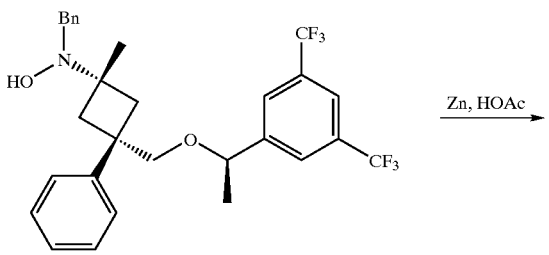

Compound 5

Compound 6

To a solution of Compound 5 (0.29 g, 0.54 mmol, 1.0 equiv) in acetic acid (3 mL) under $N_2$ was added zinc dust (0.35 g, 5.4 mmol, 10.0 equiv). The reaction mixture was heated to 70° C. After 30 minutes, the reaction mixture was allowed to cool to room temperature, filtered through celite, neutralized with 10% NaOH solution, and diluted with EtOAc. The organic layer was washed once with brine, dried over $Na_2SO_4$, filtered, and concentrated in vacuo to afford a colorless oil. The crude material was purified by flash chromatography using a biotage eluting with the solvent gradient 25% EtOAc/hexane to 75% EtOAc/hexane to 10% MeOH/EtOAc to afford Compound 6 (0.28 g, 100% yield).

Electrospray MS $[M+1]^+$ 522.1 for Compound 6.

Step 3:

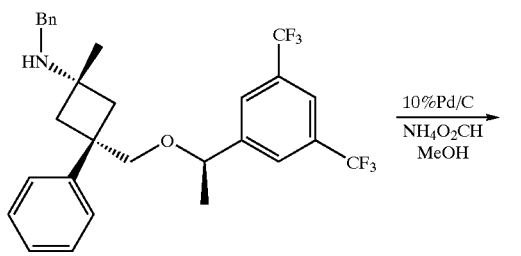

Compound 6

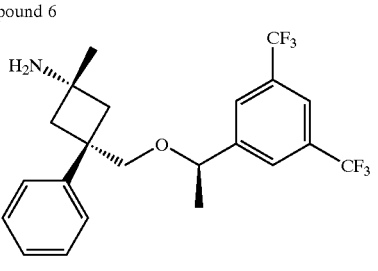

Example 18

To a solution of Compound 6 (0.13 g, 0.25 mmol, 1.0 equiv) in MeOH (5 mL) under $N_2$ was added 10% Pd/C (0.12 g) and ammonium formate (0.082 g, 1.3 mmol, 5.0 equiv). The reaction mixture was heated to reflux. After 1.5 h, the reaction mixture was allowed to cool to room temperature and the suspension was filtered through celite washing with EtOAc. The solution was concentrated in vacuo to afford Example 18 (0.097 g, 92% yield).

Electrospray MS $[M+1]^+$ 432.1 for Example 18.

PREPARATION OF EXAMPLE 19

EXAMPLE 19

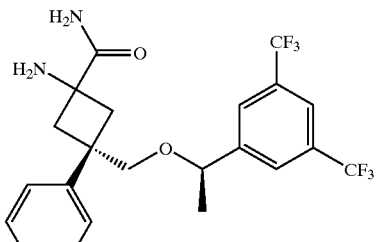

Step 1:

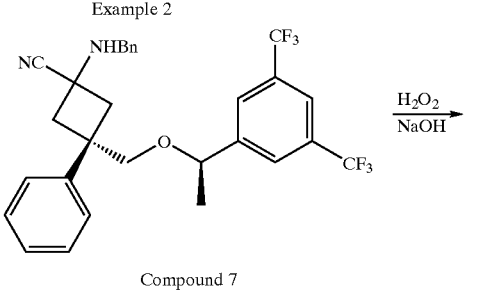

Example 2

Compound 7

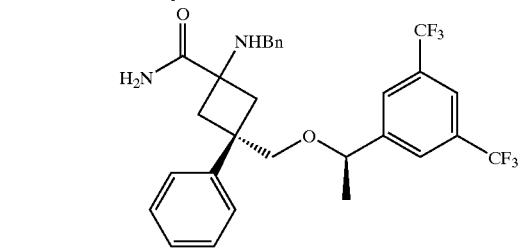

Compound 8

To Example 2 (0.21 g, 0.5 mmol, 1.0 equiv) in anhydrous MeOH (1.5 mL) under $N_2$ was added sodium cyanide (0.03 g, 0.6 mmol, 1.2 equiv) and benzylamine (0.07 g, 0.65 mmol, 1.3 equiv). The reaction mixture was cooled to 0° C. and acetic acid (70 µl) was added dropwise. The ice bath was removed after 30 minutes and the reaction was heated to reflux. After 19 h, the reaction mixture was quenched with saturated $NaHCO_3$ solution and diluted with EtOAc. The organic layer was washed twice with brine, dried over $Na_2SO_4$, filtered, and concentrated in vacuo to afford Compound 7 (0.26 g), a 1:1 mixture of diastereomers, as a yellow oil. To the crude Compound 7 (0.26 g, 0.49 mmol, 1.0 equiv) in EtOH (8 mL) was added a 1M NaOH solution (5 mL) followed by a dropwise addition of a 30% $H_2O_2$ solution over 10 minutes. After 4 h, the reaction was quenched with saturated NaHCO$_3$ solution and diluted with EtOAc. The organic layer was washed twice with brine, dried over Na$_2$SO$_4$, filtered, and concentrated in vacuo to afford Compound 8 (0.14 g, 50% yield) as a yellow oil.

Electrospray MS [M+1]$^+$ 551.1 for Compound 8.

Step 2:

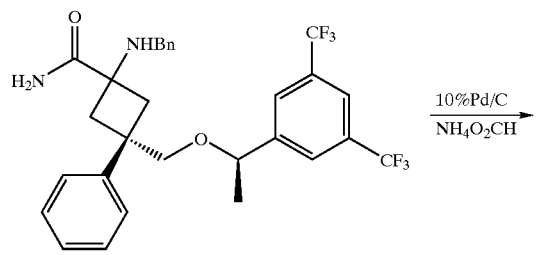

Compound 8

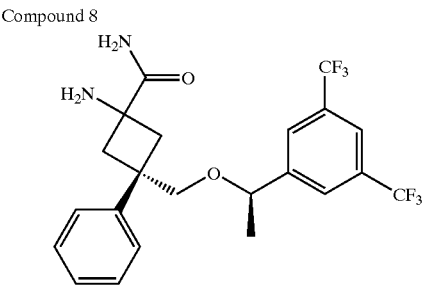

Example 19

To Compound 8 (0.114 g, 0.21 mmol, 1.0 equiv) in MeOH (4 mL) was added 10% Pd/C (0.11 g) followed by ammonium formate (0.069 g, 1.1 mmol, 5.0 equiv). After 3 h, the suspension was allowed to cool to room temperature and filtered through celite to afford a colorless oil (0.1 g). The crude material was purified on biotage eluting with 95:5 CH$_2$Cl$_2$/MeOH to afford a 1:1 diastereomeric mixture of Example 19 (0.044 g, 45% yield) as a colorless oil.

Electrospray MS [M+1]$^+$ 446.1 for Example 19.

PREPARATION OF EXAMPLE 20

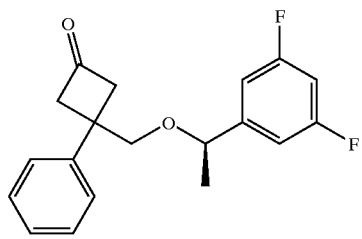

EXAMPLE 20

Step 1:

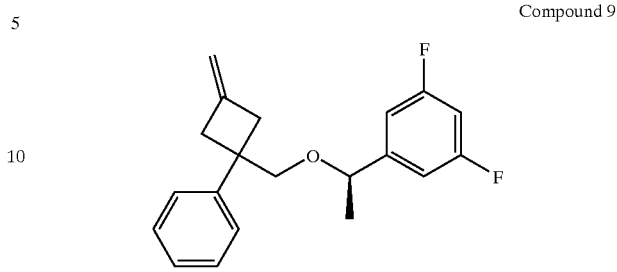

Compound 9

Compound 9 was prepared using similar procedure as for Compound 2 using 3,5-difluoromethylbenzyl alcohol instead of 3,5-bistrifluoromethylbenzyl alcohol.

Step 2:

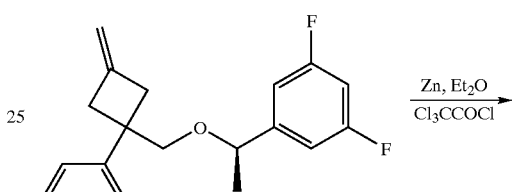

Compound 9

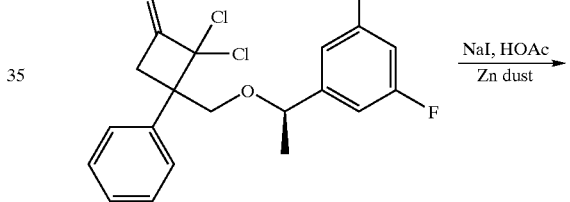

Compound 10

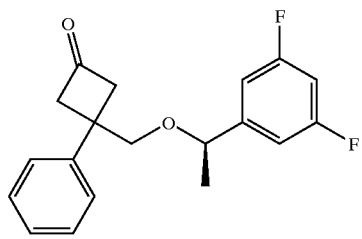

Example 20

To Compound 9 (1.73 g, 6.3 mmol, 1.0 equiv) in a flame-dried 100 mL RBF in anhydrous Et$_2$O (45 mL) was added zinc dust (0.83 g, 12.6 mmol, 2.0 equiv). An addition funnel containing a solution of trichloroacetylchloride (1.1 mL, 9.46 mmol, 1.5 equiv) in anhydrous Et$_2$O (20 mL) was attached on top of the reaction flask which was emerged in the water bath of a sonicater to the level where it experienced the maximum agitation. The solution was added dropwise over a period of 50 minutes. After the addition was complete, the reaction mixture was sonicated vigorously for an additional 5 h. The TLC (EtOAc/Hexane=10%) indicated the presence of starting material and an additional portion of trichloroacetylchloride (0.8 mL, 7.17 mmol, 1.1 equiv) was added over 10 minutes. The reaction mixture was sonicated for another 6 h. The reaction was almost complete by TLC and the solvent was evaporated in vacuo. The crude product, mainly Compound 10 and zinc dust, was treated with HOAc (30 mL), zinc dust (3.3 g, 50.5 mmol, 8 equiv) and NaI (1.88 g, 12.5 mmol, 2.0 equiv). The black mixture was heated at 90° C. for 1 hour. The TLC (EtOAc/Hexane=10%) showed the Compound 10 was almost completely consumed. The reaction mixture was diluted with EtOAc and the dark brown solution was filtered through a fritted funnel containing celite and was washed thoroughly with EtOAc. The filtrate was cooled to 0° C. and neutralized carefully with saturated NaHCO₃ aqueous solution, separated, and the aqueous layer was further extracted with EtOAc. The combined organic layers were washed with brine, dried over Na₂SO₄, filtered, and concentrated in vacuo to afford the crude product. The crude material was purified by flash chromatography using a biotage to afford Example 20 (0.43 g, 21% yield).

EXAMPLE 20

$^1$H NMR (500 MHz, CDCl₃) δ 1.37 (d, J=6.305 Hz, 3H), 3.35–3.43 (m, 4H), 3.48 (s, 2H), 4.25 (q, J=6.305 Hz, 1H), 6.62–6.68 (m, 3H), 7.25–7.39 (m, 5H).

PREPARATION OF EXAMPLES 21a AND 21b

EXAMPLE 21a

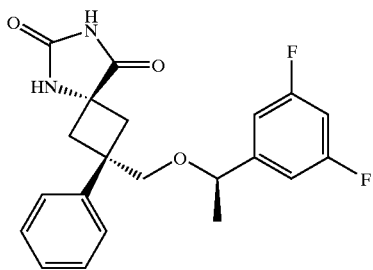

EXAMPLE 21b

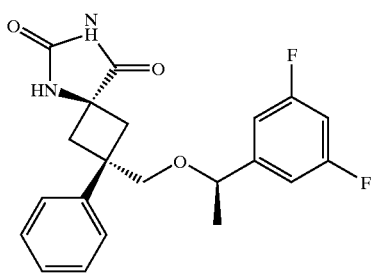

A solution of Example 20 (0.38 g, 1.2 mmol, 1.0 equiv) in EtOH/H₂O (v/v=1/1) (2.25 mL) was treated with (NH₄)₂CO₃ (0.34 g, 4.43 mmol, 3.7 equiv) and KCN (0.12 g, 1.90 mmol, 1.58 equiv). The resulting orange solution was heated to 60° C. for 36 h. The reaction mixture was diluted with water, and carefully extracted with EtOAc. The combined organic layers were dried over Na₂SO₄, filtered, and concentrated in vacuo to give the crude product. The crude material was purified on a biotage eluting with the solvent gradient 10% EtOAc/hexane to 30% EtOAc/hexane to afford a mixture of diastereomers, which was further purified on a Chiralcel OD column (IPA/hexane=10/90) to obtain Examples 21a and 21b.

Electrospray MS [M+1]⁺ 387.1 Example 21a.
Electrospray MS [M+1]⁺ 387.1 Example 21b.

PREPARATION OF EXAMPLES 22a AND 22b

EXAMPLE 22a

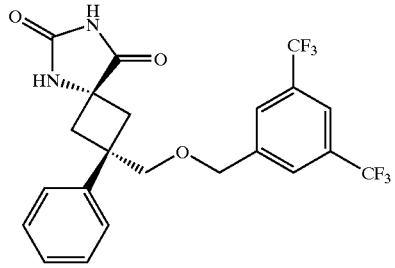

EXAMPLE 22b

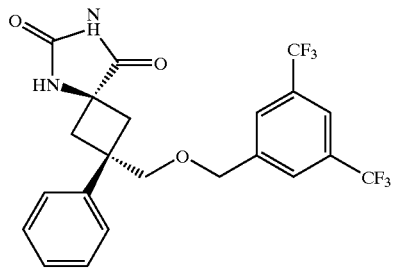

Step 1:

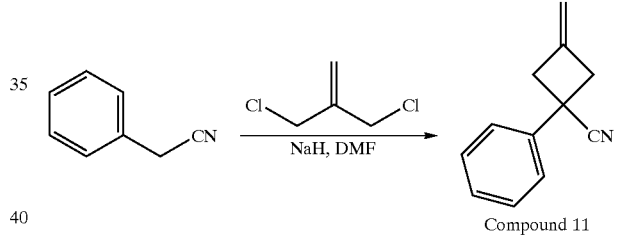

A three-necked RBF under N₂ was charged with anhydrous DMF (1L), 1,3-dichloro-2-butene (30 mL, 0.259 mmol) and a 60% dispersion of NaH in mineral oil (30.6 g). To the above suspension under vigorous stirring was added dropwise benzylcyanide (30.45 mL) in anhydrous DMF (30 mL) over 15 minutes. After 30 minutes, the reaction was quenched with saturated NH₄Cl and extracted with ether. The organic layer was washed with water, brine, dried with Na₂SO₄ filtered, and concentrated in vacuo. The crude product was purified using a flash silica gel column to afford Compound 11 (10–15 g, 23–35% yield).

Step 2:

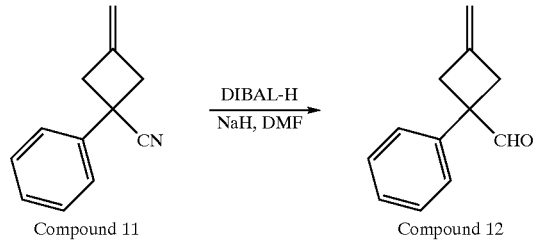

A flame-dried 250 mL flask containing a 1.0 M solution of DIBAL-H in hexane (60 mL, 60 mmol, 2.0 equiv) was diluted with anhydrous THF (15 mL) and cooled to −50° C. To this solution was added via cannula a solution of Compound 11 (5 g, 30 mmol, 1.0 equiv) in dry THF (10 mL). After 3 h at −50° C., the reaction was quenched with saturated NH$_4$Cl and was allowed to stir at room temperature for 30 minutes. The layers were separated and the aqueous layer was further extracted with EtOAc. The organic layers were combined and concentrated in vacuo. The crude product was purified using a silica plug, eluting with EtOAc to afford Compound 12 (4.31 g, 83% yield).

Step 3:

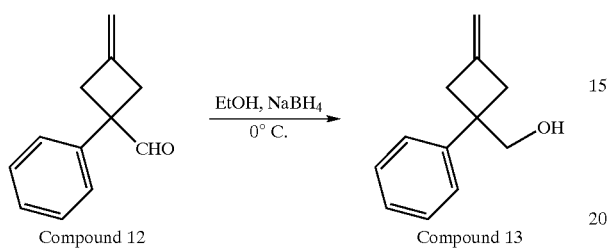

Compound 12          Compound 13

A solution of Compound 12 (4.31 g, 25 mmol, 1.0 equiv) in absolute EtOH (50 mL) was cooled to 0° C. and treated with NaBH$_4$ (1.89 g, 50 mmol, 2.0 equiv). The reaction mixture was quenched with MeOH after stirring for one hour, then concentrated in vacuo to dryness. The residue was taken up in ether and washed with saturated sodium bicarbonate and brine. The organic layers were combined, dried over Na$_2$SO$_4$, filtered, and concentrated in vacuo to give the crude product which was purified via flash chromatography using a biotage to give Compound 13 (3.81 g, 87% yield).

Step 4:

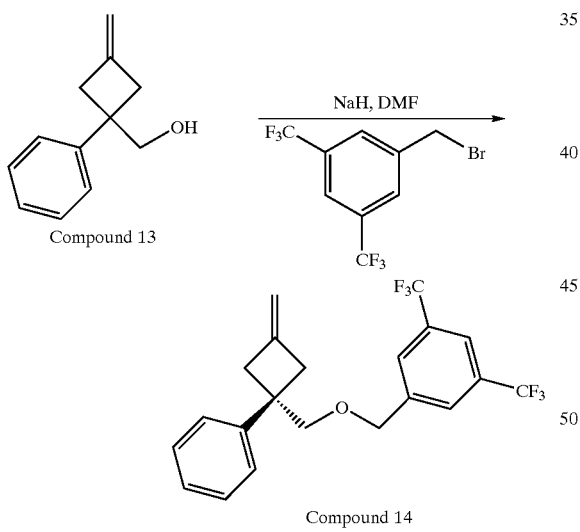

Compound 13

Compound 14

A solution of Compound 13 (2.5 g, 14.4 mmol) in DMF (50 mL) was cooled to 0° C. and treated with a 60% dispersion of NaH in mineral oil (1.0 g, 25.2 mmol). After stirring for 10 minutes, 3,5-bistrifluoromethylbenzylbromide (4.7 mL, 23 mmol) was added dropwise and the solution was allowed to warm to 23° C. After 18 h, the reaction was quenched with saturated NH$_4$Cl and taken up in ether. The organic layers were combined washed with water and brine, dried over Na$_2$SO$_4$, filtered, and concentrated in vacuo to give the crude product which was purified by flash chromatography using a biotage to give Compound 14 (5.45 g, 95% yield).

Step 5:

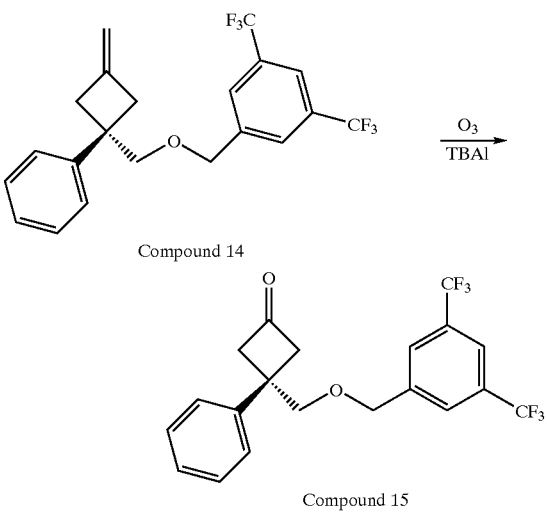

Compound 14

Compound 15

A solution of Compound 14 (1.7 g, 4.25 mmol, 1.0 equiv) in CH$_2$Cl$_2$ (42 mL) was cooled to −78° C. and treated with O$_3$. After 1 h, the reaction mixture was quenched with tetrabutylammonium iodide (1.88 g, 5.1 mmol) and was allowed to warm to 23° C. The solution was concentrated in vacuo and the crude product was purified by flash chromatography using a biotage to give Compound 15 (0.85 g, 49%).

Step 6:

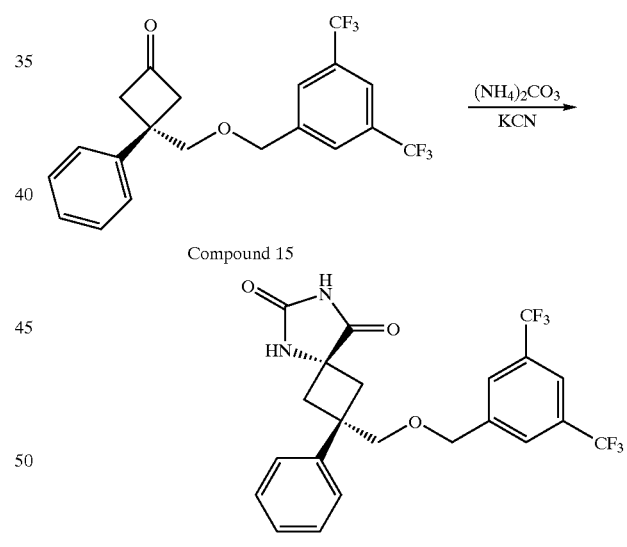

Compound 15

Example 22a

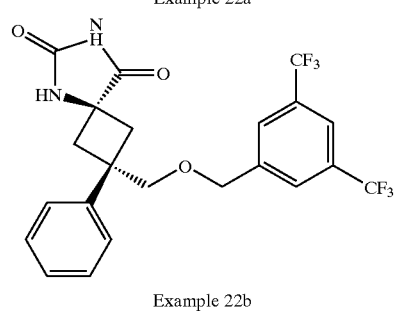

Example 22b

To a solution of Compound 15 (0.85 g, 2.1 mmol, 1.0 equiv) in EtOH—H$_2$O(4:1; v/v) (10 mL) was added (NH$_4$)$_2$CO$_3$ (0.7 g, 7.3 mmol, 3.5 equiv) and KCN (0.25 g, 3.8 mmol, 1.8 equiv). The reaction vessel was sealed and heated at 90° C. for 12 hours. The EtOH was then removed under reduced pressure and residue was partitioned between water and EtOAc. The organic layer was washed with brine, dried over Na$_2$SO$_4$, filtered, and concentrated in vacuo. The crude product was purified using a silica gel column to give (0.62 g, 62% yield) Examples 22a and 22b.

Electrospray MS [M+1]$^+$ 473.1 for Example 22a.

Electrospray MS [M+1]$^+$ 473.1 for Example 22b.

PREPARATION OF EXAMPLES 23a AND 23b

EXAMPLE 23a

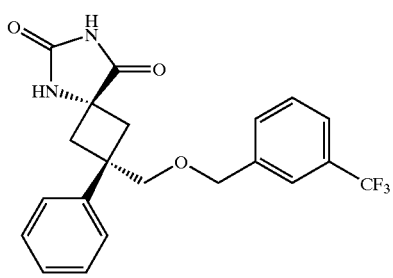

EXAMPLE 23b

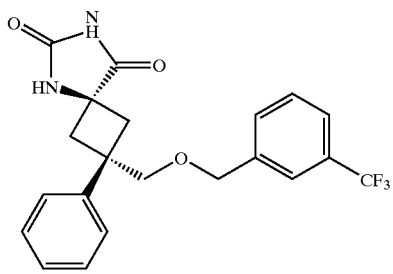

Step 1:

Compound 16

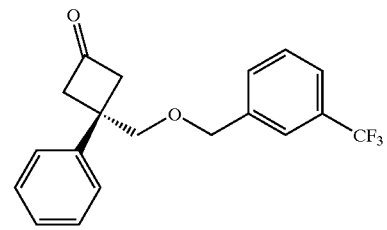

Compound 16 was prepared using a similar procedure as for Compound 2 using 3-trifluoromethylbenzyl alcohol instead of 3,5-bistrifluoromethylbenzyl alcohol.

Step 2:

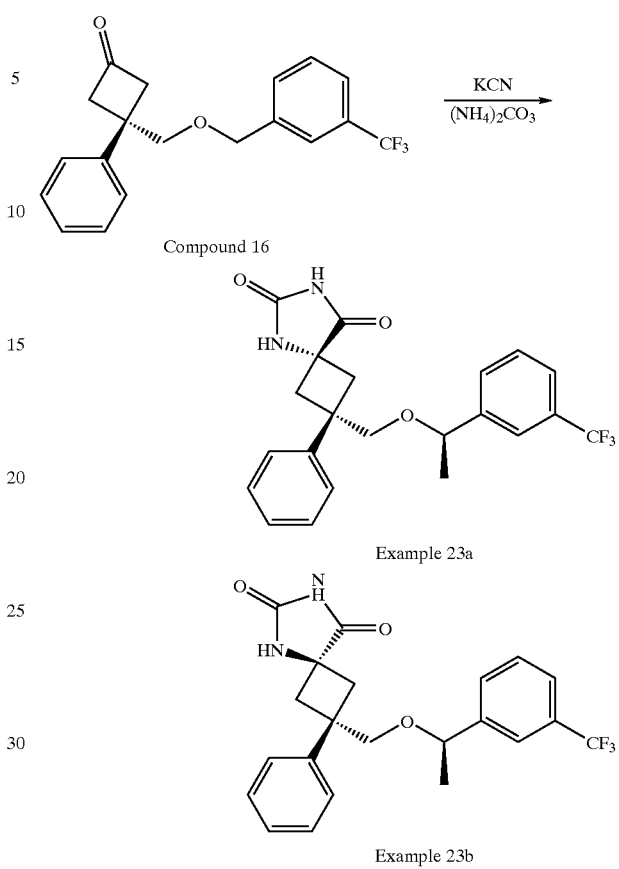

Examples 23a and 23b were prepared using similar procedure as for Examples 11a and 11b using Compound 16 instead of Compound 2.

EXAMPLE 23a $^1$H NMR(500 MHz, CDCl$_3$) δ 7.47–7.15 (m, 9H); 5.69 (s, 1H); 4.38 (dd, 1H); 3.84, (d, 1H); 3.54 (d, 1H); 3.14 (m, 1H); 3.03 (m, 1H); 2.67 (m, 2H); 1.34 (d,1H).

EXAMPLE 23b $^1$H NMR(500 MHz, CDCl$_3$) δ 7.54 (m, 4H); 7.48 (m, 3H); 7.00 (m, 2H); 6.53 (s, 1H); 4.53 (m, 1H); 3.25, (m, 2H); 3.10 (m, 2H); 2.76 (dd, 1H); 2.65 (dd, 1H); 1.61 (d, 1H)

PREPARATION OF EXAMPLE 24

EXAMPLE 24

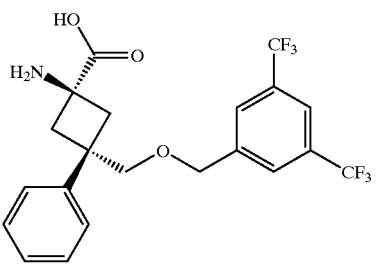

In a sealed tube, Example 22b (0.120 g, 0.254 mmol, 1.0 equiv) was dissolved in MeOH (2 mL) and water (3 mL) and was treated with a 50% aqueous solution NaOH (0.5 mL). The suspension was sealed and heated at 100–110° C. for 20 hours. The volatiles were blown away with $N_2$ at 100° C. The residue was diluted with MeOH (10 mL) and neutralized with 1M HCl in ether to pH 7. The mixture was filtered and the residue was washed with MeOH. The filtrate was concentrated in vacuo and the resulting residue was diluted with water and EtOAc. The aqueous layer was further extracted twice with EtOAc. The combined organic layers were dried over $Na_2SO_4$, filtered, and concentrated in vacuo to give the crude product. The material was dissolved in DMSO and subjected to Gilson (RP C18) to provide Example 24 (0.064 g, 56% yield).

Electrospray MS [M+1]$^+$ 448.1 for Example 24.

PREPARATION OF EXAMPLE 25

EXAMPLE 25

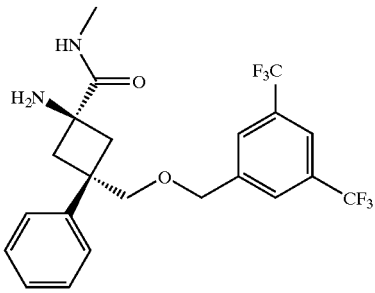

To a solution Example 24 (0.056 g, 0.123 mmol, 1.0 equiv) in DMF (1 mL), was added a 2.0 M solution of methylamine in MeOH (0.135 mL, 0.27 mmol, 2.2 equiv) followed by the addition of HATU (0.052 g, 1.35 mmol, 11 equiv). The reaction mixture was allowed to stir at 23° C. overnight. The reaction mixture was diluted with DMF (1 mL) and subjected to separation by Gilson (RP C18) to give Example 25 (0.001 g, 2% yield).

Electrospray MS [M+1]$^+$ 461.1 for Example 25.

PREPARATION OF EXAMPLES 26a AND 26b

EXAMPLE 26a

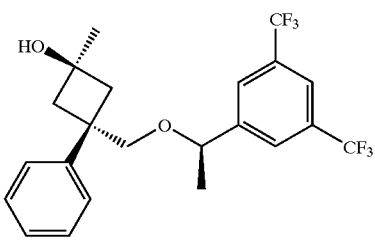

EXAMPLE 26b

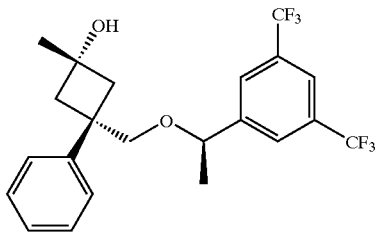

To a solution of Example 2 (0.39 g, 0.93 mmol, 1.0 equiv) in dry ether (10 mL) at –78° C. was added methylmagnesium bromide (0.34 mL, 1.005 mmol, 1.07 equiv). After 10 minutes at –78° C., the reaction mixture was allowed to warm to room temperature. After 16 h, no progress in the reaction was observed by TLC. The solution was cooled to –78° C. and methylmagnesium bromide (1.0 equiv) was added. The solution was allowed to warm to room temperature and stir for 5 h. The reaction mixture was quenched with saturated $NaHCO_3$ solution (20 mL) and was extracted with EtOAc (2×100 mL). The combined organic layers were dried over $Na_2SO_4$, filtered, and concentrated in vacuo. The crude product was purified by flash chromatography using a biotage eluting with the solvent gradient 95:5 hexane/EtOAc to 9:1 hexane/EtOAc to afford a mixture of two isomers (0.2 g, 50% yield). The isomers were separated by HPLC using a semi-prep Chiralcel OD column (IPA/hexane=10/90) to afford Examples 26a and 26b.

Electrospray MS [M–17]$^+$ 451.1 for Example 26a.

Electrospray MS [M+1]$^+$ 433.1 for Example 26b.

PREPARATION OF EXAMPLE 27

EXAMPLE 27

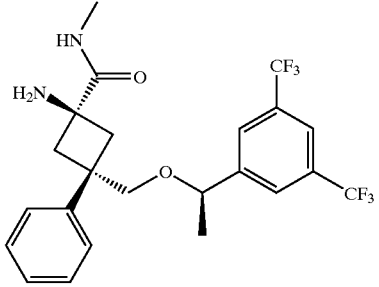

Step 1:

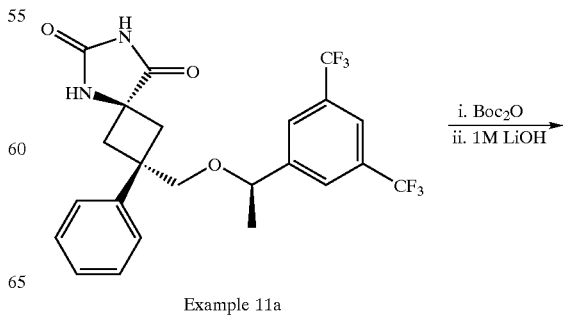

Example 11a

-continued

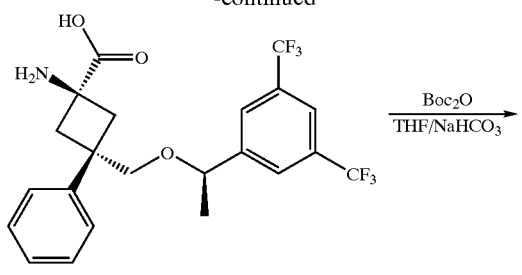

Compound 17

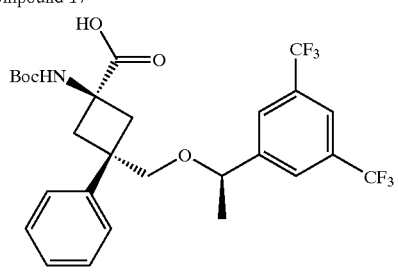

Compound 18

To a solution of Example 11a (7.5 g, 15.4 mmol, 1.0 equiv) in anhydrous THF (200 mL) under N₂ was added di-tert-butyl dicarbonate (6.7 g, 30.8 mmol, 2.0 equiv) and catalytic DMAP (50 mg, 0.41 mmol, 0.03 equiv). After 3 hours, 1M LiOH solution (150 mL) was added to the reaction mixture and the resulting suspension was allowed to stir for 24 h. The reaction mixture was diluted with water (200 mL) and EtOAc (700 mL). The organic layer was washed with brine, dried over Na₂SO₄, filtered, and concentrated in vacuo to afford Compound 17 (10.5 g, >100% yield) as a yellow foam. [Note: The crude material was carried forward based on a quantitative yield from the first step.] To a solution of Compound 18 (7.1 g, 15.4 mmol, 1.0 equiv) in THF (80 mL) and saturated aqueous NaHCO₃ solution was added di-tert-butyl dicarbonate (8.4 g, 38.5 mmol, 2.5 equiv). After 24 h, the solution was cooled to 0° C. and was acidified with 10% citric acid solution to ph 3–4. The solution was extracted with EtOAc (700 mL). The organic layer was washed once with water and brine, dried over Na₂SO₄, filtered, and concentrated in vacuo to afford a foam (11.4 g). The crude product was purified by flash chromatography using a biotage eluting with 7% MeOH/CH₂Cl₂ to afford Compound 18 (7.6 g, 88% yield) as a white solid foam.

Electrospray MS [M+1]⁺ 562.1 for Compound 18.

Step 2:

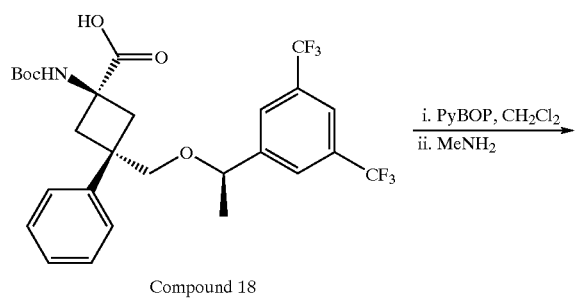

Compound 18

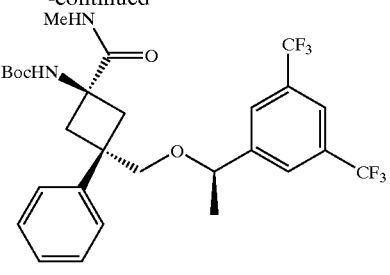

Compound 19

To a solution of Compound 18 (5.0 g, 8.9 mmol, 1.0 equiv) in anhydrous CH₂Cl₂ (100 mL) under N₂ at 0° C. was added diisopropylethylamine (4.6 mL, 26.7 mmol, 3.0 equiv) and PyBOP (5.1 g, 9.8 mmol, 1.1 equiv). After 30 minutes the ice bath was removed and the solution was allowed to stir for 1 h at room temperature. A 2M solution of methylamine in THF (44 mL, 89 mmol, 10 equiv) was added to the reaction mixture and the resulting suspension was allowed to stir for 24 h. The reaction was quenched with water and diluted with EtOAc (400 mL). The organic layer was washed twice with brine, dried over Na₂SO₄, filtered, and concentrated in vacuo to afford a yellow foam (8.5 g). The crude product was purified by flash chromatography using a biotage eluting with the solvent gradient 30% EtOAc/hexane to 40% EtOAc/hexane to 50% EtOAc/hexane to afford Compound 19 (4.2 g, 82% yield) as a white solid foam.

Electrospray MS [M+1]⁺ 575.1 for Compound 19.

Step 3:

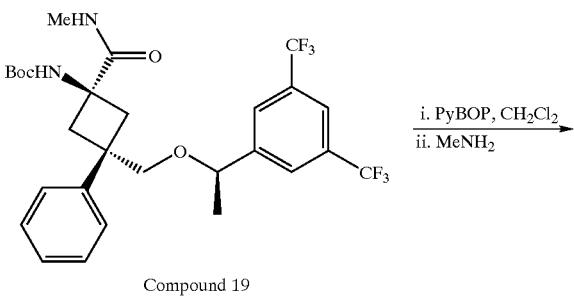

Compound 19

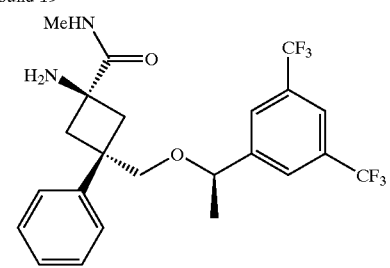

Example 27

To a solution of Compound 19 (3.0 g, 5.2 mmol, 1.0 equiv) in anhydrous CH₂Cl₂ (35 mL) under N₂ at was added excess TFA (4.0 mL, 52 mmol, 10 equiv). After 24 h, the reaction mixture was cooled to 0° C. and quenched with saturated NaHCO₃ solution. The biphasic mixture was diluted with EtOAc, washed once with brine, dried over Na₂SO₄, filtered, and concentrated in vacuo to afford Example 27 (2.4 g, 98% yield) as a colorless gum.

Electrospray MS [M+1]⁺ 475.1 for Example 27.

PREPARATION OF EXAMPLE 28

EXAMPLE 28

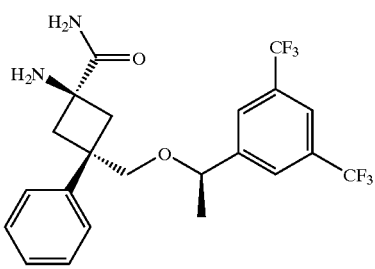

The title compound was prepared by a method analogous to Example 27 from Compound 18, using ammonia gas in place of methylamine.

Electrospray MS [M+1]$^+$ 461.1 for Example 28.

PREPARATION OF EXAMPLE 29

EXAMPLE 29

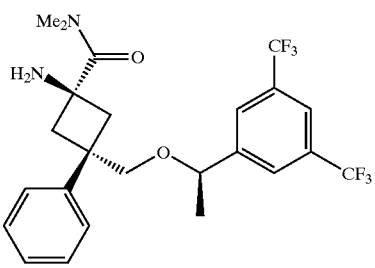

Step 1:

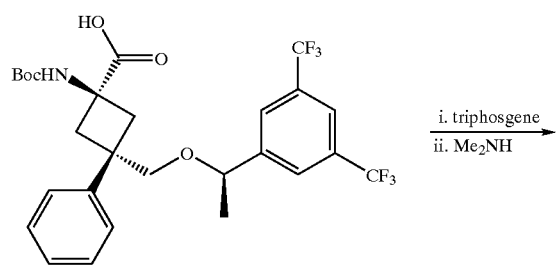

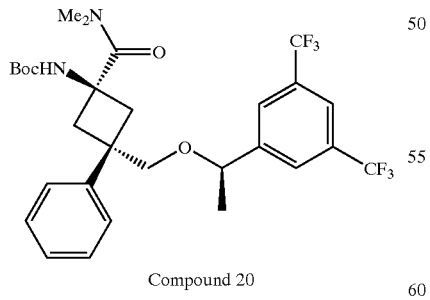

To a solution of Compound 18 (0.15 g, 0.27 mmol, 1.0 equiv) in anhydrous CH$_2$Cl$_2$ (2 mL) under N$_2$ was added diisopropylethylamine (0.14 mL, 0.81 mmol, 3.0 equiv) and triphosgene (0.040 g, 0.14 mmol, 0.5 equiv). After 3 h, a 2M solution of dimethylamine in THF (0.7 mL, 1.4 mmol, 5 equiv) was added to the reaction mixture and the resulting suspension was allowed to stir for 60 h. The reaction was quenched with water and diluted with EtOAc (25 mL). The organic layer was washed twice with brine, dried over Na$_2$SO$_4$, filtered, and concentrated in vacuo to afford a yellow foam (0.094 g). The crude product was purified by flash chromatography using a biotage eluting with 30% EtOAc/hexane to afford Compound 20 (0.036 g, 23% yield) as a white solid.

Electrospray MS [M+1]$^+$ 589.1 for Compound 20.

Step 2:

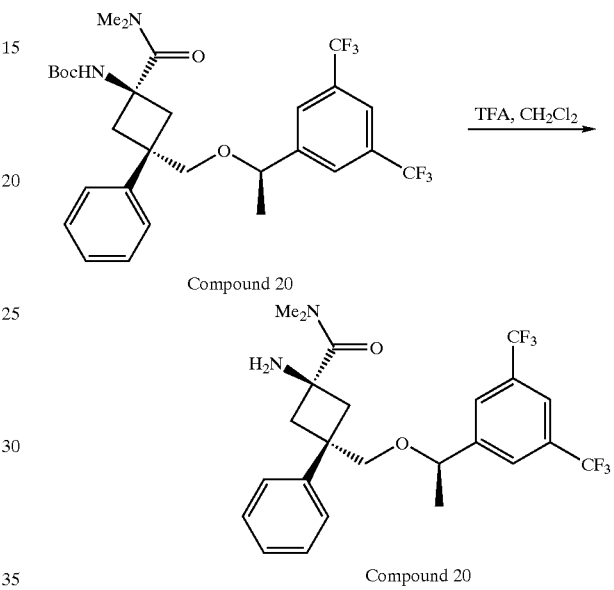

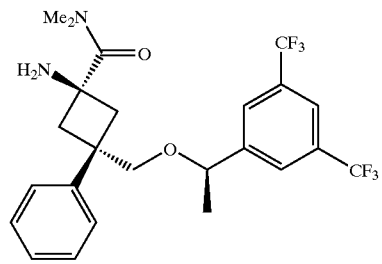

Example 29 was prepared from Compound 20 by a method analogous to Example 27 from Compound 19.

Electrospray MS [M+1]$^+$ 489.1 for Example 29.

PREPARATION OF EXAMPLE 30

EXAMPLE 30

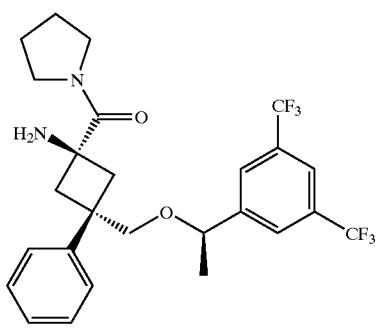

The title compound was prepared by a method analogous to Example 29 from Compound 18, using pyrrolidine in place of dimethylamine.

Electrospray MS [M+1]$^+$ 515.1 for Example 30.

PREPARATION OF EXAMPLE 31

EXAMPLE 31

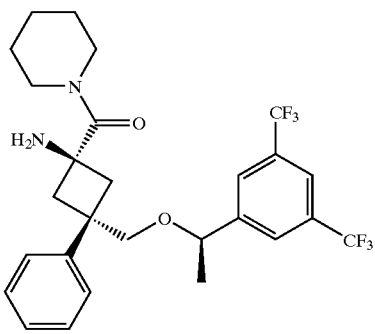

The title compound was prepared by a method analogous to Example 29 from Compound 18, using piperidine in place of dimethylamine.

Electrospray MS [M+1]$^+$ 529.1 for Example 31.

PREPARATION OF EXAMPLE 32

EXAMPLE 32

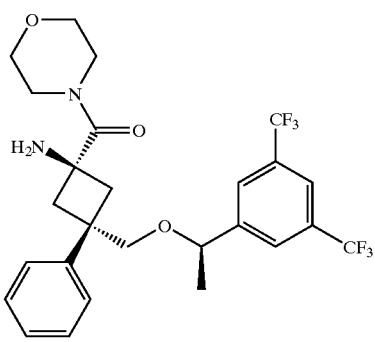

The title compound was prepared by a method analogous to Example 29 from Compound 18, using morpholine in place of dimethylamine.

Electrospray MS [M+1]$^+$ 531.1 for Example 32.

PREPARATION OF EXAMPLE 33

EXAMPLE 33

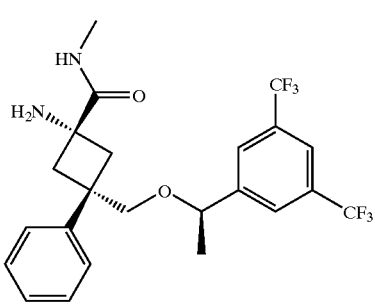

The title compound was prepared from Example 11b by a method analogous to Example 27 from Example 11a.

Electrospray MS [M+1]$^+$ 475.3 for Example 33.

PREPARATION OF EXAMPLE 34

EXAMPLE 34

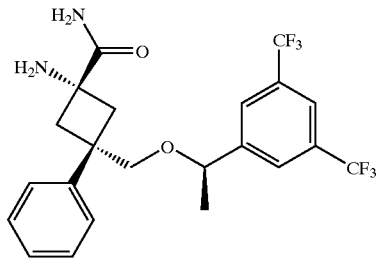

The title compound was prepared from Example 11b by a method analogous to Example 27 from Example 11a.

Electrospray MS [M+1]$^+$ 461.3 for Example 34.

PREPARATION OF EXAMPLE 35

EXAMPLE 35

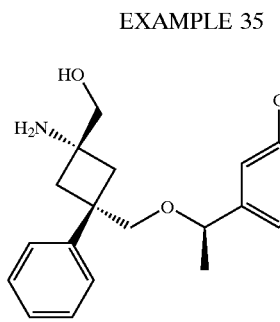

Step 1:

Compound 21

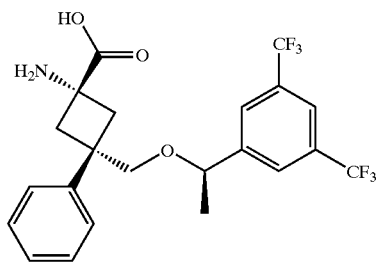

Compound 21 was prepared from Example 11b by a method analogous to Compound 17 from Example 11a.

Electrospray MS [M+1]$^+$ 462.1 for Compound 21.

Step 2:

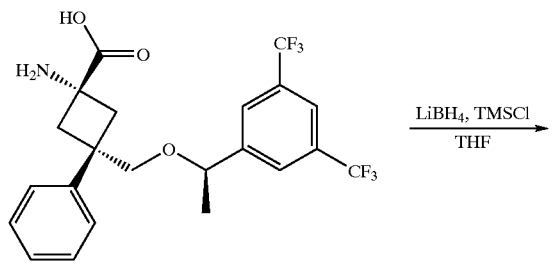

Compound 21

PREPARATION OF EXAMPLE 37

EXAMPLE 37

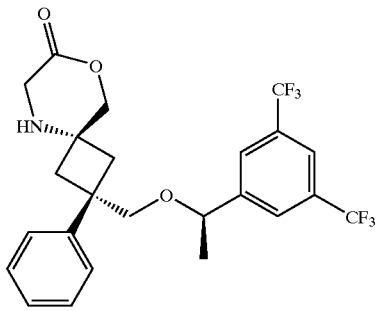

Example 35

To a solution of lithium borohydride (0.033 g, 1.5 mmol, 2.0 equiv) in anhydrous THF (1.0 mL) under $N_2$ was added TMSCl (0.39 mL, 3.0 mmol, 4.0 equiv). After 10 minutes, a solution of Compound 21 (0.0035 g, 0.76 mmol, 1.0 equiv) in anhydrous THF (2 mL) was cannulated into the reaction flask over 8 minutes. After 4 h, the solution was cooled to 0° C. and carefully quenched with MeOH (1 mL) and 1M KOH solution (1 mL). The reaction mixture was diluted with EtOAc (40 mL), washed once with brine, dried over $Na_2SO_4$, filtered, and concentrated in vacuo to afford Example 35 (0.31 g, 91% yield) as a colorless gum.

FAB MS $[M+1]^+$ 448.3 for Example 35.

PREPARATION OF EXAMPLE 36

EXAMPLE 36

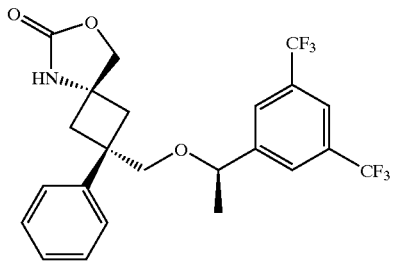

To a solution of Example 35 (0.12 g, 0.27 mmol, 1.0 equiv) in anhydrous $CH_2Cl_2$ (2 mL) under $N_2$ was added diisopropylethylamine (0.24 mL, 1.4 mmol, 5.0 equiv) and triphosgene (0.042 g, 0.14 mmol, 0.5 equiv). After 4 h, the reaction mixture was concentrated in vacuo to afford a yellow foam (0.2 g). The crude product was purified by flash chromatography using a biotage eluting with the solvent gradient 10% EtOAc/hexane to 50% EtOAc/hexane to afford Example 36 (0.10 g, 78% yield) as a white solid.

Electrospray MS $[M+1]^+$ 474.1 for Example 36.

To a solution of Example 35 (0.14 g, 0.31 mmol, 1.0 equiv) in $CH_3CN$ (3 mL) under $N_2$ was added diisopropylethylamine (0.13 mL, 0.78 mmol, 2.5 equiv) and a solution of phenyl bromoacetate (0.073 g, 0.34 mmol, 1.1 equiv) in $CH_3CN$ (1 mL). After 24 h, the reaction mixture was concentrated in vacuo to afford a colorless oil (0.2 g). The crude product was purified by flash chromatography using a biotage eluting with the solvent gradient 20% EtOAc/hexane to 80% EtOAc/hexane to afford Example 37 (0.10 g, 68% yield).

FAB MS $[M+1]^+$ 488.2 for Example 37.

PREPARATION OF EXAMPLE 38

EXAMPLE 38

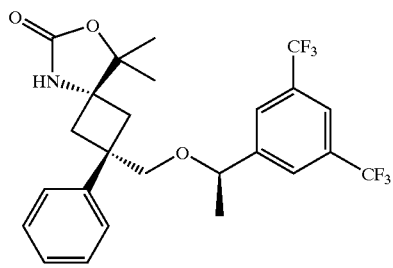

Step 1:

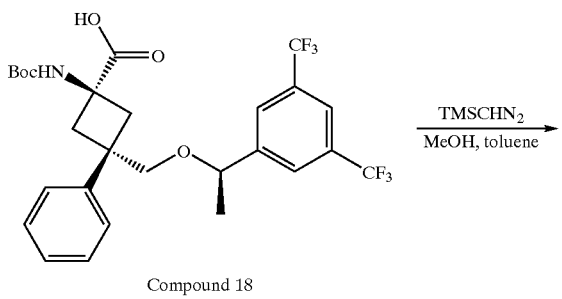

Compound 18

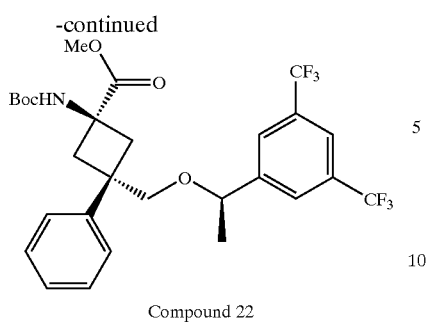

Compound 22

To a solution of Compound 18 (0.20 g, 0.36 mmol, 1.0 equiv) in MeOH (1.2 mL) and toluene (3.0 mL) under $N_2$ at 0° C. was added a 2.0M solution of trimethylsilyl diazomethane in hexane (0.9 mL, 1.8 mmol, 5.0 equiv). After 30 minutes, the reaction mixture was concentrated in vacuo to afford a yellow oil (0.2 g). The crude product was purified by flash chromatography using a biotage eluting with the solvent gradient 10% EtOAc/hexane to 25% EtOAc/hexane to afford Compound 22 (0.10 g, 47% yield).

Electrospray MS $[M+1]^+$ 576.1 for Compound 22.

Step 2:

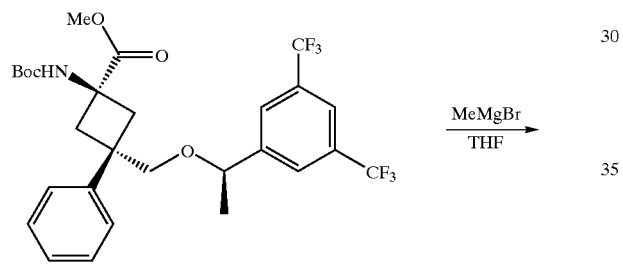

Compound 22

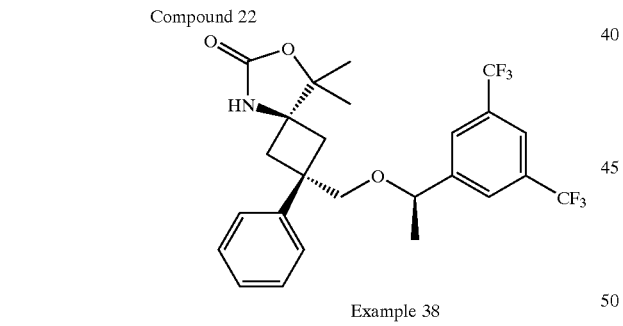

Example 38

To a solution of Compound 22 (0.10 g, 0.17 mmol, 1.0 equiv) in THF (2 mL) under $N_2$ at 0° C. was added a 3.0 M solution of MeMgBr in $Et_2O$ (0.14 mL, 0.41 mmol, 2.4 equiv). The reaction mixture was slowly allowed to warm to room temperature. After 24 h, the reaction mixture was cooled to 0° C. and quenched with saturated $NH_4Cl$ solution. The solution was diluted with EtOAc, washed once with water and brine, dried over $Na_2SO_4$, filtered, and concentrated in vacuo to afford the crude product (0.093 g) as a yellow oil. The crude material was subjected to purification on a Gilson (RP C18) to give Example 38 (0.035 g, 41% yield).

Electrospray MS $[M+1]^+$ 502.1 for Example 38.

PREPARATION OF EXAMPLE 39

EXAMPLE 39

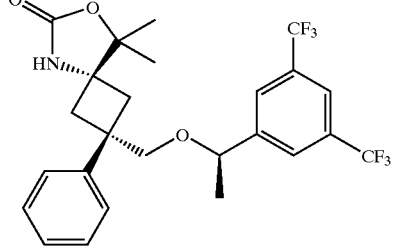

Step 1:

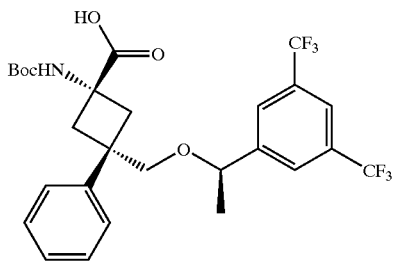

Compound 24

Compound 24 was prepared from Compound 21 by a method analogous to Compound 18 from Compound 17.

Electrospray MS $[M+1]^+$ 562.1 for Compound 24.

Step 2:

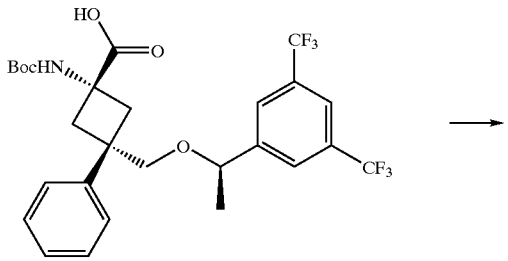

Compound 24

Example 39

Example 39 was prepared from Compound 24 by a method analogous to Example 38 from Compound 18.

Electrospray MS $[M+1]^+$ 502.1 for Example 39.

PREPARATIONS OF EXAMPLE 40

EXAMPLE 40

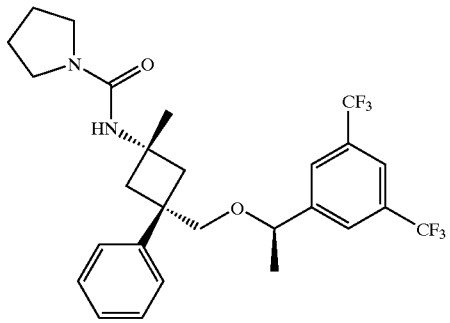

Step 1:

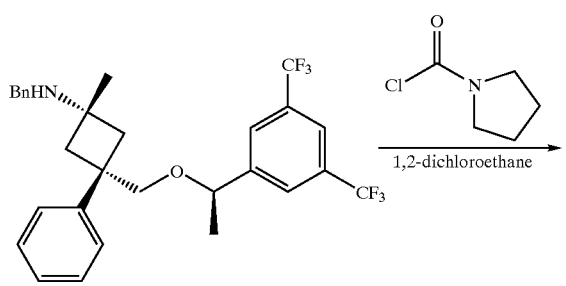

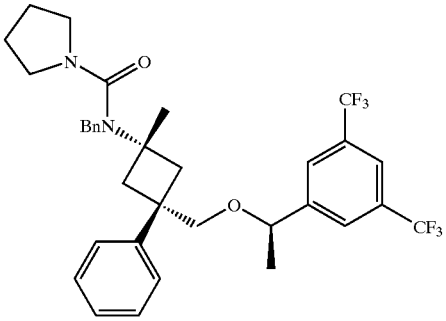

Compound 25

To a solution of Compound 6 (0.14 g, 0.27 mmol, 1.0 equiv) in 1,2-dichloroethane (1 mL) under $N_2$ was added diisopropylethylamine (0.12 mL, 0.68 mmol, 2.5 equiv) followed by 1-pyrrolidinecarbonyl chloride (0.60 mL, 0.54 mmol, 2.0 equiv). After 60 h the reaction was not complete by TLC and was heated to 60° C. for 36 h. The reaction mixture was allowed to cool to room temperature and was quenched with water. The solution was diluted with EtOAc, washed once with brine, dried over $Na_2SO_4$, filtered, and concentrated in vacuo to afford a yellow oil (0.17 g). The crude product was purified by flash chromatography using a biotage eluting with 30% EtOAc/hexane to afford Compound 25 (0.10 g, 59% yield) as a colorless gum.

Electrospray MS [M+1]$^+$ 619.1 for Compound 25.

Step 2:

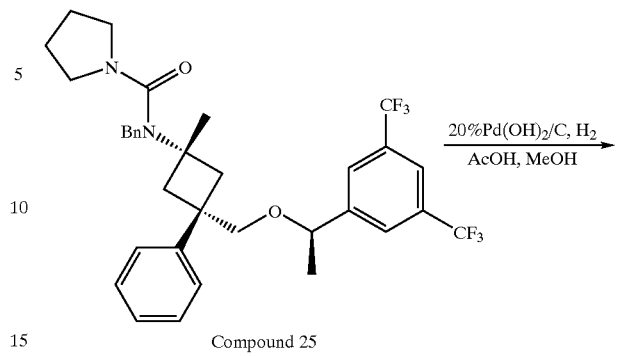

Compound 25

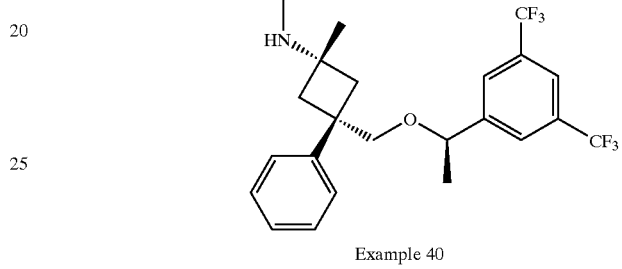

Example 40

To a solution of Compound 25 (0.096 g, 0.16 mmol, 1.0 equiv) in MeOH (4 mL) under $N_2$ was added 20% Pd(OH)$_2$ on carbon (0.2 g) and AcOH (4 mL). The reaction mixture was allowed to stir for 5 h under $H_2$. The suspension was filtered through celite, washed with EtOAc and concentrated in vacuo to afford a colorless oil (0.071 g). The crude product was purified by flash chromatography using a biotage eluting with 40% EtOAc/hexane to afford Example 40 (0.040 g, 47% yield) as a white solid.

Electrospray MS [M+1]$^+$ 529.1 for Example 40.

PREPARATION OF EXAMPLE 41

EXAMPLE 41

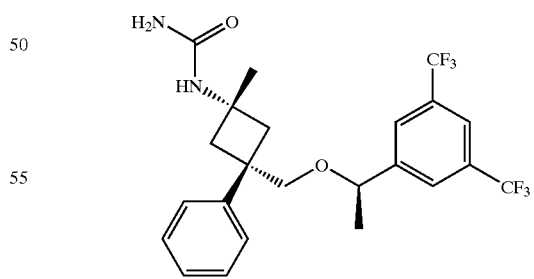

The title compound was prepared from Compound 6 by a method analogous to Example 40 from Compound 6 using trimethylsilyl isocyanate in place of 1-pyrrolidinecarbonyl chloride.

Electrospray MS [M+1]$^+$ 475.1 for Example 41.

PREPARATION OF EXAMPLE 42

EXAMPLE 42

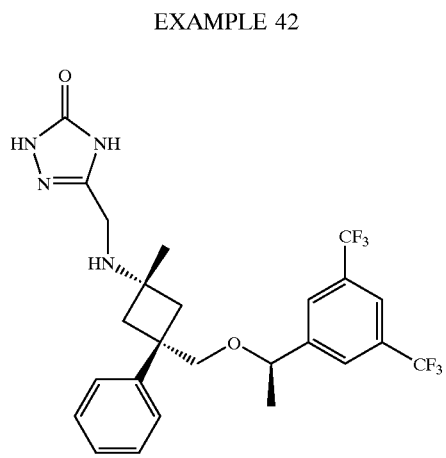

Step 1:

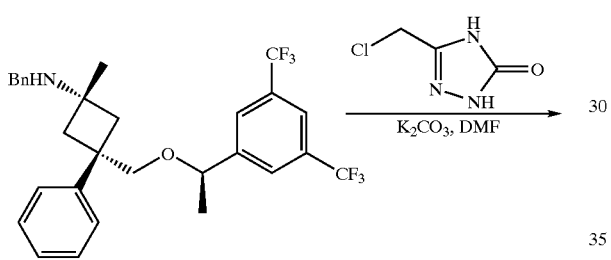

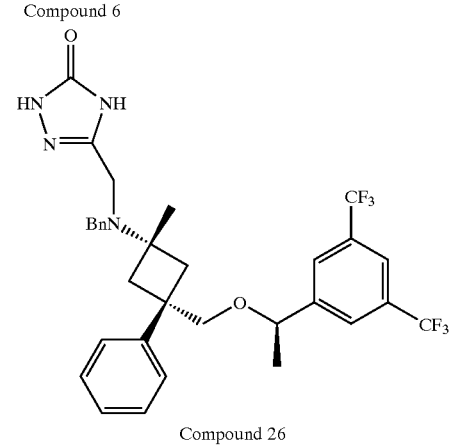

Compound 26

To a solution of Compound 6 (0.083 g, 0.16 mmol, 1.0 equiv) and potassium carbonate (0.029 g, 0.21 mmol, 1.3 equiv) in DMF (1.0 mL) at 0° C. was added chlorotriazolinone (0.026 g, 0.19 mmol, 1.2 equiv). The reaction mixture was allowed to warm to room temperature and stir for 20 h. The suspension was filtered through a plug of glass wool and concentrated in vacuo to afford a colorless oil. The crude material was purified on a Gilson (RP C18) to afford Compound 26 (0.033 g, 33% yield).

Electrospray MS [M+1]$^+$ 619.1 for Compound 26.

Step 2:

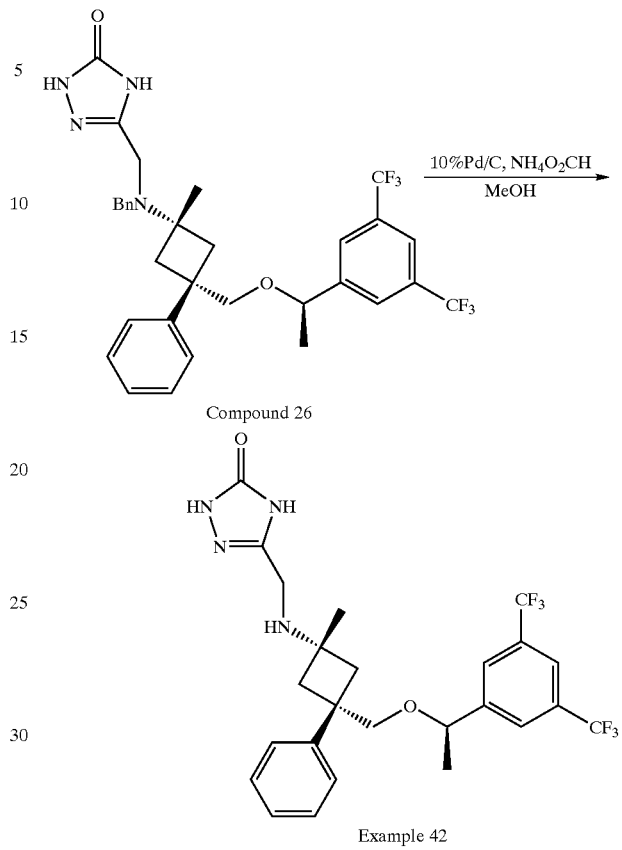

Example 42

Example 42 was prepared from Compound 26 by a method analogous to Example 18 from Compound 6.

Electrospray MS [M+1]$^+$ 529.1 for Example 42.

PREPARATION OF EXAMPLE 43

EXAMPLE 43

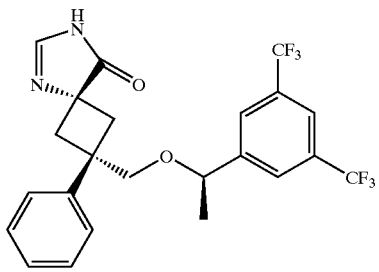

To a solution of Example 34 (0.058 g, 0.13 mmol, 1.0 equiv) in toluene (1.6 mL) under $N_2$ was added triethylorthoformate (0.027 mL, 0.16 mmol, 1.2 equiv) followed by AcOH (0.010 mL). The solution was refluxed for 4.5 h. The reaction mixture was allowed to cool to room temperature and was quenched with water. The solution was diluted with EtOAc, washed once with brine, dried over $Na_2SO_4$, filtered, and concentrated in vacuo to afford a colorless oil (0.058 g). The crude product was purified by flash chromatography using a biotage eluting with 2% MeOH/$CH_2Cl_2$ to afford Example 43 (0.038 g, 62% yield) as a colorless gum.

Electrospray MS [M+1]$^+$ 471.1 for Example 43.

PREPARATION OF EXAMPLE 44

EXAMPLE 44

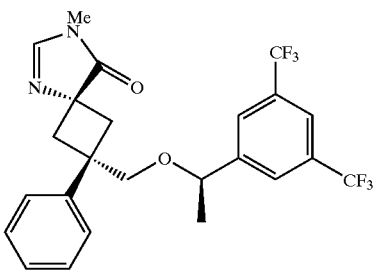

The title compound was prepared from Example 33 by a method analogous to Example 43 from Example 34.
Electrospray MS [M+1]$^+$ 485.1 for Example 44.

PREPARATION OF EXAMPLE 45

EXAMPLE 45

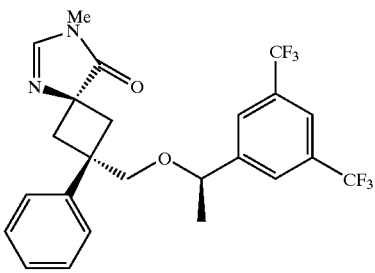

The title compound was prepared from Example 27 by a method analogous to Example 43 from Example 34.
Electrospray MS [M+1]$^+$ 485.1 for Example 45.

PREPARATION OF EXAMPLE 46

EXAMPLE 46

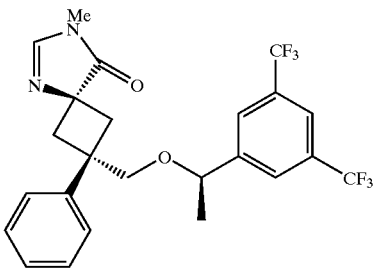

To a solution of Example 28 (1.8 g, 3.9 mmol, 1.0 equiv) in toluene (96 mL) under N$_2$ was added triethylorthoformate (0.77 mL, 4.68 mmol, 1.2 equiv) followed by AcOH (0.3 mL). The solution was refluxed for 3 h. The reaction mixture was allowed to cool to room temperature and was quenched with water. The solution was diluted with EtOAc, washed once with saturated NaHCO$_3$ solution and brine, dried over Na$_2$SO$_4$, filtered, and concentrated in vacuo to afford a colorless oil (1.89 g). The crude product was purified by flash chromatography using a biotage eluting with the solvent gradient 2% MeOH/CH$_2$Cl$_2$ to 5% MeOH/CH$_2$Cl$_2$ to afford Example 46 (1.26 g, 68% yield) as a white foam.

Electrospray MS [M+1]$^+$ 471.1 for Example 46.

PREPARATION OF EXAMPLE 47

EXAMPLE 47

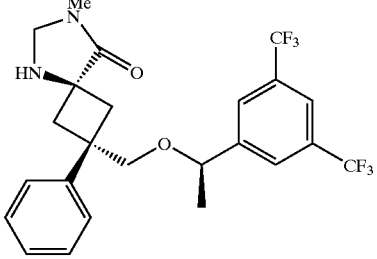

To a solution of Example 45 (0.080 g, 0.17 mmol, 1.0 equiv) in MeOH (1.0 mL) under N$_2$ was added sodium borohydride (0.013 g, 0.34 mmol, 2.0 equiv). After 7 h, the solution was neutralized with AcOH and concentrated in vacuo. The residue was dissolved with EtOAc, washed once with saturated sodium bicarbonate solution, water, and brine, dried over Na$_2$SO$_4$, filtered, and concentrated in vacuo to afford a colorless oil (0.076 g). The crude product was purified by flash chromatography using a biotage eluting with the solvent gradient 60% EtOAc/hexane to 90% EtOAc/hexane to 5% MeOH/EtOAc to afford Example 47 (0.047 g, 59% yield).

Electrospray MS [M+1]$^+$ 487.1 for Example 47.

PREPARATION OF EXAMPLE 48

EXAMPLE 48

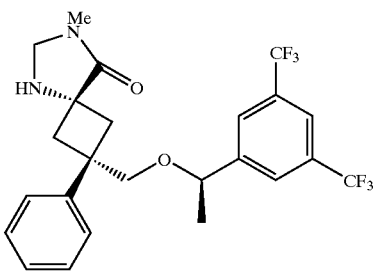

The title compound was prepared from Example 44 by a method analogous to Example 47 from Example 45.

Electrospray MS [M+1]$^+$ 487.1 for Example 48.

PREPARATION OF EXAMPLE 49

EXAMPLE 49

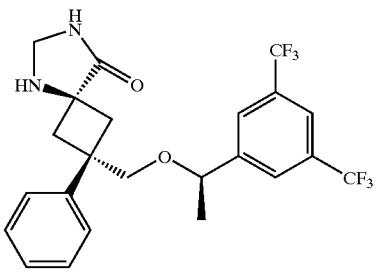

To a solution of Example 46 (1.21 g, 2.57 mmol, 1.0 equiv) in MeOH (15 mL) under $N_2$ at 0° C. was added sodium borohydride (0.19 g, 5.14 mmol, 2.0 equiv). After 2.5 h at 0° C., the solution was neutralized with AcOH (2 mL) and concentrated in vacuo. The residue was dissolved with EtOAc, washed once with saturated sodium bicarbonate solution, water, and brine, dried over $Na_2SO_4$, filtered, and concentrated in vacuo to afford a white solid. The crude product was purified by flash chromatography using a biotage eluting with the solvent gradient 80% EtOAc/hexane to EtOAc to 5% MeOH/EtOAc to afford Example 49 (1.15 g, 95% yield) as a white solid.

Electrospray MS $[M+1]^+$ 473.1 for Example 49.

PREPARATION OF EXAMPLE 50

EXAMPLE 50

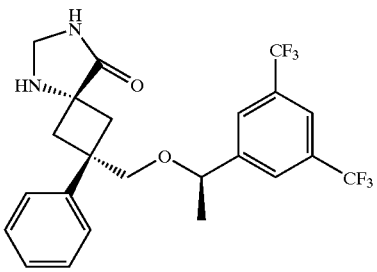

The title compound was prepared from Example 43 by a method analogous to Example 47 from Example 45.

Electrospray MS $[M+1]^+$ 473.1 for Example 50.

PREPARATION OF EXAMPLE 51

EXAMPLE 51

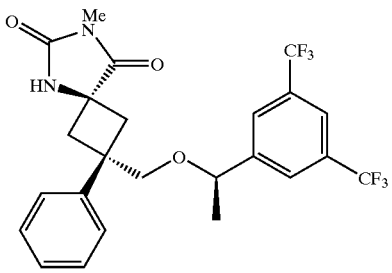

To a solution of Example 27 (0.054 g, 0.114 mmol, 1.0 equiv) in anhydrous $CH_2Cl_2$ (2.5 mL) under $N_2$ was added diisopropylethylamine (0.044 mL, 0.25 mmol, 2.2 equiv) and triphosgene (0.010 g, 0.034 mmol, 0.3 equiv). After 2 h, the reaction mixture was diluted with $CH_2Cl_2$, washed twice with brine, dried over $Na_2SO_4$, filtered, and concentrated in vacuo. The crude product was purified by flash chromatography using a biotage eluting with 75% EtOAc/hexane to afford Example 51 (0.028 g, 49% yield) as a white solid.

Electrospray MS $[M+1]^+$ 501.1 for Example 51.

PREPARATION OF EXAMPLE 52

EXAMPLE 52

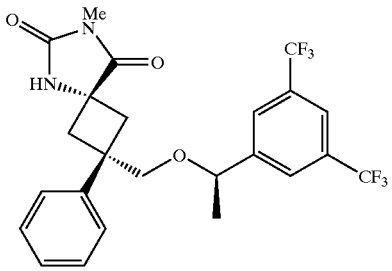

The title compound was prepared from Example 33 by a method analogous to Example 51 from Example 27.

Electrospray MS $[M+1]^+$ 501.1 for Example 52.

PREPARATION OF EXAMPLE 53

EXAMPLE 53

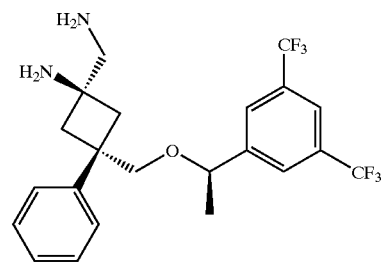

Step 1:

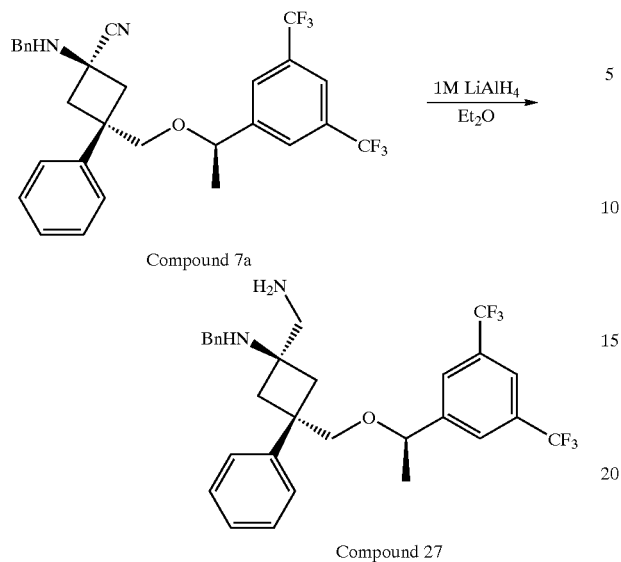

Compound 7a

Compound 27

To a solution of Compound 7a, the less polar diastereomer,(1.4 g, 2.7 mmol, 1.0 equiv) in dry ether (15 ml) at 0° C. was added 1.0 M lithium aluminum hydride in ether (2.7 ml, 2.7 mmol, 1.0 equiv). After 3 h at 0° C., the reaction was quenched with sodium-potassium tartrate solution. The solution was diluted with EtOAc, washed with saturated aqueous $NaHCO_3$ solution, dried over $Na_2SO_4$, filtered and concentrated in vacuo to provide the crude Compound 27 (1.3 g, 90% yield).

Step 2:

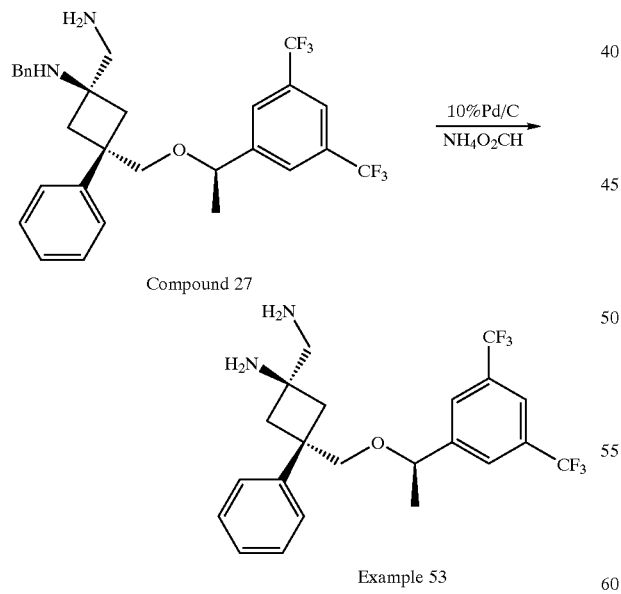

Compound 27

Example 53

Example 53 was prepared from Compound 27 by a method analogous to Example 18 from Compound 6.

Electrospray MS [M+1]$^+$ 447.1 for Example 53.

PREPARATION OF EXAMPLE 54

EXAMPLE 54

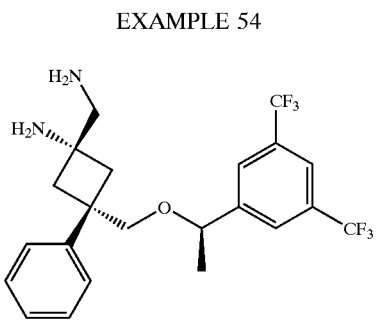

The title compound was prepared from Compound 7b, the more polar diastereomer, by a method analogous to Example 53 from Compound 7a.

Electrospray MS [M+1]$^+$ 447.1 for Example 54.

PREPARATION OF EXAMPLE 55

EXAMPLE 55

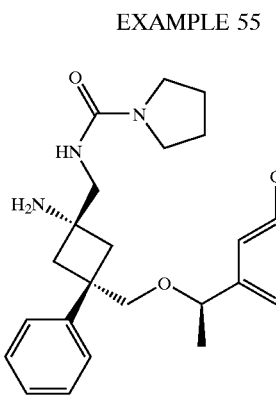

Step 1:

Compound 28

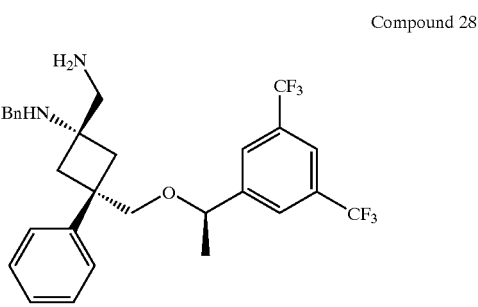

Compound 28 was prepared from Compound 7b by a method analogous to Compound 27 from Compound 7a.

Step 2:

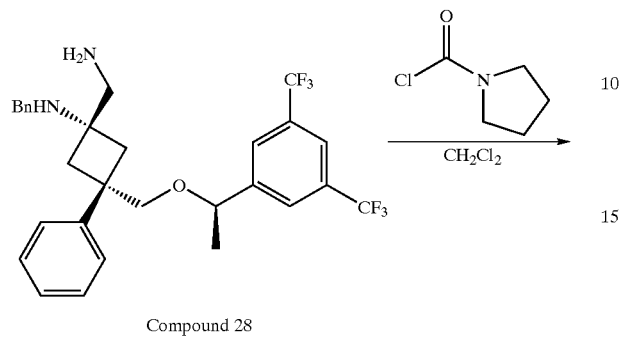

Compound 28

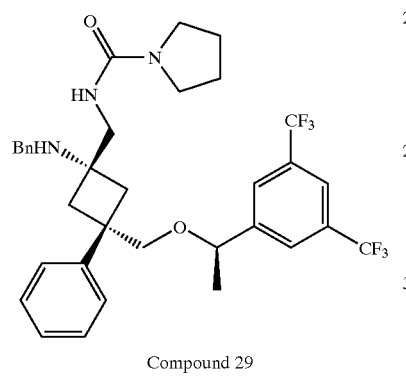

Compound 29

To a solution of Compound 28 (0.105 g, 0.20 mmol, 1.0 equiv) in CH₂Cl₂ (2 mL) at 0° C. under N₂ was added diisopropylethylamine (0.052 mL, 0.30 mmol, 1.5 equiv) followed by 1-pyrrolidinecarbonyl chloride (0.024 mL, 0.22 mmol, 1.1 equiv). The solution was allowed to warm to room temperature overnight. The reaction mixture was quenched with saturated ammonium chloride solution and washed with EtOAc (3×). The combined organic layers were dried over MgSO₄, filtered, and concentrated in vacuo to afford Compound 29 as a white foam. The crude product was carried forward without purification.

Step 3:

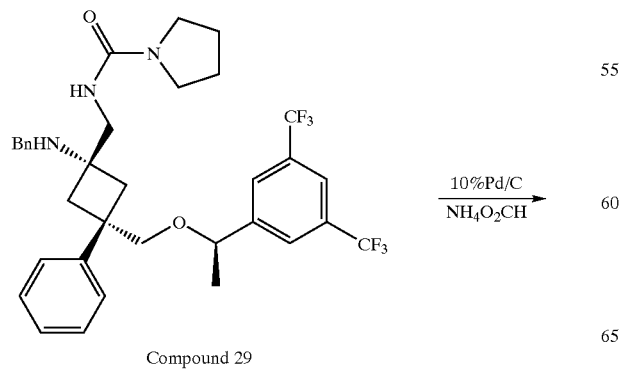

Compound 29

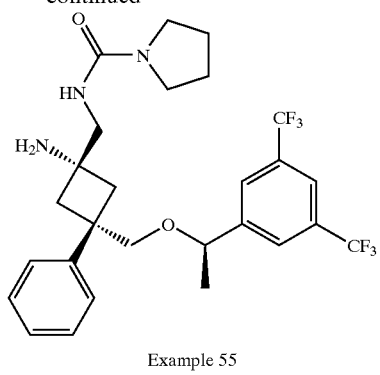

Example 55

Example 55 was prepared from Compound 29 by a method analogous to Example 18 from Compound 6.

Electrospray MS [M+1]⁺ 544.1 for Example 55.

PREPARATION OF EXAMPLE 56

EXAMPLE 56

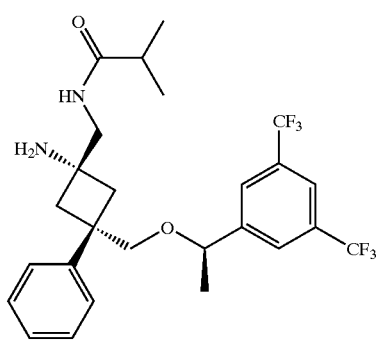

The title compound was prepared from Compound 28 by a method analogous to Example 55 from Compound 28 using isobutyryl chloride in place of 1-pyrrolidinecarbonyl chloride.

Electrospray MS [M+1]⁺ 517.1 for Example 56.

PREPARATION OF EXAMPLE 57

EXAMPLE 57

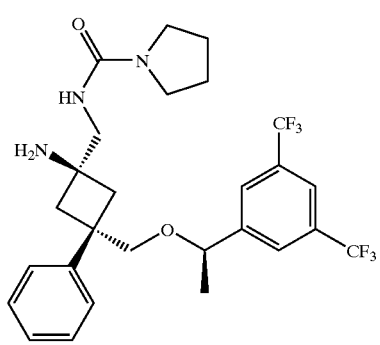

The title compound was prepared from Compound 27 by a method analogous to Example 55 from Compound 28.

Electrospray MS [M+1]⁺ 544.1 for Example 57.

PREPARATION OF EXAMPLE 58

EXAMPLE 58

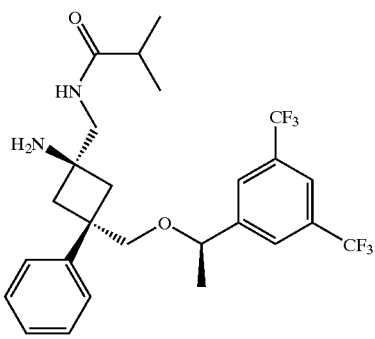

The title compound was prepared from Compound 27 by a method analogous to Example 55 from Compound 28 using isobutyryl chloride in place of 1-pyrrolidinecarbonyl chloride.

Electrospray MS [M+1]⁺ 517.1 for Example 58.

PREPARATION OF EXAMPLE 59

EXAMPLE 59

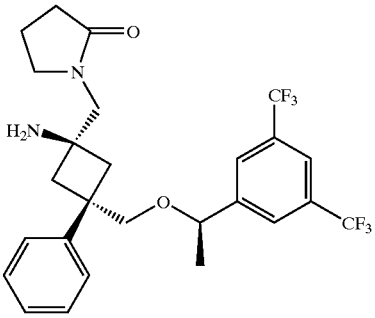

Step 1:

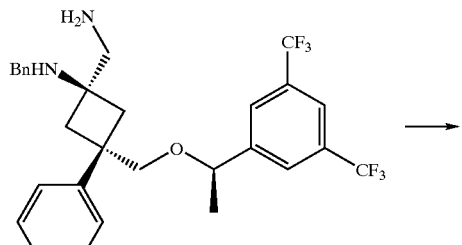

Compound 27

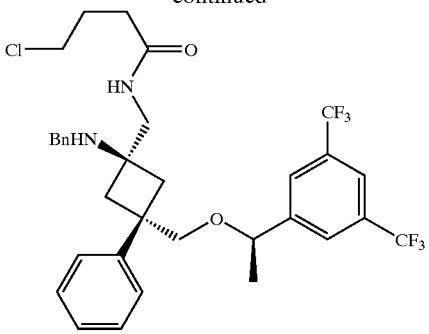

Compound 30

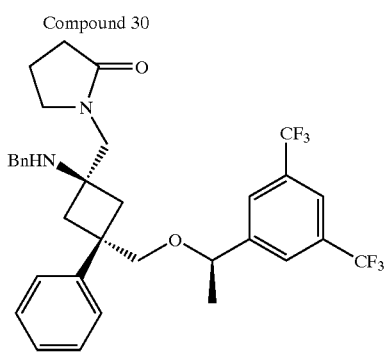

Compound 31

To a solution of Compound 27 (0.133 g, 0.25 mmol, 1.0 equiv) in MeOH (2 mL) at −78° C. under N₂ was added 4-chlorobutyryl chloride (0.031 mL, 0.27 mmol, 1.1 equiv). The solution was allowed to warm to room temperature and stir for 5 h. The reaction mixture was quenched with saturated sodium bicarbonate solution and washed with EtOAc (3×). The combined organic layers were dried over MgSO₄, filtered, and concentrated in vacuo to afford Compound 30 as a colorless oil. To a solution of the oil in anhydrous THF (2 mL) was added sodium hydride (0.011 g, 0.27 mmol, 1.1 equiv) as a 60% dispersion in mineral oil. After 4 h at reflux, the solution was allowed to cool to room temperature. The reaction mixture was quenched with saturated ammonium chloride solution and washed with EtOAc (3×). The combined organic layers were dried over MgSO₄, filtered, and concentrated in vacuo to afford Compound 31.

Step 2:

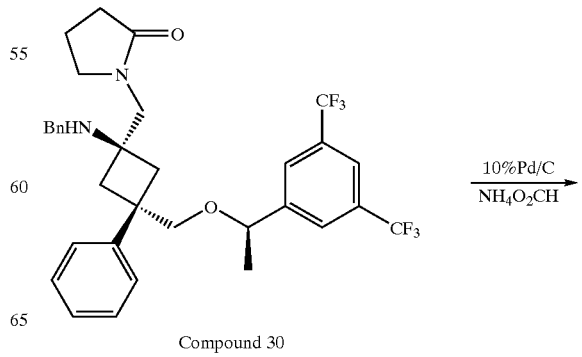

Compound 30

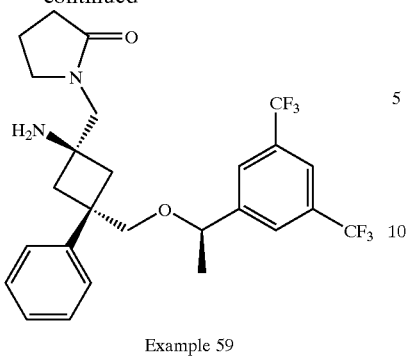

Example 59

Example 59 was prepared from Compound 30 by a method analogous to Example 18 from Compound 6.

Electrospray MS [M+1]⁺ 515.1 for Example 59.

PREPARATION OF EXAMPLE 60

EXAMPLE 60

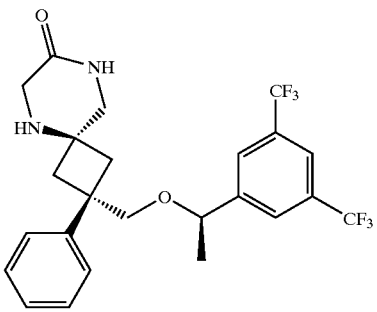

The title compound was prepared from Compound 27 by a method analogous to Example 59 from Compound 27 using 2-chloroacetyl chloride in place of 4-chlorobutyryl chloride.

Electrospray MS [M+1]⁺ 487.1 for Example 60.

PREPARATION OF EXAMPLE 61

EXAMPLE 61

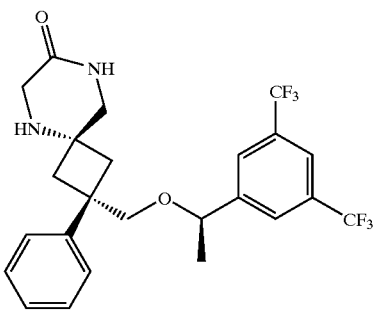

The title compound was prepared from Compound 28 by a method analogous to Example 59 from Compound 27 using 2-chloroacetyl chloride in place of 4-chlorobutyryl chloride.

Electrospray MS [M+1]⁺ 487.1 for Example 61.

PREPARATION OF EXAMPLE 62

EXAMPLE 62

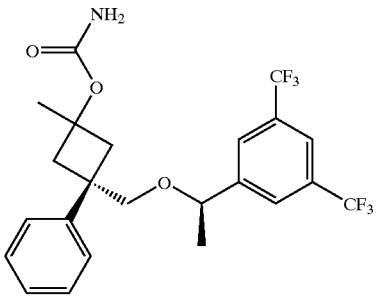

To a solution of a 1:1 diastereomeric mixture of Examples 26a and 26b (0.060 g, 0.14 mmol, 1.0 equiv) in CH₂Cl₂ (1.0 mL) under N₂ was added trichloroacetyl isocyanate (0.020 mL, 0.17 mmol, 1.2 equiv). After 16 h, the solution was concentrated in vacuo. To the residue in MeOH (3 mL) and water (3 mL) was added potassium carbonate (0.058 g, 0.42 mmol, 3 equiv). After 6 h, the reaction mixture was diluted with water and CH₂Cl₂. The combined organic layers were dried over MgSO₄, filtered, and concentrated in vacuo. The crude product was purified by flash chromatography eluting with 30% EtOAc/hexane to afford Example 62 (0.054 g, 81% yield) as a 1:1 mixture of diastereomers.

Electrospray MS [M+1]⁺ 476.1 for Example 62.

PREPARATION OF EXAMPLES 63a AND 63b

EXAMPLE 63a

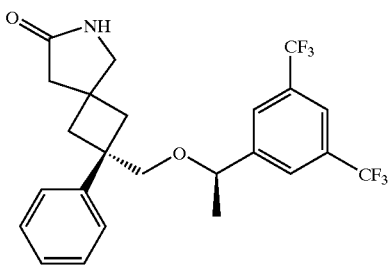

Minor Diastereomer

EXAMPLE 63b

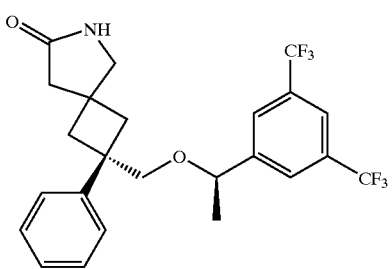

Major Diastereomer

Step 1:

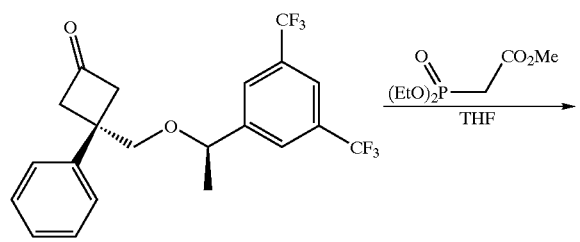

Example 2

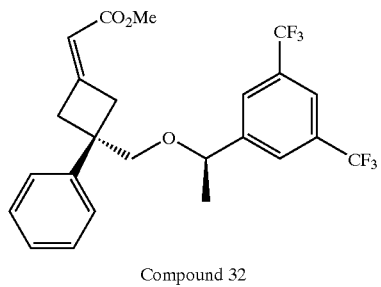

Compound 32

To a suspension of sodium hydride (0.12 g, 3.0 mmol, 1.5 equiv) as a 60% dispersion in mineral oil in anhydrous THF (8 mL) at 0° C. was added methyl diethylphosphonoacetate (0.62 mL, 3.4 mmol, 1.7 equiv) dropwise. After 10 minutes, the ice bath was removed and Example 2 (0.82 g, 2.0 mmol, 1.0 equiv) was added in THF (8 mL) via cannula over a period of 5 minutes. After 4 h, the solution was cooled to 0° C., quenched with saturated NH$_4$Cl solution, and diluted with EtOAc. The organic layer was washed once with brine, dried over Na$_2$SO$_4$, filtered, and concentrated in vacuo to afford a yellow oil. The crude material was purified by flash chromatography using a biotage eluting with 5% EtOAc/hexane to afford Compound 32 (0.53 g, 55% yield).

Electrospray MS [M+1]$^+$ 473.1 for Compound 32.

Step 2:

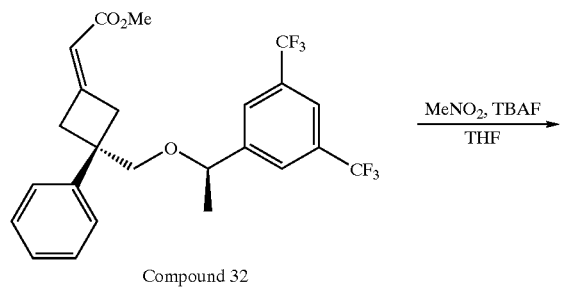

Compound 32

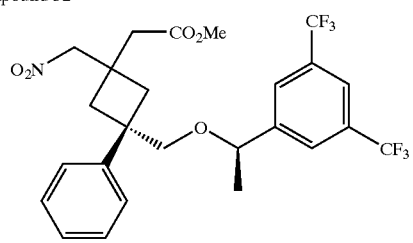

Compound 33

To a solution of Compound 32 (0.063 g, 0.13 mmol, 1.0 equiv) in anhydrous THF (5 mL) was added nitromethane (0.015 mL, 0.27 mmol, 2.0 equiv) followed by a 1M solution of tetrabutylammonium fluoride in THF (0.20 mL, 0.20 mmol, 1.5 equiv). After 20 h at reflux, the solution was allowed to cool to room temperature and diluted with 10% citric acid solution. The aqueous layer was extracted with EtOAc (3×). The combined organic layers were dried over MgSO$_4$, filtered, and concentrated in vacuo. The crude material was purified by flash chromatography eluting with 20% Et$_2$O/hexane to afford Compound 33 as a colorless oil.

Step 3:

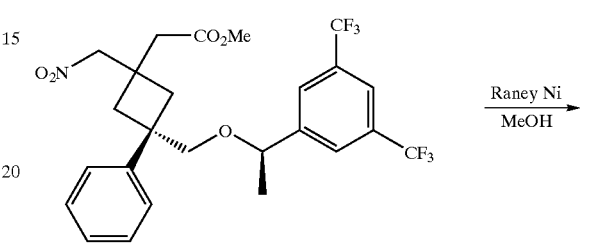

Compound 33

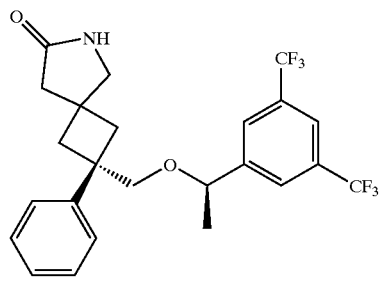

Compound 63a

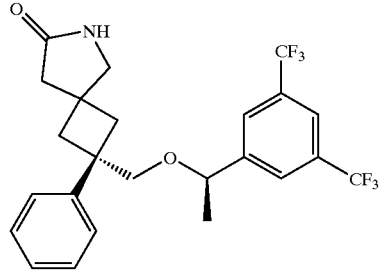

Compound 63b

To a solution of Compound 33 in MeOH (5 mL) was added Raney Ni. After 5 h at 50 psi of H$_2$, the suspension was filtered through celite washing with MeOH. The crude material was purified by flash chromatography eluting with 80% EtOAc/hexane to afford a 1:4 mixture of diastereomers, Examples 63a and 63b, as a colorless oil. The mixture was separated by HPLC on a Chiralcel OD column using 9/1 hexane/IPA. Example 63a, the first eluted isomer, was obtained as a white foam and Example 63b, the second eluted product, was obtained as a white foam.

Electrospray MS [M+1]$^+$ 472.1 for Example 63a.

Electrospray MS [M+1]$^+$ 472.1 for Example 63b.

PREPARATION OF EXAMPLE 64

EXAMPLE 64

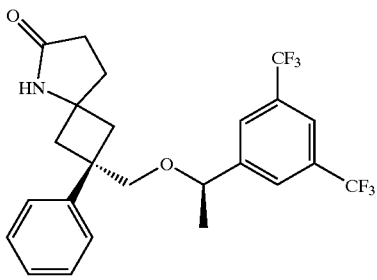

Step 1:

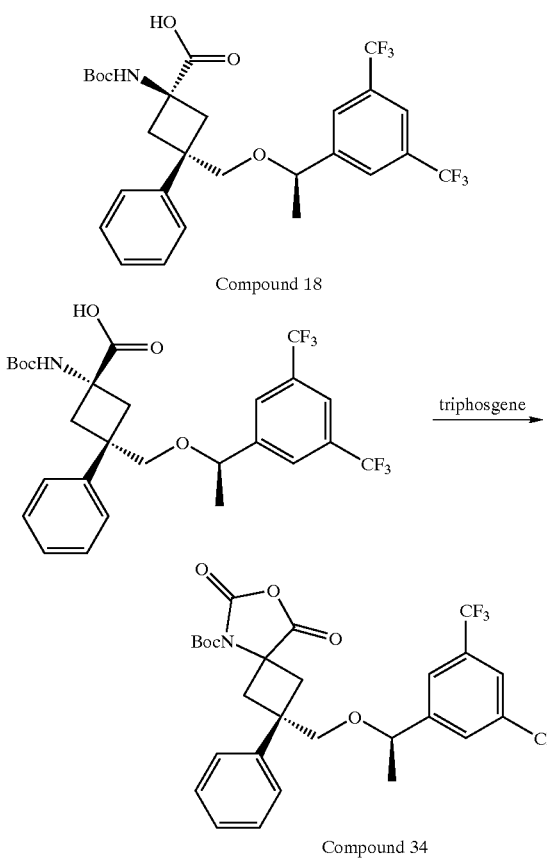

To a solution of a 1:1 diastereomeric mixture of Compound 18 and Compound 24 (3.48 g, 6.2 mmol, 1.0 equiv) in anhydrous $CH_2Cl_2$ (50 mL) under $N_2$ was added diisopropylethylamine (0.32 mL, 18.5 mmol, 3.0 equiv) and a solution of triphosgene (0.92 g, 3.1 mmol, 0.5 equiv) in anhydrous $CH_2Cl_2$ (10 mL). After 16 h, the reaction mixture was filtered through a plug of silica gel washing with $CH_2Cl_2$. The solution was concentrated in vacuo to afford the crude product as a yellow oil (3.5 g, 100% yield).

Step 2:

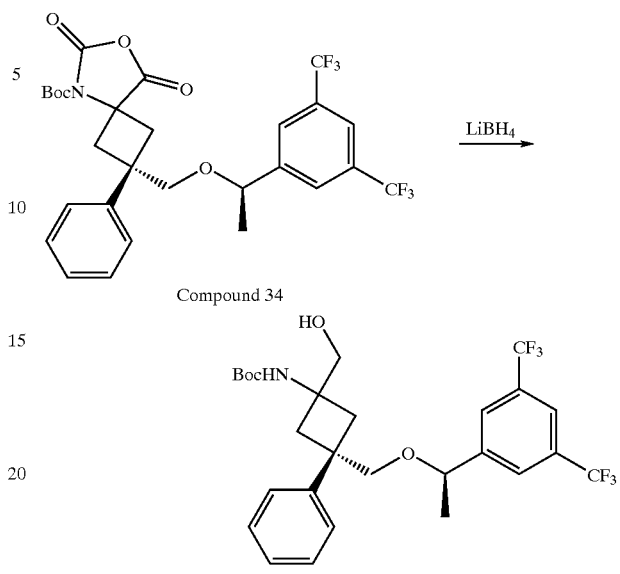

To a solution of Compound 34 (3.5 g, 6.2 mmol, 1.0 equiv) in anhydrous THF (50 mL) was added lithium borohydride (0.268 g, 12.3 mmol, 2.0 equiv) in small portions. After 16 h, the reaction mixture was quenched with saturated $NaHCO_3$ solution and diluted with EtOAc. The layers were separated and the aqueous layer was extracted with EtOAc (2×). The combined organic layers were dried over $MgSO_4$, filtered, and concentrated in vacuo. The crude material was purified by flash chromatography eluting with 25% EtOAc/hexane to afford Compound 35 (1.5 g, 44% yield) as a colorless oil.

Electrospray MS $[M+1]^+$ 548.1 for Compound 35.

Step 3:

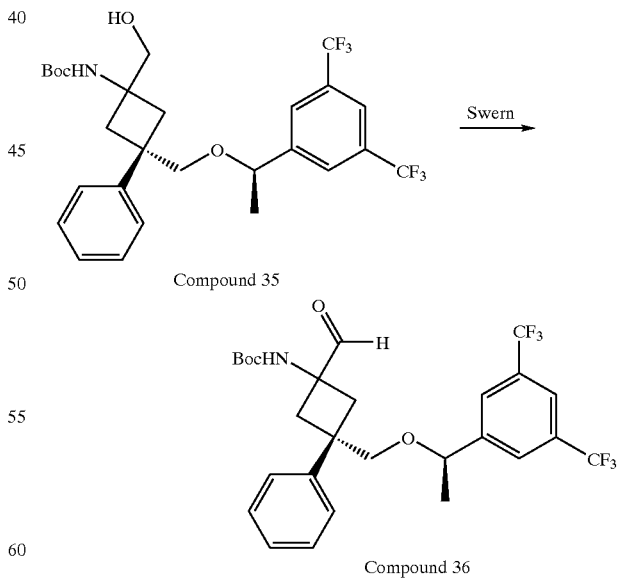

To a solution of DMSO (1.6 mL, 22 mmol, 8.0 equiv) in $CH_2Cl_2$ (50 mL) at −78° C. under $N_2$ was added oxalyl chloride (0.96 mL, 11 mmol, 4.0 equiv) dropwise. After 15 minutes, Compound 35 (1.5 g, 2.7 mmol, 1.0 equiv) in $CH_2Cl_2$ (10 mL) was added to the solution. After 6 h at −78°

C., triethylamine (5.3 mL, 38 mmol, 14.0 equiv) was added and the reaction mixture was allowed to warm to room temperature. The reaction was quenched with saturated NaHCO$_3$ solution and diluted with CH$_2$Cl$_2$. The layers were separated and the aqueous layer was extracted with CH$_2$Cl$_2$ (2×). The combined organic layers were dried over MgSO$_4$, filtered through a plug of silica gel, and concentrated in vacuo to afford Compound 36 as a yellow oil (1.47 g, 100% yield).

Step 4:

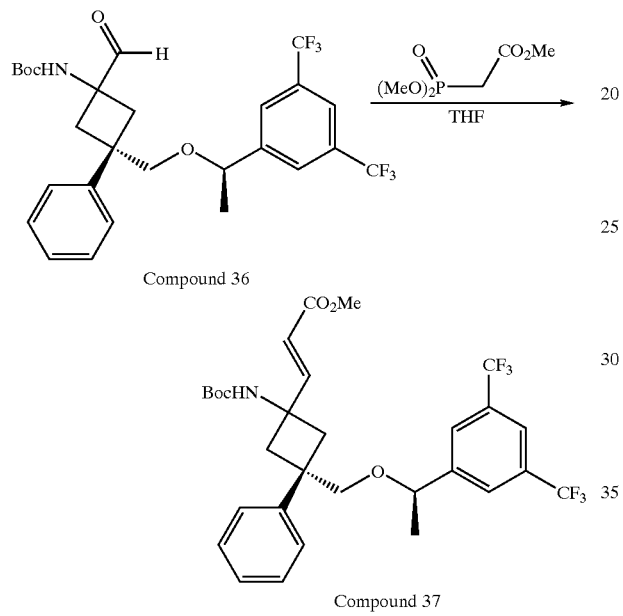

Compound 36

Compound 37

To a suspension of sodium hydride (0.342 g, 8.1 mmol, 3.0 equiv) as a 60% dispersion in mineral oil in anhydrous THF (50 mL) at 0° C. was added methyl dimethylphosphonoacetate (1.7 g, 8.1 mmol, 3.0 equiv) dropwise. After 15 minutes, a solution of Compound 36 (1.47 g, 2.7 mmol, 1.0 equiv) in THF (10 mL) was added dropwise. After the addition was complete, the ice bath was removed and the solution was allowed to warm to room temperature. After 1 h, the reaction was quenched with saturated NH$_4$Cl solution, and diluted with EtOAc. The layers were separated and the aqueous layer was extracted with EtOAc (2×). The combined organic layers were dried over MgSO$_4$, filtered through a pad of silica gel, and concentrated in vacuo. The crude material was purified by flash chromatography on a biotage eluting with 20% EtOAc/hexane to afford Compound 37 (1.0 g, 62% yield) as a colorless oil.

Electrospray MS [M+1]$^+$ 602.1 for Compound 37.

Step 5:

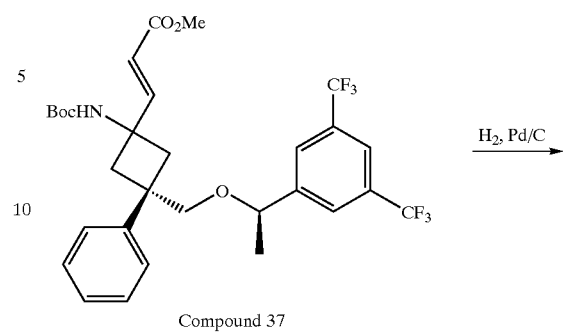

Compound 37

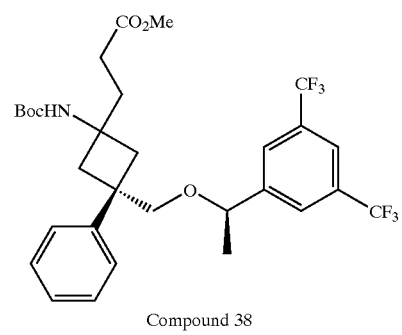

Compound 38

To a solution of Compound 37 (1.0 g, 1.7 mmol, 1.0 equiv) in EtOH (20 mL) under N$_2$ was added 10% Pd on carbon (0.177 g, 0.17 mmol, 0.1 equiv). The reaction mixture was placed under H$_2$ atmosphere with a balloon. After 2 days, the reaction mixture was filtered through celite and concentrated in vacuo to afford crude Compound 38 (1.0 g, 100% yield).

Step 6:

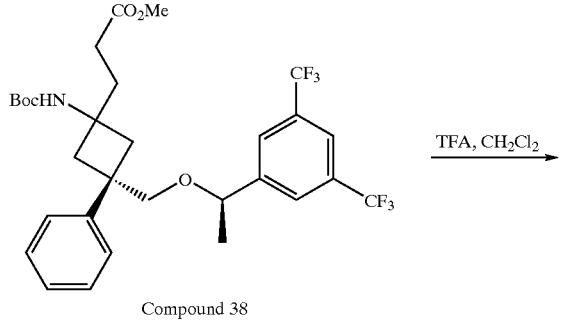

Compound 38

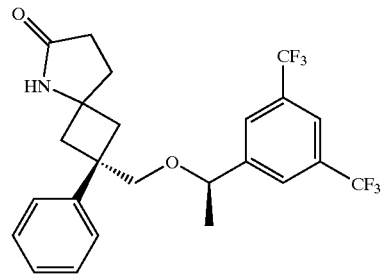

Example 64

Example 64 was prepared from Compound 38 by a method analogous to Example 27 from Compound 19.

Electrospray MS [M+1]+ 472.1 for Example 64.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound having the formula (I):

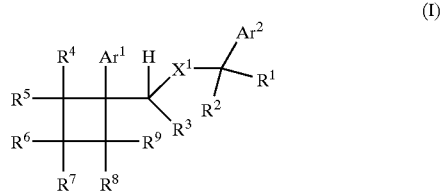

(I)

or the pharmaceutically acceptable salts or solvates thereof, wherein:

$Ar^1$ and $Ar^2$ are each independently:

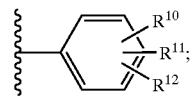

$X^1$ is selected from the group consisting of —O—, —S—, —SO—, —SO$_2$—, —NR$^{20}$—, —N(COR$^{20}$)— and —N(SO$_2$R$^{17}$)—; and when $X^1$ is selected from the group consisting of —SO—, —SO$_2$—, —N(COR$^{20}$)— and —N(SO$_2$R$^{17}$)—, then $R^1$ and $R^2$ are each independently selected from the group consisting of H, $C_1$–$C_6$ alkyl, hydroxy($C_1$–$C_3$ alkyl)-, $C_3$–$C_8$ cycloalkyl, —CH$_2$F, —CHF$_2$ and —CF$_3$; or $R^1$ and $R^2$, together with the carbon atom to which they are both attached, form a $C_3$–$C_8$ cycloalkyl ring; and when $X^1$ is selected from the group consisting of —O—, —S— and —NR$^{20}$—, then $R^1$ and $R^2$ are each independently selected from the group consisting of H, $C_1$–$C_8$ alkyl, hydroxy($C_1$–$C_3$ alkyl)-, $C_3$–$C_8$ cycloalkyl, —CH$_2$F, —CHF$_2$ and —CF$_3$; or $R^1$ and $R^2$, together with the carbon atom to which they are both attached, form a $C_3$–$C_6$ cycloalkyl group; or $R^1$ and $R^2$, together with the carbon atom to which they are both attached, form a —C(=O) group;

$R^3$ is selected from the group consisting of H, $C_1$–$C_6$ alkyl, hydroxy($C_1$–$C_3$ alkyl)-, $C_3$–$C_8$ cycloalkyl, —CH$_2$F, —CHF$_2$ and —CF$_3$;

$R^4$ and $R^5$ are each independently selected from the group consisting of H, $C_1$–$C_6$ alkyl-, -halogen, —OR$^{20}$, —O—C(O)NR$^{15}$R$^{16}$, —NR$^{15}$R$^{16}$, —NR$^{15}$SO$_2$R$^{17}$, —NR$^{15}$C(O)R$^{14}$, —NR$^{20}$C(O)NR$^{15}$R$^{16}$ and —SR$^{20}$; or $R^4$ and $R^5$, together with the carbon atom to which they are both attached, form a —C(=O)— or —C(=NR$^{13}$)— group;

$R^6$ and $R^7$, taken together with the carbon atom to which they are bound, form:
(a) a 5-membered heterocycloalkyl ring; or
(b) a 5-membered heterocycloalkenyl ring;

wherein said 5-membered heterocycloalkyl ring or said 5-membered heterocycloalkenyl ring each comprise 3 carbon atoms and 2 heteroatoms independently selected from the group consisting of: N=, and —NR$^{20}$— (wherein R$^{20}$ is defined below), and said 5-membered heterocycloalkyl ring or said 5-membered heterocycloalkenyl ring are each optionally substituted with from 1 to 4 R$^{45}$ substituents wherein each R$^{45}$ substituent is independently selected;

$R^8$ and $R^9$ are each independently selected from the group consisting of H, $C_1$–$C_6$ alkyl-, halogen, —OR$^{20}$, —O—C(O)NR$^{15}$R$^{16}$, —NR$^{15}$R$^{16}$, —NR$^{15}$SO$_2$R$^{17}$, —NR$^{15}$C(O)R$^{14}$, —NR$^{20}$C(O)NR$^{15}$R$^{16}$ and —SR$^{20}$; or $R^8$ and $R^9$, taken together with the carbon atom to which they are both attached, form a —C(=O)— group;

$R^{10}$, $R^{11}$ and $R^{12}$ are each independently selected from the group consisting of H, $C_1$–$C_6$ alkyl, $C_3$–$C_8$ cycloalkyl, —OR$^{20}$, halogen, —CN, —NO$_2$, —CF$_3$, —CHF$_2$, —CH$_2$F, —CH$_2$CF$_3$, —OCF$_3$, —OCHF$_2$, —OCH$_2$F, —OCH$_2$CF$_3$, —C(O)OR$^{20}$, —C(O)NR$^{23}$R$^{24}$, —NR$^{23}$C(O)R$^{20}$, —NR$^{23}$CO$_2$R$^{17}$, —NR$^{23}$C(O)NR$^{23}$R$^{24}$, —NR$^{23}$SO$_2$R$^{17}$, —NR$^{23}$R$^{24}$, —SO$_2$NR$^{23}$R$^{24}$, —S(O)$_{n5}$R$^{17}$, aryl, and aryl substituted with (R$^{21}$)$_r$ wherein each R$^{21}$ substitutent is independently selected;

each $R^{13}$ is independently selected from the group consisting of —OH and —O—($C_1$–$C_6$ alkyl);

each $R^{14}$ is independently selected from the group consisting of H, $C_1$–$C_6$ alkyl, $C_3$–$C_8$ cycloalkyl, —$C_1$–$C_6$ alkylNH$_2$ and —$C_1$–$C_6$ alkylNHC(O)O$C_1$–$C_6$ alkyl;

$R^{15}$ and $R^{16}$ are each independently selected from the group consisting of H, benzyl, $C_1$–$C_6$ alkyl, and $C_3$–$C_8$ cycloalkyl;

each $R^{17}$ is independently selected from the group consisting of $C_1$–$C_5$ alkyl, $C_3$–$C_8$ cycloalkyl and —CF$_3$;

each $R^{20}$ is independently selected from the group consisting of H, $C_1$–$C_6$ alkyl, $C_3$–$C_8$ cycloalkyl, —($C_1$–$C_6$) alkylNH$_2$, ($C_1$–$C_6$)alkoxy($C_2$–$C_6$)alkyl, and hydroxy ($C_2$–$C_6$)alkyl;

each $R^{21}$ is a substituent on the aryl ring to which it is attached and is independently selected from the group consisting of $C_1$–$C_6$ alkyl, $C_3$–$C_8$ cycloalkyl, —OH, -halogen, —CN, —NO$_2$, —CF$_3$, —CHF$_2$, —CH$_2$F, —OCF$_3$, —OCHF$_2$, —OCH$_2$F, —O—($C_1$–$C_6$ alkyl), —O—($C_3$–$C_8$ cycloalkyl), —C(O)OR$^{20}$, —C(O) NR$^{23}$R$^{24}$, —NR$^{23}$R$^{24}$, —NR$^{23}$C(O)R$^{20}$, —NR$^{23}$CO$_2$R$^{20}$, —NR$^{23}$C(O)NR$^{23}$R$^{24}$, —NR$^{23}$SO$_2$R$^{17}$ and —S(O)$_{n5}$R$^{17}$;

$R^{23}$ and $R^{24}$ are each independently selected from the group consisting of H, $C_1$–$C_6$ alkyl, $C_3$–$C_8$ cycloalkyl and benzyl;

$R^{30}$ and $R^{31}$ are each independently selected from the group consisting of H, $C_1$–$C_6$ alkyl (e.g., $C_1$–$C_2$ alkyl), —CH$_2$F, —CHF$_2$, —CF$_3$, —OH, and —O($C_1$ to $C_3$)alkyl; or $R^{30}$ and $R^{31}$, together with the carbon atom to which they are both attached, form a —C(=O)— group;

each $R^{45}$ is independently selected from the group consisting of: $C_1$–$C_6$ alkyl (e.g., $C_1$–$O_2$ alkyl), —CH$_2$F, —CHF$_2$, —CF$_3$, —OH, and —O($C_1$ to $C_3$)alkyl; or two R$^{45}$ substituents, together with the carbon atom to which they are both attached, form a —C(=O)— group;

r is from 1 to 3;

$n_4$ is from 0 to 3;

$n_5$ is from 0 to 2; and $n_8$ is from 0 to 4.

2. The compound of claim 1 wherein:
(a) $X^1$ is —O— or —$NR^{20}$—;
(b) $Ar^1$ and $Ar^2$ are each independently represented by the formula:

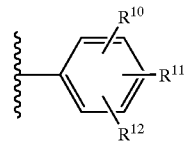

wherein $R^{10}$, $R^{11}$ and $R^{12}$ are each independently selected from the group consisting of H, F, Cl, $C_1$–$C_6$ alkyl, —$CF_3$, —$CHF_2$, —$CH_2F$, —$OR^{20}$, —$OCF_3$, and —$OCHF_2$;

(c) $R^1$ and $R^2$ are each independently selected from the group consisting of H, $C_1$–$C_6$ alkyl and hydroxy ($C_1$–$C_3$alkyl)-; or $R^1$ and $R^2$, together with the carbon atom to which they are both attached, form a —C(=O)— group;

(d) $R^3$ is selected from the group consisting of H and $C_1$–$C_6$ alkyl;

(e) $R^4$ and $R^5$ are each independently selected from the group consisting of H, —OH, $C_1$–$C_6$ alkyl and halogen; or $R^4$ and $R^5$, together with the carbon atom to which they are both attached, form a —C(=O)— group; and (f) $R^8$ and $R^9$ are each independently selected from the group consisting of H, —OH, $C_1$–$C_6$ alkyl and halogen; or $R^8$ and $R^9$, together with the carbon atom to which they are both attached, form a —C(=O)— group.

3. The compound of claim 2 wherein $R^6$ and $R^7$, taken together with the carbon atom to which they are bound, form:
(a) a 5-membered heterocycloalkyl ring; or
(b) a 5-membered heterocycloalkenyl ring;
wherein said 5-membered heterocycloalkyl ring or said 5-membered heterocycloalkenyl ring each comprises 3 carbon atom and 2 heteroatoms independently selected from the group consisting of: N=, and —$NR^{20}$—, and said 5-membered heterocycloalkyl ring or said 5-membered heterocycloalkenyl ring are each optionally substituted with from 1 to 4 $R^{45}$ substituents wherein each $R^{45}$ substituent is independently selected.

4. The compound of claim 3, where the 5-membered heterocycloalkyl ring or the 5-membered heterocycloalkenyl ring is selected from the group consisting of:

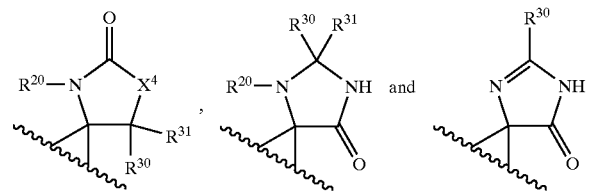

wherein $X^4$ is —$NR^{20}$—.

5. The compound of claim 3, where the 5-membered heterocycloalkyl ring or 5-membered heterocycloalkenyl ring is selected from the group consisting of:

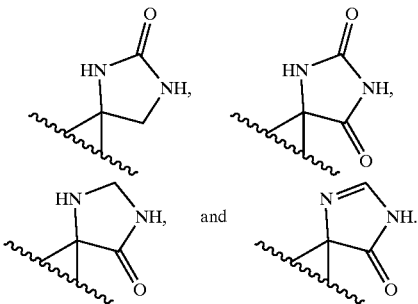

6. The compound of claim 1 wherein said compound has the formula (Ia):

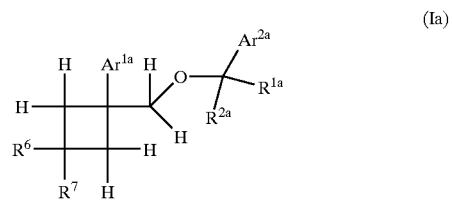

(Ia)

wherein
(A) $Ar^{1a}$ is:

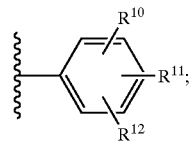

wherein $R^{10}$, $R^{11}$ and $R^{12}$ are each independently selected from the group consisting of H, halogen, —OH, —O($C_1$–$C_6$)alkyl, $C_1$–$C_6$alkyl and —$CF_3$;

(B) $Ar^{2a}$ is:

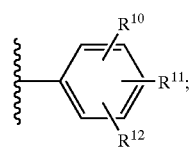

wherein $R^{10}$, $R^{11}$ and $R^{12}$ are independently selected from the group consisting of: H, $C_1$–$C_6$ alkyl, $C_3$–$C_8$ cycloalkyl, —$OR^{20}$ (wherein $R^{20}$ is as defined in claim 1), halogen, —CN, —$NO_2$, —$CF_3$, —$CHF_2$, —$CH_2F$, —$OCH_2CF_3$, —$OCF_3$, —$OCHF_2$, —$OCH_2F$, and —$OCH_2CF_3$;

(C) $R^{1a}$ and $R^{2a}$ are each independently selected from the group consisting of H, $C_1$–$C_6$ alkyl and hydroxy ($C_1$–$C_3$alkyl)-; and (D) $R^6$ and $R^7$ are as defined in claim 1.

7. The compound of claim 6 wherein $R^6$ and $R^7$, taken together with the carbon atom to which they are bound, form:
(a) a 5-membered heterocycloalkyl ring; or
(b) a 5-membered heterocycloalkenyl ring;
wherein said 5-membered heterocycloalkyl ring or said 5-membered heterocycloalkenyl ring each comprises 3 carbon atoms and heteroatoms independently selected from the group consisting of: N═, and —NR²⁰—, and said 5-membered heterocycloalkyl ring and said 5-membered heterocycloalkenyl ring are each optionally substituted with from 1 to 4 R⁴⁵ substituents wherein each R⁴⁵ substituent is independently selected.

8. The compound of claim 7, where the 5-membered heterocycloalkyl ring or 5-membered heterocycloalkenyl ring is selected from the group consisting of:

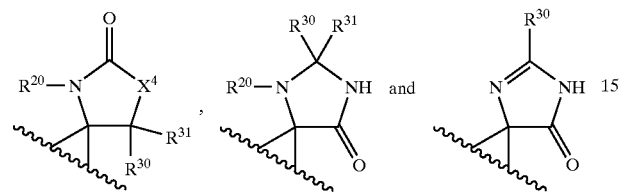

wherein X⁴ is —NR²⁰—.

9. The compound of claim 7, where the 5-membered heterocycloalkyl ring or 5-membered heterocycloalkenyl ring is selected from the group consisting of:

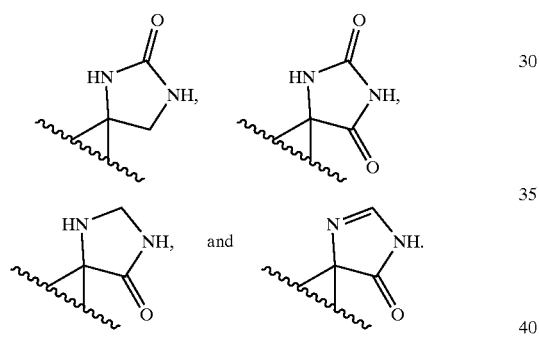

10. The compound of claim 1 selected from the group consisting of:

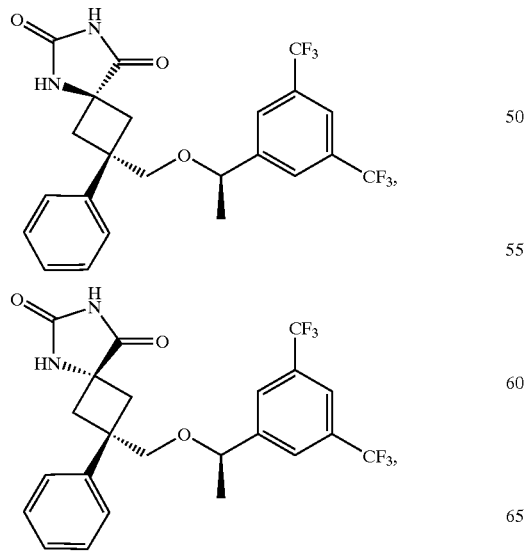

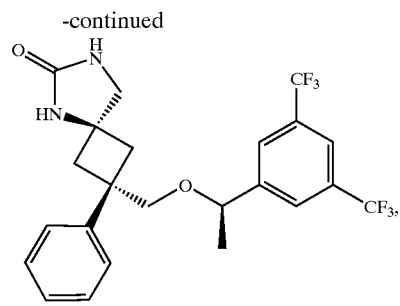

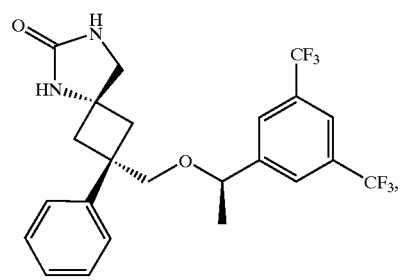

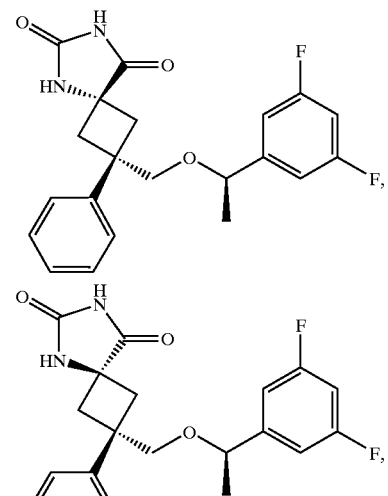

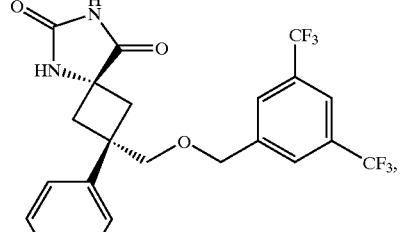

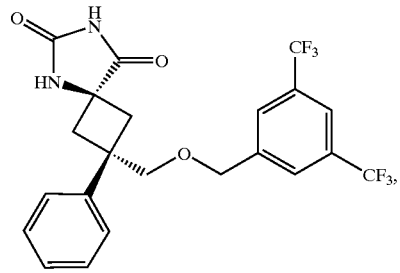

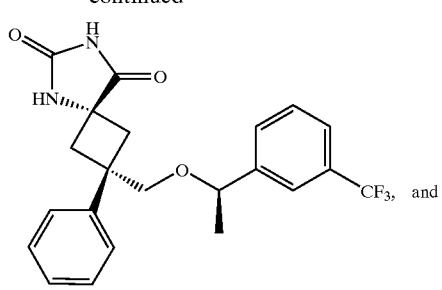, and
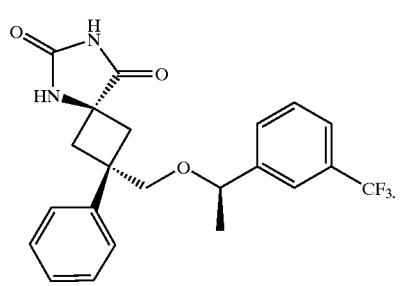
11. The compound of claim 1 selected from the group consisting of:
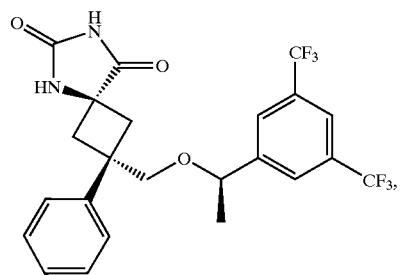
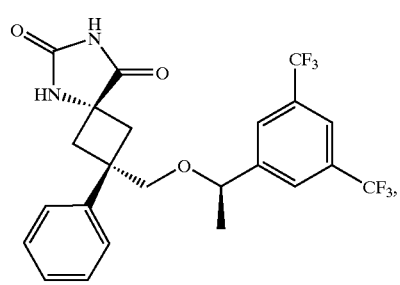
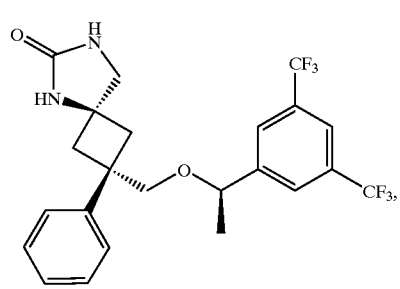
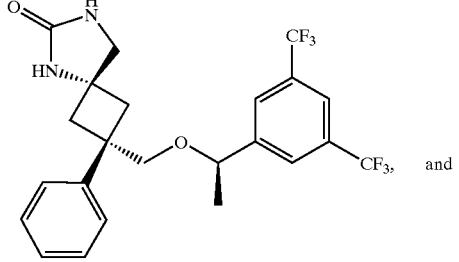, and
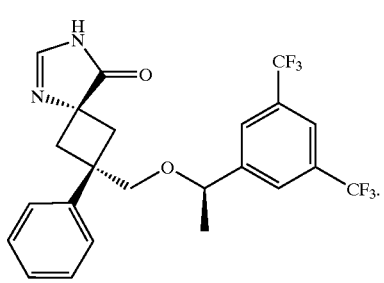
12. The compound of claim 1 selected from the group consisting of:
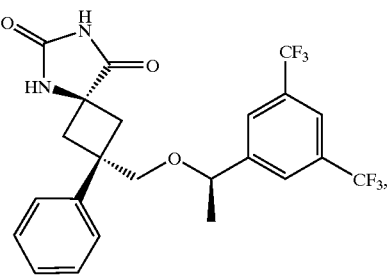
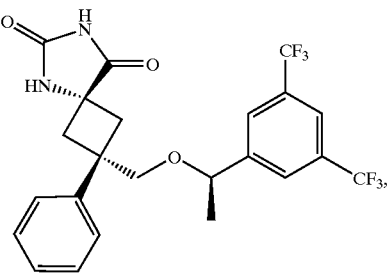
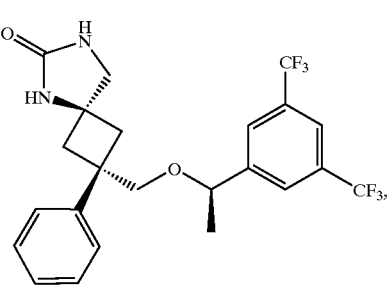

-continued
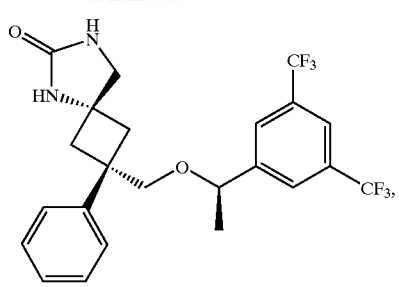
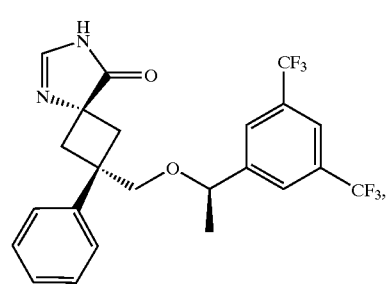
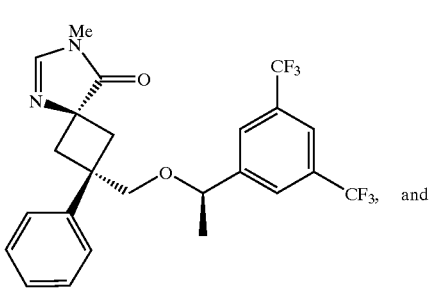 and
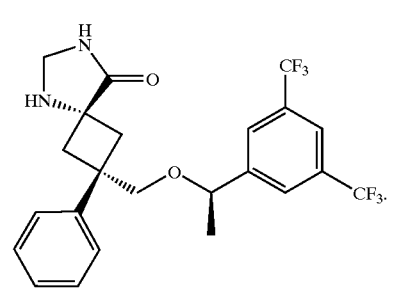
13. The compound of claim 1 selected from the group consisting of:
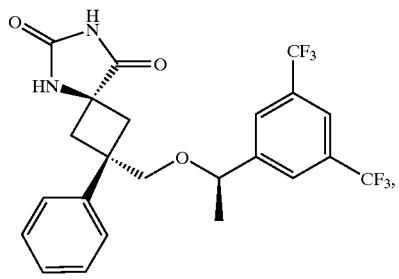
-continued
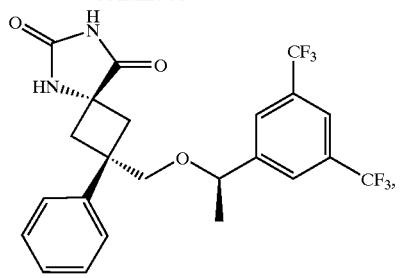
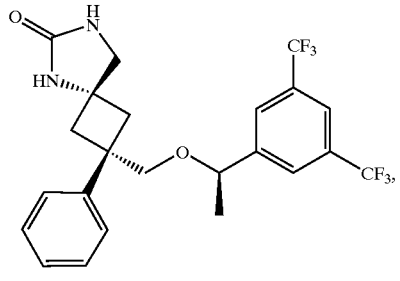
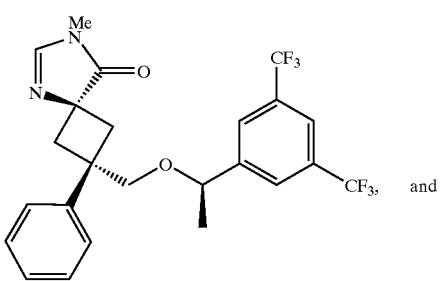 and
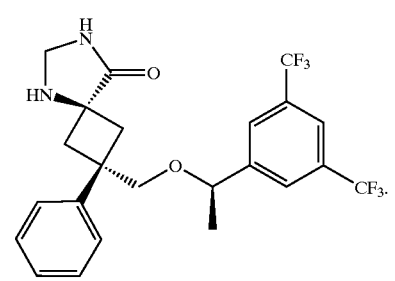
14. The compound of claim 1 having the formula
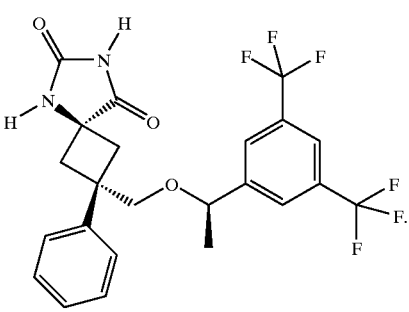

15. The compound of claim 1 having the formula

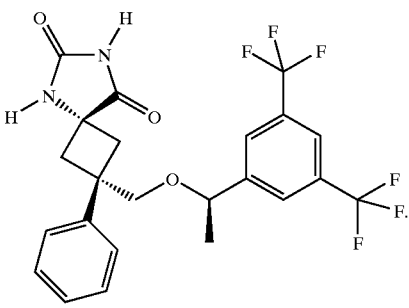

16. The compound of claim 1 having the formula

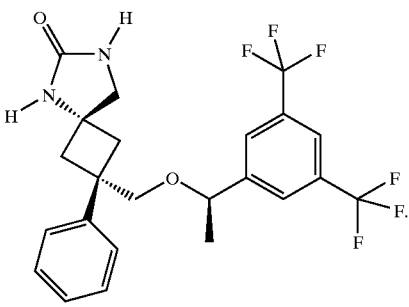

17. The compound of claim 1 having the formula:

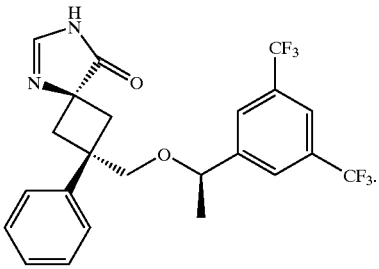

18. The compound of claim 1 having the formula:

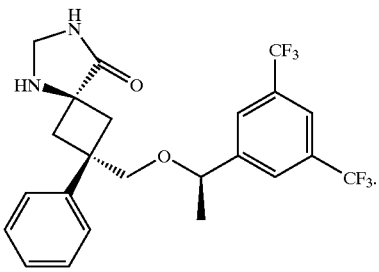

19. A pharmaceutical composition comprising a pharmaceutically acceptable carrier and at least one compound of claim 1.

20. A pharmaceutical composition comprising a pharmaceutically acceptable carrier, at least one serotonin reuptake inhibitor selected from the group consisting of fluoxetine, fluvoxamine, paroxetine, sertraline, citalopram, duloxetine, and venlafaxine and at least one compound of claim 1.

21. A method for treating a physiological disorder, symptom or disease in a patient in need of such treatment, comprising administering to said patient an effective amount of at least one compound of claim 1, wherein said physiological disorder, symptom or disease is a respiratory disease, depression, anxiety, phobia, bipolar disorder, alcohol dependence, psychoactive substance abuse, nociception, psychosis, schizophrenia, stress related disorder, obsessive/compulsive disorder, bulemia, anorexia nervosa, binge eating, sleep disorder, mania, premenstrual syndrome, gastrointestinal disorder, obesity, headache, neuropathic pain, post-operative pain, chronic pain syndrome, bladder disorder, genitourinary disorder, cough, emesis or nausea.

22. A method for treating a physiological disorder, symptom or disease in a patient in need of such treatment, comprising administering to said patient an effective amount of at least one compound of claim 1, and an effective amount of at least one active ingredient selected from the group consisting of: selective serotonin reuptake inhibitors selected from the group consisting of fluoxetine, fluvoxamine, paroxetine, sertraline, citalopram, duloxetine, and venlafaxine dopamine receptor agonists selected from apomorphine thereof serotonin 5-HT$_3$ receptor antagonists, selected from the group consisting of ondansetron, palonosetron, and granisetron and glucocorticoids selected from dexamethasone thereof wherein said physiological disorder, symptom or disease is a respiratory disease, depression, anxiety, phobia, bipolar disorder, alcohol dependence, psychoactive substance abuse, nociception, psychosis, schizophrenia, stress related disorder, obsessive/compulsive disorder, bulemia, anorexia, nervosa, binge eating, sleep disorder, mania, premenstrual syndrome, gastrointestinal disorder, obesity, headache, neuropathic pain, post-operative pain, chronic pain syndrome, bladder disorder, genitourinary disorder, cough, emesis or nausea.

23. The method of claim 22, wherein emesis is being treated and said active ingredient is ondansetron and/or dexamethasone.

24. The method of claim 21, wherein the physiological disorder, symptom or disease is emesis, depression, anxiety or cough.

25. The method of claim 24, further comprising administering to the patient an effective amount of at least one anti-depressant agent and/or at least one anti-anxiety agent selected from the group consisting of gepirone and nefazodone.

26. The method of claim 24 wherein depression is being treated and said method further comprises administering to the patient an effective amount of at least one selective serotonin reuptake inhibitor selected from the group consisting of fluoxetine, fluvoxamine, paroxetine, sertraline, citalopram, duloxetine, and venlafaxine.

\* \* \* \* \*

UNITED STATES PATENT AND TRADEMARK OFFICE
CERTIFICATE OF CORRECTION

PATENT NO. : 6,878,732 B2
DATED : April 12, 2005
INVENTOR(S) : Wrobleski, Michelle L.

It is certified that error appears in the above-identified patent and that said Letters Patent is hereby corrected as shown below:

Column 127,
Line 44, replace "$C_1$-$C_8$ alkyl" with -- $C_1$-$C_6$ alkyl --.

Column 128,
Line 2, replace "N==" with -- -N== --.
Line 35, replace "$C_1$-$C_5$ alkyl" with -- $C_1$-$C_6$ alkyl --.
Line 59, replace "(e.g., $C_1$-$O_2$ alkyl)" with -- (e.g., $C_1$-$C_2$ alkyl) --.

Column 129,
Line 45, replace "N=" with -- -N= --.

Column 130,
Line 66, replace "comprises" with -- comprise --.

Column 131,
Line 1, replace "N=" with -- -N= --.

Column 138,
Line 36, replace "anorexia, nervosa" with -- anorexia nervosa --.

Signed and Sealed this

Ninth Day of May, 2006

JON W. DUDAS
*Director of the United States Patent and Trademark Office*

UNITED STATES PATENT AND TRADEMARK OFFICE
CERTIFICATE OF CORRECTION

PATENT NO. : 6,878,732 B2
APPLICATION NO. : 10/386577
DATED : April 12, 2005
INVENTOR(S) : Wrobleski, Michelle L.

Page 1 of 1

It is certified that error appears in the above-identified patent and that said Letters Patent is hereby corrected as shown below:

Column 127,
Line 44, replace "$C_1$-$C_8$ alkyl" with -- $C_1$-$C_6$ alkyl --.

Column 128,
Line 2, replace "N==" with -- -N= --.
Line 35, replace "$C_1$-$C_5$ alkyl" with -- $C_1$-$C_6$ alkyl --.
Line 59, replace "(e.g., $C_1$-$O_2$ alkyl)" with -- (e.g., $C_1$-$C_6$ alkyl) --.

Column 129,
Line 45, replace "N=" with -- -N= --.

Column 130,
Line 66, replace "comprises" with -- comprise --.

Column 131,
Line 1, replace "N=" with -- -N= --.

Column 138,
Line 36, replace "anorexia, nervosa" with -- anorexia nervosa --.

This certificate supersedes certificate of correction issued May 9, 2006.

Signed and Sealed this

Twenty-second Day of August, 2006

JON W. DUDAS
*Director of the United States Patent and Trademark Office*

UNITED STATES PATENT AND TRADEMARK OFFICE
CERTIFICATE OF CORRECTION

PATENT NO. : 6,878,732 B2  
APPLICATION NO. : 10/386577  
DATED : April 12, 2005  
INVENTOR(S) : Michelle L. Wrobleski Page 1 of 1

It is certified that error appears in the above-identified patent and that said Letters Patent is hereby corrected as shown below:

Column 127,  
Line 44, replace "$C_1$-$C_8$ alkyl" with -- $C_1$-$C_6$alkyl --.

Column 128,  
Line 2, replace "N==" with -- -N= --.  
Line 35, replace "$C_1$-$C_5$ alkyl" with -- $C_1$-$C_6$alkyl --.  
Line 59, replace "(e.g., $C_1$-$O_2$ alkyl)" with --(e.g., $C_1$-$C_2$alkyl) --.

Column 129,  
Line 45, replace "N=" with -- -N= --.

Column 130,  
Line 66, replace "comprises" with -- comprise --.

Column 131,  
Line 1, replace "N=" with -- -N= --.

Column 138,  
Line 36, replace "anorexia, nervosa" with -- anorexia nervosa --.

This certificate supersedes Certificate of Correction issued May 9, 2006 and August 22, 2006.

Signed and Sealed this

Nineteenth Day of December, 2006

JON W. DUDAS  
*Director of the United States Patent and Trademark Office*